US011267844B2

(12) United States Patent
Tahri et al.

(10) Patent No.: US 11,267,844 B2
(45) Date of Patent: Mar. 8, 2022

(54) SPIROTHIETANE NUCLEOSIDES

(71) Applicant: Janssen Pharmaceutica NV, Beerse (BE)

(72) Inventors: Abdellah Tahri, Anderlecht (BE); Jean-François Bonfanti, Andé (FR); Tim Hugo Maria Jonckers, Heist-op-den-Berg (BE); Pierre Jean-Marie Bernard Raboisson, Rosieres (BE)

(73) Assignee: Janssen Pharmaceutica NV, Beerse (BE)

( * ) Notice: Subject to any disclaimer, the term of this patent is extended or adjusted under 35 U.S.C. 154(b) by 92 days.

(21) Appl. No.: 16/641,209

(22) PCT Filed: Aug. 31, 2018

(86) PCT No.: PCT/EP2018/073505
§ 371 (c)(1),
(2) Date: Feb. 21, 2020

(87) PCT Pub. No.: WO2019/043177
PCT Pub. Date: Mar. 7, 2019

(65) Prior Publication Data
US 2021/0139524 A1    May 13, 2021

(30) Foreign Application Priority Data

Sep. 1, 2017  (EP) .................................. 17189097

(51) Int. Cl.
| C07H 19/06 | (2006.01) |
| C07H 19/10 | (2006.01) |
| C07H 19/16 | (2006.01) |
| C07H 19/20 | (2006.01) |
| A61P 31/14 | (2006.01) |
| A61K 45/06 | (2006.01) |

(52) U.S. Cl.
CPC ............ *C07H 19/20* (2013.01); *A61K 45/06* (2013.01); *A61P 31/14* (2018.01); *C07H 19/06* (2013.01); *C07H 19/10* (2013.01); *C07H 19/16* (2013.01)

(58) Field of Classification Search
None
See application file for complete search history.

(56) References Cited

FOREIGN PATENT DOCUMENTS

| WO | WO-2012075140 A1 * | 6/2012 | ........... A61K 31/706 |
| WO | WO2012075140 A1 | 6/2012 | |
| WO | WO2016073756 A1 | 5/2016 | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
Bobeck, et al., Advances in nucleosides monophosphate prodrugs as anti-HCV agents, Antiviral Therapy, 2010, pp. 935-950, vol. 15.
Bundgaard, Hans, Design of Prodrugs, Elesevier, New York—Oxford, 1985, pp. 1-92.
Coats, et al., Chutes and ladders in hepatitis C nucleoside drug development, Antiviral Research, 2014, pp. 119-147, vol. 102.
Jones, Robert J. and Bischofberger, Norbert, Minireview: nucleotide prodrugs, Antiviral Research, 1994, pp. 1-17, vol. 27.
Krieger, et al., Enhancement of Hepatitis C Virus RNA Replication by Cell Culture-Adaptive Mutations, Journal of Virology, May 2001, 4614-4624, vol. 75/10.
Lohmann, et al., Replication of Subgenomic Hepatitis C Virus RNAs in a Hepatoma Cell Line, Science, 1999, pp. 110-113, vol. 285.
Meier C and Balzarini J, Application of the cycloSal-prodrug approach for improving the biological potential of phosphorylated biomolecules, Antiviral Research, Apr. 13, 2006, pp. 282-292, vol. 71.
Pertusati, et al., Medicinal chemistry of nucleoside phosphonate prodrugs for antiviral therapy, Antiviral Chemistry & Chemotherapy, 2012, pp. 181-203, vol. 22.
Pialoux, et al., Chikungunya, an epidemic arbovirosis. Lancet Infectious Diseases, May 2007, pp. 319-327, vol. 7.

(Continued)

*Primary Examiner* — Traviss C McIntosh, III
(74) *Attorney, Agent, or Firm* — Sofia Kopelevich

(57) ABSTRACT

The present invention relates to 2'-spirothietane nucleosides, and the phosphates and the prodrugs thereof, and the pharmaceutically acceptable salts and solvates thereof, and the use of such compounds as a medicament, in particular in the prevention and/or treatment of viral infections caused by viruses belonging to the Flaviviridae family and/or to the alphavirus genus. The present invention furthermore relates to pharmaceutical compositions or combination preparations of the compounds, and to the compositions or preparations for use as a medicament, more preferably for the prevention or treatment of viral infections caused by viruses belonging to the Flaviviridae family and/or to the alphavirus genus. The invention also relates to processes for the preparation of the compounds.

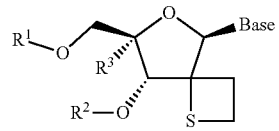

9 Claims, No Drawings

(56) References Cited

OTHER PUBLICATIONS

Schuliz, Carsten, Prodrugs of Biologically Active Phosphate Esters, Bioorganic & Medicinal Chemistry, Oct. 25, 2002, pp. 885-898, vol. 11.
Sofia, Michael J, et al., Nucleoside, Nucleotide, and Non-Nucleoside Inhibitors of Hepatitis C Virus NS5B RNA-Dependent RNA-Polymerase, Journal of Medicinal Chemistry, Dec. 16, 2011, pp. 2481-2531, vol. 55.
Sofia, Michael J, Nucleotide prodrugs for HCV therapy, Antiviral Chemistry & Chemotherapy, 2011, pp. 23-49, vol. 22.
Sofia, Michael J, Nucleotide Prodrugs for the Treatment of HCV Infection, Advances in Pharmacology, 2013, pp. 39-73, vol. 67.
International Search Report and Written Opinion for Int'l Application No. PCT/EP2018/073505 dated Oct. 2, 2018.

\* cited by examiner

SPIROTHIETANE NUCLEOSIDES

CROSS-REFERENCE TO RELATED APPLICATIONS

This application is a 371 national phase entry of International Application No. PCT/EP2018/073505, filed on Aug. 31, 2018, which claims priority to European Patent Application No. 17189097.3, filed Sep. 1, 2017, both of which are incorporated herein in their entirety.

FIELD OF THE INVENTION

The present invention relates to 2'-spirothietane nucleosides, and the phosphates and the prodrugs thereof, and the pharmaceutically acceptable salts and solvates thereof, and the use of such compounds as a medicament, in particular in the prevention and/or treatment of viral infections caused by viruses belonging to the Flaviviridae family and/or to the Alphavirus genus. The present invention furthermore relates to pharmaceutical compositions or combination preparations of the compounds, and to the compositions or preparations for use as a medicament, more preferably for the prevention or treatment of viral infections caused by viruses belonging to the Flaviviridae family and/or to the Alphavirus genus. The invention also relates to processes for the preparation of the compounds.

BACKGROUND OF THE INVENTION

Hepatitis C virus (HCV) is an enveloped, single-stranded, positive-sense RNA virus belonging to the Hepacivirus genus of the Flaviviridae family. The virus encodes an RNA-dependent RNA polymerase (RdRp), NS5B, which is essential for virus replication. Following the initial viral infection, majority of the infected individuals develop chronic hepatitis which can progress to liver fibrosis, leading to cirrhosis, end-stage liver disease, and HCC (hepatocellular carcinoma), making it the leading cause of liver transplantations. HCV is grouped into six major genotypes and more than 50 subtypes, which are differently distributed geographically. Genotype 1 is the predominant genotype in Europe and in the USA. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

The NS5B polymerase is essential for replication of the HCV RNA genome. This enzyme has elicited significant interest among medicinal chemists. Both nucleoside and non-nucleoside inhibitors of NS5B are known. Nucleoside inhibitors can act as a chain terminator or as a competitive inhibitor, or as both. To be active, nucleoside inhibitors must be taken up by the cell and converted in vivo to a triphosphate. This conversion to the triphosphate is commonly mediated by cellular kinases, which imparts additional structural requirements on a potential nucleoside polymerase inhibitor.

Arthropod-borne viruses are the causative agents of some most important emerging and re-emerging infectious diseases and cause significant global public health problems.

One of these viruses is the dengue virus, a Flavivirus that is transmitted by *Aedes* mosquitoes, and can cause severe and fatal diseases, such as dengue fever, dengue hemorrhagic fever and dengue shock syndrome. Dengue viruses can be divided into four distinct, but closely related serotypes, so-called DENV-1, -2, -3, and-4. Dengue is endemic in most tropical and sub-tropical regions around the world, predominantly in urban and semi-urban areas. According to the World Health Organization (WHO), 2.5 billion people, of which 1 billion are children, are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral diseases. Because of recent large outbreaks in countries in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but also the outbreaks tend to be more severe.

To prevent and/or control the diseases associated with dengue viral infection, the only available methods at present are mosquito eradication strategies to control the vector. Although progress is being made in the development of vaccines against dengue viruses, many difficulties are encountered. These include the existence of a phenomenon referred to as the antibody-dependent enhancement of virus infection (ADE).

Primary infection by one serotype provides lifelong immunity against that serotype but confers only partial and transient protection against a secondary infection by one of the other three serotypes. Following infection with another serotype, pre-existing heterologous antibodies form complexes with the newly infecting dengue virus but do not neutralize the pathogen. Instead, virus entry into cells is believed to be facilitated, resulting in uncontrolled virus replication and higher peak viral titers. In both primary and secondary infections, higher viral titers are associated with more severe dengue diseases. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue diseases is significantly higher due to an increased risk of secondary infection. Furthermore, today, specific antiviral drugs for the treatment or prevention of dengue fever virus infection are not available.

Other arthropod-borne viruses include the Alphavirus genus belonging to the Togaviridae family. The viruses in this genus cause diseases ranging from fever to severe polyarthritis to encephalitis. One alphavirus, chikungunya virus (CHIKV), caused recent outbreaks associated with severe morbidity (Pialoux G. et al., Lancet Infect Dis 2007; 7: 319-27).

CHIKV is a mosquito-borne viral disease which was first isolated between 1952-1953 from both man and mosquitoes. Since then, numerous CHIKV re-emergences have been documented in both Africa and Asia. Around 2005 to 2006, explosive outbreaks occurred in the South and Southeast Asia, the islands of the Indian Ocean, Africa and northern Italy. For example, the explosive outbreaks around 2006 in India, where 1.4 million cases were reported; in Reunion (France), where about 266 000 of the 775 000 inhabitants have been infected; and in Italy, where about 300 cases were reported. Although the fatal rate is approximately 0.1%, it causes highly painful arthritis-like symptoms that can last for months or even years. Recent outbreaks in France and Italy indicate that it can potentially constitute a threat to Europe and other regions of the world.

CHIKV is transmitted to human through a bite by infected *A albopictus* and *A aegypti* mosquitoes. After infection with chikungunya virus, there is an incubation period lasting 2-4 days on average, followed by disease symptoms such as high fever, rash, headache, back pain, myalgia, and arthralgia. Severe clinical manifestations of chikungunya infection can also occur, for example, hemorrhagic fever, conjunctivitis, photophobia, hepatitis, and stomatitis. Neurologic manifestations such as encephalitis, febrile seizures, meningeal syndrome and acute encephalopathy were also reported.

CHIKV is an enveloped, positive-sense, single-stranded RNA virus with a genome of approximately 12 kb nucleotides. The genome of CHIKV is organized as follows: 5' cap-nsP1-nsP2-nsP3-nsP4-(junction region)-C-E3-E2-6k-E1-poly(A)-3', in which the first four proteins (nsP1-4) are nonstructural proteins, and the structural proteins are the capsid (C) and the envelope proteins (E).

There is no distinct serotype difference among CHIKV isolated from Africa, Asia and the islands of the Indian Ocean. Phylogenetic analyses based on E1 gene sequences can group CHIKV into three genotypes (lineages): Asian, east/central/south African (ECSA), and West African. The Asian genotype differed from the ECSA and West African genotypes by nucleotide levels of ~5% and ~15%, respectively. The African genotypes (ECSA versus West African) were ~15% divergent. The amino acid identities across the three genotypes varied from 95.2 to 99.8%.

Currently no approved vaccines and antiviral drugs exist to protect and treat animals, more in particular humans, from CHIKV infection. Treatment is therefore purely symptomatic and is based on non-steroidal anti-inflammatory drugs. Since lacking a vaccine to combat chikungunya virus, its further spread and infection throughout the world, a high medical need exists to develop small chemical molecules to prevent and treat chikungunya virus infection. Similarly, there is currently no treatment available for combating other Alphaviruses, in particular, Sindbis virus and Simliki Forest virus. Therefore, medical need exists to develop small chemical molecules to prevent and treat infections by said viruses.

Additionally, there is still a great unmet medical need for therapeutics for the prevention or the treatment of viral infections in animals, more in particular in humans and especially for viral infections caused by Flaviviruses, more specifically HCV and dengue virus. WO 2012/075140 discloses 2'-spiro-nucleosides and derivatives thereof useful for treating a subject infected by hepatitis C virus or dengue virus. WO 2016/073756 discloses deuterated uridine nucleoside derivatives for the treatment or prevention of infections caused by HCV. However, and despite the availability of a number of anti-HCV regimens for the treatment of HCV, such as those based on combination with Sofosbuvir, and novel direct acting antiviral therapies undergoing clinical trials, there remains a need for alternative therapeutic drugs and/or therapies with advantageous properties. For example, high genetic barriers to resistance, broad genotypic coverage, favorable side effect and safety profiles and/or shorter treatment duration; furthermore, compounds with good antiviral potency, no or low levels of side-effects, a broad spectrum of activity against multiple dengue virus serotypes, a low toxicity and/or good pharmacokinetic or-dynamic properties are highly needed.

DESCRIPTION OF THE INVENTION

The present invention provides 2'-spirothietane nucleosides and the monophosphate, diphosphate, triphosphate, and the prodrugs thereof; and the pharmaceutically acceptable salts and solvates thereof, having activity against Flaviviridae, in particular HCV and/or Dengue virus, and/or alphaviruses, in particular, Chikungunya virus and/or Sindbis virus and/or Simliki Forest virus.

Thus, in one aspect the present invention provides spirothietane nucleosides of Formula (I)

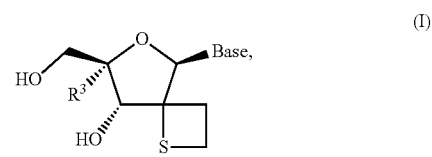

including all possible stereoisomeric forms thereof, wherein

Base is selected from the group consisting of (B-1), (B-2), (B-3a), (B-3b), (B-4) and (B-5)

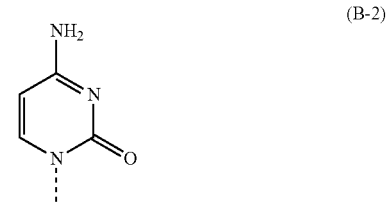

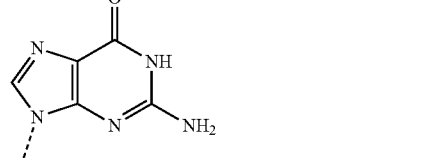

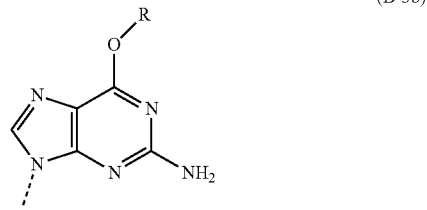

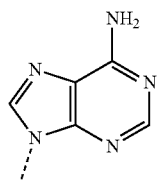

(B-4)

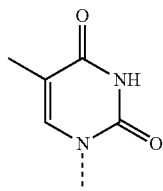

(B-5)

wherein R is hydrogen or $C_{1-6}$ alkyl; and
$R^3$ is selected from the group consisting of hydrogen, halo, methyl, $CH_2Cl$, $CH_2F$ and $N_3$;
and the monophosphate, the diphosphate, the triphosphate, and the prodrugs thereof, and the pharmaceutically acceptable salts and solvates thereof.

The present invention also relates to a pharmaceutical composition comprising a therapeutically effective amount, in particular an anti-virally effective amount, of the compound of Formula (I) or a stereoisomeric form thereof, or a phosphate (i.e. monophosphate, diphosphate or triphosphate) or a prodrug thereof, or a pharmaceutically acceptable salt or a solvate thereof, and a pharmaceutically acceptable carrier or excipient.

Additionally, the invention relates to a compound of Formula (I) or a stereoisomeric form thereof, or a phosphate (i.e. monophosphate, diphosphate or triphosphate) or a prodrug thereof, or a pharmaceutically acceptable salt or a solvate thereof, for use as a medicament, in particular for use in the treatment or in the prevention of Flaviviridae virus infections, particularly hepatitis C and/or Dengue virus infections, and/or in the treatment or in the prevention of alphavirus infections, particularly Chikungunya virus and/or Sindbis virus and/or Simliki Forest virus infections.

Additionally, the invention relates to the use of a compound of Formula (I) or a stereoisomeric form thereof, or a phosphate (i.e. monophosphate, diphosphate or triphosphate) or a prodrug thereof, or a pharmaceutically acceptable salt or a solvate thereof, in combination with an additional antiviral for use in the treatment or prevention of Flaviviridae virus infections, particularly hepatitis C and/or Dengue virus infections, and/or in the treatment or in the prevention of alphavirus infections, particularly Chikungunya virus and/or Sindbis virus and/or Simliki Forest virus infections.

Furthermore, the invention relates to a process for preparing a pharmaceutical composition according to the invention, characterized in that a pharmaceutically acceptable carrier is intimately mixed with a therapeutically effective amount, in particular an anti-virally effective amount, of a compound of Formula (I) or a stereoisomeric form thereof, or a phosphate (i.e. monophosphate, diphosphate or triphosphate) or a prodrug thereof, or a pharmaceutically acceptable salt or a solvate thereof.

The invention also relates to a product comprising a compound of Formula (I) or a stereoisomeric form thereof, or a phosphate (i.e. monophosphate, diphosphate or triphosphate) or a prodrug thereof, or a pharmaceutically acceptable salt or a solvate thereof, and an additional pharmaceutical agent, in particular an additional antiviral, as a combined preparation for simultaneous, separate or sequential use in the treatment or prevention of Flaviviridae virus infections, particularly hepatitis C and/or Dengue virus infections, and or in the treatment or in the prevention of alphavirus infections, particularly Chikungunya virus and/or Sindbis virus and/or Simliki Forest virus infections.

DETAILED DESCRIPTION OF THE INVENTION

As used herein the term "about" has the meaning known to the person skilled in the art. In certain embodiments, the term "about" may be left out and the exact amount is meant. In other embodiments the term "about" means that the numerical following the term "about" is in the range of ±15%, or of ±10%, or of ±5%, or of ±1%, of said numerical value.

As used herein "$C_1$-$C_4$alkyl" as a group or part of a group defines saturated straight or branched chain hydrocarbon radical having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl. "$C_1$-$C_{10}$alkyl" encompasses $C_1$-$C_6$alkyl radicals and the higher homologues thereof having 7, 8, 9 or 10 carbon atoms such as, for example, heptyl, 2-heptyl, 3-heptyl, 2-methylhexyl, octyl, 2-octyl, 3-octyl, nonyl, 2-nonyl, 3-nonyl, 2-butylpentyl, decyl, 2-decyl, and the like. Of interest amongst $C_1$-$C_{10}$alkyl is $C_1$-$C_6$alkyl, and $C_1$-$C_2$alkyl defines methyl and ethyl.

"$C_1$-$C_6$alkoxy" means a radical —O—$C_1$-$C_6$alkyl wherein $C_1$-$C_6$alkyl is as defined above. Examples of $C_1$-$C_6$alkoxy are methoxy, ethoxy, n-propoxy, or isopropoxy. "$C_3$-$C_7$cycloalkyl" includes cyclopropyl, cyclobutyl, cyclopentyl, cyclohexyl and cycloheptyl. Of interest is cyclopropyl and cyclobutyl.

The term "$C_2$-$C_6$alkenyl" as a group or part of a group defines straight and branched chained hydrocarbon radicals having saturated carbon-carbon bonds and at least one double bond, and having from 2 to 6 carbon atoms, such as, for example, 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_2$-$C_6$alkenyl is $C_3$-$C_6$alkenyl, in particular $C_3$-$C_4$alkenyl. Of interest amongst $C_2$-$C_6$alkenyl, in particular $C_3$-$C_6$alkenyl or $C_3$-$C_4$alkenyl, are those radicals having one double bond.

The term "halo" or "halogen" is generic to fluoro, chloro, bromo and iodo, in particular fluoro and chloro.

In one embodiment, the term "phenyl-$C_1$-$C_6$alkyl" is benzyl.

As used herein, the term "(=O)" or "oxo" forms a carbonyl moiety when attached to a carbon atom. It should be noted that an atom can only be substituted with an oxo group when the valency of that atom so permits.

The skilled person will realize that the 3- to 7-membered heterocyclic ring containing one oxygen atom particularly is a saturated ring and may be attached to the remainder of the molecule of Formula (I) through any available carbon atom. The 3- to 7-membered heterocyclic ring containing one oxygen atom is in particular a 3-, 4-, 5- or 6-membered ring.

Non-limiting examples include oxiranyl, oxetanyl, tetrahydrofuranyl, tetrahydropyranyl, and the like.

The term "phosphates" or "a phosphate" as used herein in general, refers to the monophosphate, diphosphate and/or triphosphate ester of a compound of Formula (I) or a subgroup thereof as used herein, unless otherwise stated, i.e. it refers to groups:

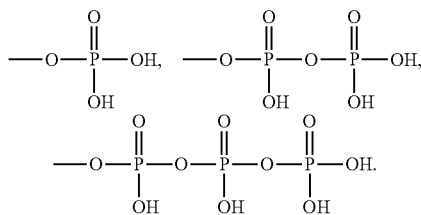

The compounds of the present invention are represented herein in their neutral form, it should be clear that the charged form(s), as present in biological systems, and known to the skilled person, is/are also included within the scope of the present invention.

The term "prodrug" of a compound of the invention includes any compound that when administered to a biological system, generates the biologically active agent having the desired pharmacological effect, i.e. the antiviral activity, as a result of a biotransformation or chemical transformation (e.g. spontaneous chemical reaction(s), enzyme catalyzed chemical reaction(s), and/or metabolic chemical reaction(s)). Ideally the prodrug is pharmacologically inactive. General information on prodrugs may be found e.g. in Bundegaard, H. "Design of Prodrugs" p. 1-92, Elesevier, New York-Oxford (1985).

In the case of antiviral nucleosides, the anabolite that elicits the actual inhibition of the viral polymerase enzyme is the nucleoside 5'-triphosphate. Nucleosides, their monophosphates, diphosphates and triphosphates may not be adequate for direct in vivo administration. For example, the first phosphorylation step of a nucleoside i.e., formation of the nucleoside 5'-monophosphate, is usually the most sensitive, and bypassing this first step has been successful in yielding high levels of the triphosphate. Modifications of the base and ribose of nucleosides have led to successful prodrug forming strategies in the field of antivirals, e.g., prodrugs of nucleoside 5'-monophosphates have overcome problems such as bioavailability and poor in vivo phosphorylation of the parent nucleoside to the active nucleoside 5'-triphosphate and delivered the drug substance into target organs. A number of nucleotide prodrugs have been developed and approved for the treatment of viral diseases, such as HIV, HCV, HBV, herpes virus, varicella-zoster virus, Epstein-Barr virus and cytomegalovirus.

Thus, several prodrug forming strategies are available in the field of antivirals and known to the skilled person. Such prodrug strategies have been reviewed, for instance, in Jones R J and Bischofberger N, Antiviral Research 1995, 27, 1-17; Sofia, M J, Antivir Chem Chemother 2011, 22, 23-49; Bobeck D R et al. Antiviral Therapy 2010, 15, 935-950; Sofia M J, Adv Pharmacol 2013, 67, 39-73; Schultz C, Bioorg Med Chem 2003, 11, 885-898; Pertusati F et al. Antivir Chem Chemother 2012, 22, 181-203; Sofia M J et al. J Med Chem 2012, 55(6), 2481-2531; Coats S J et al. Antiviral Res 2014, 102, 119-147; Meier C and Balzarini J, Antiviral Res 2006, 71 (2-3), 282-292, incorporated by reference herein in their entirety.

Prodrugs may be prepared by modifying functional groups present on the compound in such a way that the modified functional groups are cleaved, in vivo when such prodrug is administered to a subject. The modifications typically are achieved by synthesising the parent compound with a prodrug substituent. In general, prodrugs include compounds of the invention wherein a hydroxyl, amino or phosphate group is modified. In a particular embodiment, the prodrug is a 3'- and/or 5'-prodrug, as described in more detail herein.

Where the nucleoside derivatives of the invention contain an alcohol or an amino functional group, in particular at the 3'- and/or 5'-centre, a prodrug can comprise an ester formed by replacement of the hydrogen atom in the alcohol group(s) and/or the amino group(s).

In the case of alcohol functional groups, the hydrogen atom of the alcohol group(s) can be replaced with a group such as for example $C_1$-$C_6$alkanoyl, $C_1$-$C_6$alkanoyloxymethyl, 1-($C_1$-$C_6$alkanoyloxy)ethyl, S-acyl-2-thioethyl ester (SATE), 1-methyl-1-($C_1$-$C_6$)alkanoyloxy)ethyl, $C_1$-$C_6$alkoxycarbonyloxymethyl, N—$C_1$-$C_6$alkoxycarbonylamino methyl, succinoyl, α-amino $C_1$-$C_4$alkyl, α-amino $C_1$-$C_4$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

In the case of amino functional groups, a hydrogen atom of the amino group(s) can be replaced with a group such as for example $R^x$-carbonyl-, $R^x$O-carbonyl-, $R^x R^{x1}$N-carbonyl- wherein $R^x$ and $R^{x1}$ are each independently $C_1$-$C_{10}$alkyl, $C_3$-$C_7$cycloalkyl, benzyl, a natural α-aminoacyl, —C(OH) C(=O)OR$^{x2}$, wherein $R^{x2}$ is H, $C_1$-$C_6$alkyl or benzyl, wherein —C(OR$^{x2}$)R$^{x3}$ is $C_1$-$C_4$alkyl and $R^{x3}$ is $C_1$-$C_6$alkyl; carboxy$C_1$-$C_6$alkyl; NH$C_1$-$C_4$alkyl; NH($C_1$-$C_6$alkyl)$C_1$-$C_4$alkyl, N($C_1$-$C_6$alkyl)($C_1$-$C_6$alkyl)$C_1$-$C_4$alkyl; —C(R$^{x4}$)R$^{x5}$ wherein R$^{x4}$ is H or methyl and R$^{x5}$ is NH($C_1$-$C_6$alkyl) morpholino, N($C_1$-$C_6$alkyl)($C_1$-$C_6$alkyl)morpholino, piperidin-1-yl, pyrrolidin-1-yl, and the like.

Thus, particular examples of nucleoside prodrugs include, but are not limited to, those forming 5' and/or 3'-carboxylic acid esters, such as for example alkyl carboxylic acid esters and derivatives thereof, such as amino acid esters; examples include, but are not limited to 5'-O-isobutyrate ester, 3',5'-di-O-isobutyrate ester, pivaloyloxymethyl ester, acetoxymethyl ester, phthalidyl ester, indanyl and methoxymethyl ester, 0-valinyl ester, and the like.

Nucleoside prodrugs must be converted intracellularly into their 5'-triphosphate derivatives to inhibit viral polymerases. In some cases, activity may not be displayed in cellular assays as the nucleosides or nucleoside prodrugs may be poor substrates for one or more of the phosphorylation kinases, and/or may be too stable in the cellular assay setup. As already mentioned, in most cases, the formation of the monophosphate by the first kinase is the most problematic step. Prodrugs of the 5'-monophosphate nucleoside have been successfully delivered to bypass this first phosphorylation step, resulting in high intracellular levels of active triphosphate. Alternatively, or additionally, prodrugs of the 3'-monophosphate nucleoside can be formed. Several strategies exist and are known to the skilled person, to provide nucleotide prodrugs, in particular 3'- and/or 5'-monophoshate nucleoside prodrugs, more in particular, 5'-monophoshate nucleoside prodrugs, as antiviral agents. Examples of nucleotide prodrugs include, but are not limited to phosphoramidates, phosphates, cyclic 1-aryl-1,3-propanyl phosphate esters (HepDirect) and cyclic salicyl alcohol variants (cycloSal).

Phosphoramidates consist of a phosphate group derivatized with an amino acid and an aryloxy ester. Variants of this approach involve, for example, replacing the aryloxy ester with other esters, such as for example substituted alkyl esters, in particular, 5-acyl-2-thioethylester derivatives. Other versions involve two amide-linked amino acids (diamidates), or a simple amine at the amidate linkage, such as benzylamino or acyloxyethylamino.

Phosphates include for example, phosphates incorporating pivaloyloxymethyl (POM) or alkoxycarbonyloxymethyl (POC) chains, aryl phosphate esters, and lipid phosphate esters e.g. octadecyloxyethyl or hexadecyloxypropyl phosphate.

Preferably the prodrug is a 5'-phosphoramidate or a 5'-phosphate, but phosphoramidates and phosphates can also be formed alternatively or additionally, at the 3'-centre. Alternatively, a cyclic phosphate ester or phosphoramidate can form a bridge between the 3'-OH and 5'—OH groups, to form 3',5'-cyclic phosphate nucleotides, e.g. a cyclic monophosphate. Such cyclic phosphate esters or phosphoramidates can also include derivatives such as those discussed above in relation to phosphoramidates and phosphates, such as the incorporation of SATE (3',5'-cyclic phosphonate SATE), pivaloyloxymethyl (pivaloyloxymethyl cyclic phosphate), carbonates (carbonate cyclic phosphate esters), and simple alkyl ester groups.

Where the position of a radical on a molecular moiety is not specified (for example a substituent on phenyl) or is represented by a floating bonds, such radical may be positioned on any atom of such a moiety, as long as the resulting structure is chemically stable. When any variable is present more than once in the molecule, each definition is independent.

The skilled person will understand that the term "optionally substituted" means that the atom or radical indicated in the expression using "optionally substituted" may or may not be substituted (this means substituted or unsubstituted respectively).

The term "subject" as used herein, refers to a warm-blooded animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

Whenever used herein, the term "compounds of Formula (I)", or "the present compounds" or similar terms, is meant to include the compounds of Formula (I), in particular of Formula (I'), including the possible stereochemically isomeric forms, and their pharmaceutically acceptable salts and solvates.

As used herein, any chemical formula with bonds shown only as solid lines and not as solid or hashed wedged bonds, or otherwise indicated as having a particular configuration (e.g. R, S) around one or more atoms, contemplates each possible stereoisomer, or mixture of two or more stereoisomers.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%, or of 98% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary layers. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of Formula (I) can be obtained separately by conventional methods. Appropriate physical separation methods that may advantageously be employed are, for example, selective crystallization and chromatography, e.g. column chromatography.

The pharmaceutically acceptable addition salts comprise the therapeutically active non-toxic acid and base addition salt forms of the compounds of Formula (I), in particular of Formula (I'), and the phosphates (i.e. monophosphate, diphosphate, or triphosphate) thereof.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I), in particular of Formula (I'), containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of Formula (I), in particular of Formula (I'), as well as the phosphates (i.e. monophosphate, diphosphate, or triphosphate), the prodrugs and the salts thereof, are able to form. Such solvates are for example hydrates, alcoholates, e.g. ethanolates, propanolates, and the like.

Some of the compounds of Formula (I), in particular of Formula (I'), may also exist in their tautomeric form. For example, tautomeric forms of amide (—C(=O)—NH—) groups are iminoalcohols (—C(OH)=N—), which can become stabilized in rings with aromatic character. The uridine base is an example of such a form. Such forms, although not explicitly indicated in the structural formulae represented herein, are intended to be included within the scope of the present invention.

The present invention also includes isotope-labeled compounds of Formula (I) or any subgroup of Formula (I), in particular of Formula (I'), wherein one or more of the atoms is replaced by an isotope that differs from the one(s) typically found in nature. Examples of such isotopes include isotopes of hydrogen, such as $^2$H and $^3$H; carbon, such as $^{13}$C and $^{14}$C; nitrogen, such as $^{13}$N and $^{15}$N; oxygen, such as $^{15}$O, $^{17}$O and $^{18}$O, phosphorus, such as $^{31}$P and $^{32}$P, sulphur, such as $^{35}$S; fluorine, such as $^{18}$F; chlorine, such as $^{36}$Cl; bromine such as $^{75}$Br, $^{76}$Br, $^{77}$Br and $^{82}$Br; and iodine, such as $^{18}$F; $^{123}$I, $^{124}$I, $^{125}$I and $^{131}$I. Isotope-labeled compounds of the invention can be prepared by processes analogous to those described herein by using the appropriate isotope-labeled reagents or starting materials, or by art-known techniques. The choice of the isotope included in an isotope-labeled compound depends on the specific application of that compound. For example, for tissue distribution assays, a radioactive isotope such as $^3$H or $^{14}$C is incorporated. For radio-imaging applications, a positron emitting isotope such as $^{11}$C, t $^{13}$N or $^{15}$O will be useful. The incorporation of deuterium may provide greater metabolic stability, resulting in, e.g. an increased in vivo half-life of the compound or reduced dosage requirements.

In a particular embodiment, the invention provides compounds of Formula (I) having Formula (I'):

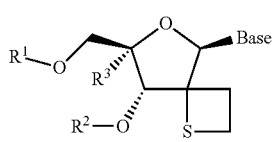

(I')

and stereoisomeric forms thereof, wherein

Base is selected from the group consisting of (B-1), (B-2), (B-3a), (B-3b), (B-4) and (B-5)

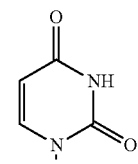

(B-1)

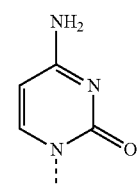

(B-2)

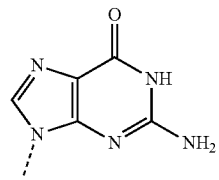

(B-3a)

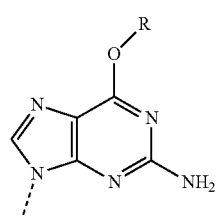

(B-3b)

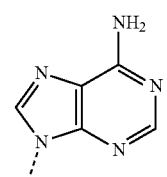

(B-4)

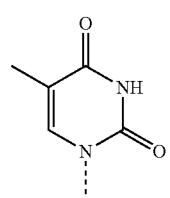

(B-5)

wherein R is hydrogen or $C_{1-6}$ alkyl;

$R^1$ is selected from the group consisting of hydrogen,

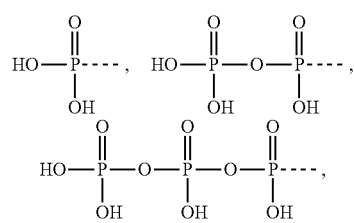

a group of formula (a-1), a group of formula (a-2), a group of formula (a-3), and a group of formula (a-4)

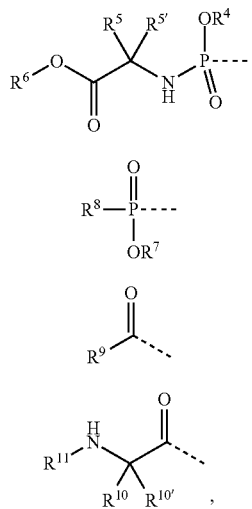

wherein $R^4$ and $R^7$ are each independently selected from the group consisting of hydrogen, phenyl, naphthyl, quinolinyl, iso-quinolinyl, and pyridyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{16}R^{16'}$; or $R^4$ and $R^7$ are each independently indolyl, optionally substituted at its nitrogen atom with $C_1$-$C_6$alkyl or $C_1$-$C_6$alkyloxycarbonyl and/or at any available carbon atom with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{17}R^{17'}$;

$R^5$, $R^{5'}$, $R^{10}$ and $R^{10'}$ are each independently selected from the group consisting of hydrogen, $C_1$-$C_6$alkyl, benzyl, and phenyl; or $R^5$ and $R^{5'}$, or $R^{10}$ and $R^{10'}$, together with the carbon atom to which they are attached form a $C_3$-$C_7$cycloalkanediyl or a 3- to 7-membered heterocyclic ring containing one oxygen atom;

$R^6$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{18}R^{18'}$;

$R^8$ is —$OR^{19}$ or —$NR^{20}R^{20'}$; $R^9$ is selected from the group consisting of $C_1$-$C_6$alkyl, phenyl, and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of halo and $C_1$-$C_6$alkyloxy;

$R^{11}$ is selected from the group consisting of hydrogen, $C_1$-$C_{10}$alkyl, $C_3$-$C_7$cycloalkyl, phenyl or phenyl-$C_1$-$C_6$alkyl-, wherein the phenyl moiety in phenyl or phenyl-$C_1$-$C_6$alkyl- is optionally substituted with 1, 2 or 3 substituents each independently selected from the group consisting of hydroxy, $C_1$-$C_6$alkoxy, and $NR^{23}R^{23'}$;

$R^{19}$ is selected from the group consisting of $C_1$-$C_6$alkyl, $C_3$-$C_7$cycloalkyl, oxetanyl, ($C_1$-$C_6$alkoxy)$C_1$-$C_6$alkyl-, —$CH_2$—O—(C=O)$C_1$-$C_6$alkyl, and —$CH_2$—O—(C=O)O$C_1$-$C_6$alkyl;

$R^{20}$ is selected from the group consisting of hydrogen, $C_1$-$C_6$alkyl, and $C_3$-$C_7$cycloalkyl; and $R^{20'}$ is selected from the group consisting of $C_1$-$C_6$alkyl, $C_3$-$C_7$cycloalkyl, and ($C_1$-$C_6$alkoxy)$C_1$-$C_6$alkyl-; or —$NR^{20}R^{20'}$ together form an azetidinyl, a pyrrolidinyl or a piperidinyl ring, each of which may be optionally substituted with a group consisting of hydroxy, $C_1$-$C_6$alkyl, $C_1$-$C_6$alkyloxy, and (C=O)—$OR^{21}$ wherein $R^{21}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{22}R^{22'}$;

$R^2$ is hydrogen or a group of formula (b)

wherein $R^{12}$ is selected from the group consisting of $C_1$-$C_6$alkyl, phenyl, and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of halo and $C_1$-$C_6$alkyloxy; or $R^1$ and $R^2$ are bound to form a divalent radical of formula (c-1) or (c-2)

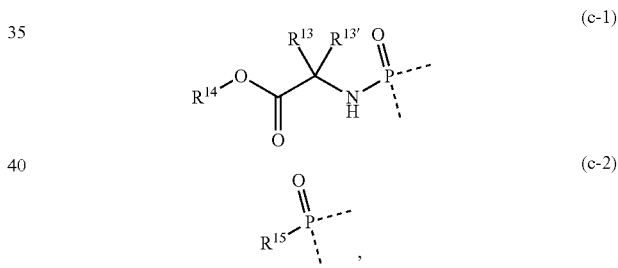

wherein $R^{13}$ and $R^{13'}$ are each independently selected from the group consisting of hydrogen, $C_1$-$C_6$alkyl, benzyl, and phenyl; or $R^{13}$ and $R^{13'}$, together with the carbon atom to which they are attached form a $C_3$-$C_7$cycloalkanediyl or a 3- to 7-membered heterocyclic ring containing one oxygen atom;

$R^{14}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{24}R^{24'}$;

$R^{15}$ is —$OR^{25}$ or —$NR^{26}R^{26'}$, wherein $R^{25}$ is selected from the group consisting of hydrogen; $C_1$-$C_6$alkyl; $C_1$-$C_3$alkyl substituted with 1, 2 or 3 substituents each independently selected from the group consisting of phenyl, naphthyl, $C_3$-$C_7$cycloalkyl, hydroxyl and $C_1$-$C_6$alkyloxy; $C_3$-$C_7$cycloalkyl; ($C_1$-$C_6$alkoxy)$C_1$-$C_6$alkyl-; —$CH_2$—O—(C=O)$C_1$-$C_6$alkyl; —$CH_2$—O—(C=O)O$C_1$-$C_6$alkyl; a 3- to 7-membered heterocyclic ring containing one oxygen atom; and Ar; wherein Ar is selected from the group consisting of phenyl, naphthyl, quinolinyl, isoquinolinyl, and pyridyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{27}R^{27'}$; or Ar is indolyl, optionally substituted at its nitrogen atom with $C_1$-$C_6$alkyl or $C_1$-$C_6$alkyloxycarbonyl and/or at any available carbon atom with 1, 2, or 3 substituents each independently selected from the group consisting of halo, $C_1$-$C_6$alkyl, $C_2$-$C_6$alkenyl, $C_1$-$C_6$alkoxy, hydroxy, and $NR^{28}R^{28'}$;

$R^{26}$ is selected from the group consisting of hydrogen, $C_1$-$C_6$alkyl, and $C_3$-$C_7$cycloalkyl; and $R^{26'}$ is selected from the group consisting of $C_1$-$C_6$alkyl, $C_3$-$C_7$cycloalkyl, and $(C_1$-$C_6$alkoxy$)C_1$-$C_6$alkyl-; or —$NR^{26}R^{26'}$ together form an azetidinyl, a pyrrolidinyl or a piperidinyl ring, each of which may be optionally substituted with a group consisting of hydroxy, $C_1$-$C_6$alkyl, $C_1$-$C_6$alkyloxy, and $(C=O)$—$OR^{27}$ wherein $R^{27}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{29}R^{29'}$;

$R^{16}$, $R^{16'}$, $R^{17}$, $R^{17'}$, $R^{18}$, $R^{18'}$, $R^{22}$, $R^{22'}$, $R^{23}$, $R^{23'}$, $R^{24}$, $R^{24'}$, $R^{27}$, $R^{27'}$, $R^{28}$, $R^{28'}$, $R^{29}$ and $R^{29'}$ are each independently selected from hydrogen and $C_1$-$C_6$alkyl; and $R^3$ is selected from the group consisting of hydrogen, halo, methyl, $CH_2Cl$, $CH_2F$ and $N_3$;

and the pharmaceutically acceptable salts and the solvates thereof.

The group —NH—C($R^5$)($R^{5'}$)—C(=O)— or —NH—C($R^{13}$)($R^{13'}$)—C(=O)— may form an amino acid residue, which includes natural and non-natural amino acid residues. Of interest are alanine (Ala), glycine (Gly) and dimethyl glycine (Dmg). Also of interest are those amino acid residues wherein $R^{5'}$ or $R^{13'}$ is hydrogen. Where in the latter instance $R^{5'/13'}$ is other than hydrogen, the amino acid residue has a chiral center and the configuration at the asymmetric carbon atom may be that of an L-amino acid. Examples include alanine (Ala), valine (Val), isoleucine (Ile), α-aminobutyric acid (ABA also named 2-aminobutyric acid or ethylglycine), phenylalanine (Phe) and phenylglycine (Phg) residues, in particular L-Ala, L-Val, L-Ile, L-ABA, L-Phe and L-Phg. An example of an amino acid residue wherein $R^5$ and $R^{5'}$ or $R^{13}$ and $R^{13'}$ together with the carbon atom to which they are attached form $C_3$-$C_7$cycloalkanediyl, is 1,1-cyclopropylamino acid. Similarly, the groups —$NR^{20}R^{20'}$ or —$NR^{26}R^{26'}$, forming a pyrrolidinyl ring substituted with $(C=O)OR^{21}$ or $(C=O)OR^{27}$, respectively, in particular

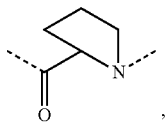

form a proline residue, preferably an L-proline residue.

Subgroups of compounds of Formula (I) are those compounds of Formula (I'), or subgroups of compounds of Formula (I'), as defined herein, wherein $R^1$ is a group of formula (a-1)

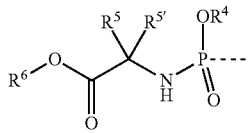

(a-1)

Subgroups of compounds of Formula (I) are those compounds of Formula (I'), or subgroups of compounds of Formula (I'), as defined herein, wherein:

(a) $R^4$ is phenyl, optionally substituted with 1, 2, or with 3 substituents each independently selected from halo, $C_1$-$C_6$alkyl, $C_3$-$C_6$alkenyl, $C_1$-$C_6$alkoxy, hydroxy, and $NR^{16}R^{16'}$; or $R^4$ is naphthyl, optionally substituted with halo, $C_1$-$C_6$alkyl, or $C_1$-$C_6$alkoxy; or $R^4$ is indolyl;

(b) $R^4$ is phenyl, optionally substituted with 1, with 2, or with 3 substituents, each independently selected from halo, $C_1$-$C_6$alkyl, $C_3$-$C_6$alkenyl, $C_1$-$C_6$alkoxy, hydroxy, and $NR^{16}R^{16'}$; or $R^4$ is naphthyl; or $R^4$ is indolyl;

(c) $R^4$ is phenyl, optionally substituted with 1 or with 2 substituents, each independently selected from halo, $C_1$-$C_6$alkyl, $C_3$-$C_6$alkenyl, $C_1$-$C_6$alkoxy, hydroxy, and $NR^{16}R^{16'}$; or $R^4$ is naphthyl; or $R^4$ is indolyl;

(d) $R^4$ is phenyl, optionally substituted with 1 or with 2 substituents each independently selected from halo, $C_1$-$C_6$alkyl, $C_3$-$C_6$alkenyl, and $C_1$-$C_6$alkoxy, or $R^4$ is naphthyl;

(e) $R^4$ is phenyl, optionally substituted with halo or with 1 or 2 $C_1$-$C_6$alkyl radicals, or $R^4$ is naphthyl;

(f) $R^4$ is phenyl, halophenyl, di$C_1$-$C_4$alkylphenyl, or naphthyl;

(g) $R^4$ is phenyl;

(h) $R^4$ is naphthyl.

Subgroups of compounds of Formula (I) are those compounds of Formula (I'), or subgroups of compounds of Formula (I'), as defined herein, wherein (a) $R^5$ is methyl and $R^{5'}$ is methyl; or (b) $R^5$ is hydrogen and $R^{5'}$ is phenyl or $C_1$-$C_6$alkyl in particular $C_1$-$C_4$alkyl, such as methyl, ethyl, isopropyl or isobutyl. Subgroups of compounds of Formula (I) are those compounds of Formula (I'), or subgroups of compounds of Formula (I'), as defined herein, wherein the

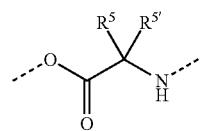

moiety is glycyl, dimethylglycyl, α-aminobutyryl, phenylglycine, isoleucyl, alanyl, phenylalanyl or valyl (respectively Gly, Dmg, ABA, Phg, Ile, Ala, Phe or Val; in particular L-ABA, L-Phg, L-Ile, L-Ala, L-Phe or L-Val).

Subgroups of compounds of Formula (I) are those compounds of Formula (I'), or of subgroups of compounds of Formula (I'), as defined herein, wherein $R^5$ is hydrogen, $C_1$-$C_6$alkyl, benzyl, or phenyl; and $R^{5'}$ is hydrogen, $C_1$-$C_6$alkyl, benzyl, or phenyl.

Subgroups of compounds of Formula (I) are those compounds of Formula (I'), or subgroups of compounds of Formula (I), as defined herein, wherein the moiety has the structure

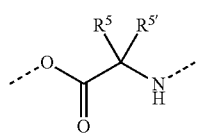

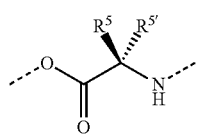

wherein $R^5$ is hydrogen and $R^{5'}$ is hydrogen, phenyl, $C_1$-$C_6$alkyl, benzyl; or
$R^5$ is hydrogen and $R^{5'}$ is hydrogen or $C_1$-$C_6$alkyl;
$R^5$ is hydrogen and $R^{5'}$ is $C_1$-$C_2$alkyl;
$R^5$ is hydrogen and $R^{5'}$ is methyl.

In one embodiment $R^5$ and $R^{5'}$ together with the carbon atom to which they are attached form $C_3$-$C_7$cycloalkanediyl; or in particular form $C_3$-$C_4$cycloalkanediyl; or in particular form cyclopropylidene.

Subgroups of compounds of Formula (I) are those compounds of Formula (I'), or of subgroups of compounds of Formula (I'), as defined herein, wherein
(a) $R^6$ is $C_1$-$C_6$alkyl, benzyl, or phenyl optionally substituted with 1, 2 or 3 substituents, each independently selected from hydroxy, $C_1$-$C_6$alkoxy, and $NR^{18}R^{18'}$, wherein $R^{18}$ is hydrogen and $R^{18'}$ is hydrogen or $C_1$-$C_6$alkyl;
(b) $R^6$ is $C_1$-$C_6$alkyl or benzyl;
(c) $R^6$ is $C_1$-$C_6$alkyl;
(d) $R^6$ is $C_1$-$C_4$alkyl;
(e) $R^6$ is methyl, ethyl, or t-butyl;
(f) $R^6$ is $C_3$-$C_7$cycloalkyl.

Subgroups of compounds of Formula (I) are those compounds of Formula (I'), or of subgroups of compounds of Formula (I'), as defined herein, wherein
$R^4$ is phenyl, halophenyl, di$C_1$-$C_4$alkylphenyl, or naphthyl;
$R^5$ and $R^{5'}$ are each independently hydrogen, $C_1$-$C_6$alkyl, benzyl or phenyl; and
$R^6$ is $C_1$-$C_6$alkyl.

Subgroups of compounds of Formula (I) are those compounds of Formula (I'), or of subgroups of compounds of Formula (I'), as defined herein, wherein $R^1$ and $R^2$ are bound to form a divalent radical of (c-2)

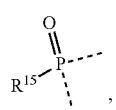

(c-2)

wherein
$R^{15}$ is —$OR^{25}$ wherein $R^{25}$ is selected from the group consisting of hydrogen, $C_1$-$C_6$alkyl; phenyl; $C_3$-$C_7$cycloalkyl; and $C_1$-$C_3$alkyl substituted with 1, 2 or 3 substituents each independently selected from the group consisting of phenyl, naphthyl, $C_3$-$C_7$cycloalkyl, hydroxyl and $C_1$-$C_6$alkyloxy. In another embodiment, $R^{25}$ is $C_1$-$C_6$alkyl or $C_1$-$C_2$alkyl substituted with phenyl, $C_1$-$C_2$alkyloxy or $C_3$-$C_7$cycloalkyl. In a further embodiment, $R^{25}$ is $C_3$-$C_7$cycloalkyl, more in particular, cyclopentyl. In a further embodiment, $R^{25}$ is $C_2$-$C_4$alkyl, more in particular, i-propyl.

In a particular embodiment, the invention provides compounds of Formula (I') as defined herein, wherein
$R^1$ is selected from the group consisting of hydrogen,

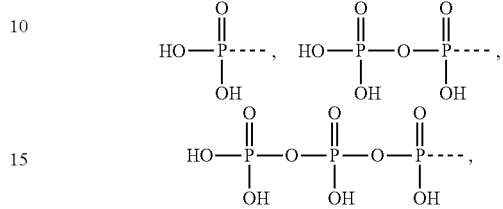

a group of formula (a-1), a group of formula (a-2) and a group of formula (a-3); wherein
$R^4$ and $R^7$ are each independently phenyl or naphthyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{16}R^{16'}$; wherein $R^{16}$ and $R^{16'}$ are each independently selected from hydrogen and $C_1$-$C_6$alkyl; or $R^4$ and $R^7$ are each independently indolyl;

$R^5$ and $R^{5'}$ are each independently selected from the group consisting of hydrogen, $C_1$-$C_6$alkyl, benzyl, and phenyl; or $R^5$ and $R^{5'}$ together with the carbon atom to which they are attached form a $C_3$-$C_7$cycloalkanediyl;

$R^6$ is selected from the group consisting of $C_1$-$C_{10}$alkyl, $C_3$-$C_7$cycloalkyl and phenyl-$C_1$-$C_6$alkyl-;

$R^8$ is —$OR^{19}$ or —$NR^{20}R^{20'}$; wherein $R^{19}$ is $C_1$-$C_6$alkyl or $C_3$-$C_7$cycloalkyl;

$R^{20}$ is hydrogen and $R^{20'}$ is $C_1$-$C_6$alkyl or $C_3$-$C_7$cycloalkyl; and $R^9$ is $C_1$-$C_6$alkyl;

$R^2$ is hydrogen or a group of formula (b), wherein $R^{12}$ is $C_1$-$C_6$alkyl; or $R^1$ and $R^2$ are bound to form a divalent radical of formula (c-1) or (c-2), wherein $R^{13}$ and $R^{13'}$ are each independently selected from the group consisting of hydrogen, $C_1$-$C_6$alkyl, benzyl, and phenyl; or $R^{13}$ and $R^{13'}$, together with the carbon atom to which they are attached form a $C_3$-$C_7$cycloalkanediyl;

$R^{14}$ is selected from the group consisting of $C_1$-$C_{10}$alkyl, $C_3$-$C_7$cycloalkyl and phenyl-$C_1$-$C_6$alkyl-; and $R^{15}$ is —$OR^{25}$ or —$NR^{26}R^{26'}$, wherein $R^{25}$ is selected from the group consisting of $C_1$-$C_6$alkyl; phenyl; $C_3$-$C_7$cycloalkyl; and $C_1$-$C_3$alkyl substituted with 1, 2 or 3 substituents each independently selected from the group consisting of phenyl, naphthyl, $C_3$-$C_7$cycloalkyl, hydroxyl and $C_1$-$C_6$alkyloxy; $R^{26}$ is hydrogen; and $R^{26'}$ is $C_1$-$C_6$alkyl or $C_3$-$C_7$cycloalkyl;

and the pharmaceutically acceptable salts and the solvates thereof.

In another embodiment, the invention provides compounds of Formula (I') as defined herein, wherein
Base is selected from the group consisting of (B-1), (B-2) and (B-3a); and
$R^3$ is selected from the group consisting of hydrogen, halo, and $N_3$.

In a particular embodiment, the invention provides compounds of Formula (I') as defined herein, wherein Base is selected from the group consisting of (B-1), (B-2) and (B-3a);

R$^1$ is selected from the group consisting of hydrogen,

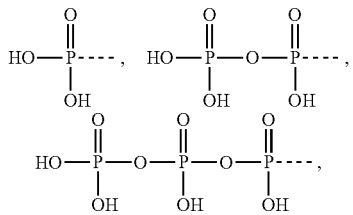

a group of formula (a-1), a group of formula (a-2) and a group of formula (a-3); wherein R$^4$ and R$^7$ are each independently phenyl or naphthyl, each of which being optionally substituted with 1, 2, or 3 substituents, each independently selected from the group consisting of halo, C$_1$-C$_6$alkyl, C$_2$-C$_6$alkenyl, C$_1$-C$_6$alkoxy, hydroxy, and NR$^{16}$R$^{16'}$; wherein R$^{16}$ and R$^{16'}$ are each independently selected from hydrogen and C$_1$-C$_6$alkyl; or R$^4$ and R$^7$ are each independently indolyl;

R$^5$ and R$^{5'}$ are each independently selected from the group consisting of hydrogen, C$_1$-C$_6$alkyl, benzyl, and phenyl; or R$^5$ and R$^{5'}$ together with the carbon atom to which they are attached form a C$_3$-C$_7$cycloalkanediyl;

R$^6$ is selected from the group consisting of C$_1$-C$_{10}$alkyl, C$_3$-C$_7$cycloalkyl and phenyl-C$_1$-C$_6$alkyl-;

R$^8$ is —OR$^{19}$ or —NR$^{20}$R$^{20'}$; wherein R$^{19}$ is C$_1$-C$_6$alkyl or C$_3$-C$_7$cycloalkyl;

R$^{20}$ is hydrogen and R$^{20'}$ is C$_1$-C$_6$alkyl or C$_3$-C$_7$cycloalkyl; and R$^9$ is C$_1$-C$_6$alkyl; and R$^2$ is hydrogen or a group of formula (b), wherein R$^{12}$ is C$_1$-C$_6$alkyl; or R$^1$ and R$^2$ are bound to form a divalent radical of formula (c-1) or (c-2), wherein R$^{13}$ and R$^{13'}$ are each independently selected from the group consisting of hydrogen, C$_1$-C$_6$alkyl, benzyl, and phenyl; or R$^{13}$ and R$^{13'}$, together with the carbon atom to which they are attached form a C$_3$-C$_7$cycloalkanediyl;

R$^{14}$ is selected from the group consisting of C$_1$-C$_{10}$alkyl, C$_3$-C$_7$cycloalkyl and phenyl-C$_1$-C$_6$alkyl-;

R$^{15}$ is —OR$^{25}$ or —NR$^{26}$R$^{26'}$, wherein R$^{25}$ is selected from the group consisting of C$_1$-C$_6$alkyl; phenyl; C$_3$-C$_7$cycloalkyl; and C$_1$-C$_3$alkyl substituted with 1, 2 or 3 substituents each independently selected from the group consisting of phenyl, naphthyl, C$_3$-C$_7$cycloalkyl, hydroxyl and C$_1$-C$_6$alkyloxy; R$^{26}$ is hydrogen; and R$^{26'}$ is C$_1$-C$_6$alkyl or C$_3$-C$_7$cycloalkyl; and R$^3$ is selected from the group consisting of hydrogen, halo, and N$_3$;

and the pharmaceutically acceptable salts and the solvates thereof.

In a further embodiment, the invention provides compounds of Formula (I') as defined herein, wherein Base is selected from the group consisting of (B-1), (B-2) and (B-3a);

R' is selected from the group consisting of hydrogen,

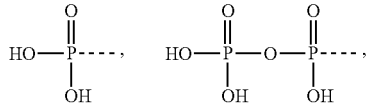

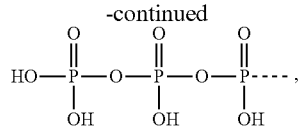

a group of formula (a-1), a group of formula (a-2) and a group of formula (a-3); wherein R$^4$ and R$^7$ are each independently phenyl or naphthyl, each of which being optionally substituted with 1 halo substituent;

R$^5$ and R$^{5'}$ are each independently selected from the group consisting of hydrogen and C$_1$-C$_6$alkyl;

R$^6$ is C$_1$-C$_{10}$alkyl;

R$^8$ is —OR$^{19}$ or —NR$^{20}$R$^{20'}$; wherein R$^{19}$ is C$_1$-C$_6$alkyl or C$_3$-C$_7$cycloalkyl;

R$^{20}$ is hydrogen and R$^{20'}$ is C$_1$-C$_6$alkyl or C$_3$-C$_7$cycloalkyl; and R$^9$ is C$_1$-C$_6$alkyl; and R$^2$ is hydrogen or a group of formula (b), wherein R$^{12}$ is C$_1$-C$_6$alkyl; or R$^1$ and R$^2$ are bound to form a divalent radical of formula (c-1) or (c-2), wherein R$^{13}$ and R$^{13'}$ are each independently selected from the group consisting of hydrogen and C$_1$-C$_6$alkyl;

R$^{14}$ is C$_1$-C$_{10}$alkyl;

R$^{15}$ is —OR$^{25}$ or —NR$^{26}$R$^{26'}$, wherein R$^{25}$ is selected from the group consisting of hydrogen, C$_1$-C$_6$alkyl and C$_3$-C$_7$cycloalkyl; R$^{26}$ is hydrogen; and R$^{26'}$ is C$_1$-C$_6$alkyl or C$_3$-C$_7$cycloalkyl; and R$^3$ is selected from the group consisting of hydrogen, halo, and N$_3$;

and the pharmaceutically acceptable salts and the solvates thereof.

In another embodiment, the invention provides compounds of Formula (I') as defined herein, wherein Base is selected from the group consisting of (B-1), (B-2) and (B-3a);

R$^1$ is selected from the group consisting of hydrogen,

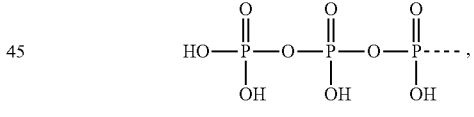

a group of formula (a-1), a group of formula (a-2) and a group of formula (a-3); wherein R$^4$ and R$^7$ are each phenyl optionally substituted with 1 halo substituent;

R$^5$ and R$^{5'}$ are each independently selected from the group consisting of hydrogen and C$_1$-C$_6$alkyl;

R$^6$ is C$_1$-C$_{10}$alkyl;

R$^8$ is —OR$^{19}$; wherein R$^{19}$ is C$_1$-C$_6$alkyl;

R$^9$ is C$_1$-C$_6$alkyl; and

R$^2$ is hydrogen or a group of formula (b), wherein R$^{12}$ is C$_1$-C$_6$alkyl; or R$^1$ and R$^2$ are bound to form a divalent radical of formula (c-2), wherein R$^{13}$ and R$^{13'}$ are each independently selected from the group consisting of hydrogen and C$_1$-C$_6$alkyl;

R$^{14}$ is C$_1$-C$_{10}$alkyl;

R$^{15}$ is —OR$^{25}$ or —NR$^{26}$R$^{26'}$, wherein R$^{25}$ is C$_3$-C$_7$cycloalkyl; R$^{26}$ is hydrogen; and R$^{26'}$ is C$_3$-C$_7$cycloalkyl; and $R^3$ is selected from the group consisting of hydrogen, halo, and $N_3$;

and the pharmaceutically acceptable salts and the solvates thereof.

In an additional embodiment, the invention provides compounds of Formula (I') as defined herein, wherein R' is selected from the group consisting of hydrogen,

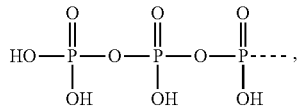

and a group of formula (a-1);

or $R^1$ and $R^2$ are bound to form a divalent radical of formula (c-2).

In another embodiment, the invention provides compounds of Formula (I') as defined herein, wherein Base is selected from the group consisting of (B-1), (B-2) and (B-3a);

$R^1$ is

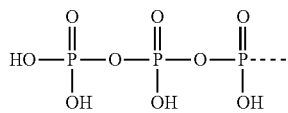

or a group of formula (a-1), wherein
$R^4$ is phenyl optionally substituted with 1 halo substituent;
$R^5$ and $R^{5'}$ are each independently selected from the group consisting of hydrogen and $C_1$-$C_6$alkyl, in particular methyl;
$R^6$ is $C_1$-$C_{10}$alkyl, in particular i-propyl or n-butyl;
$R^2$ is hydrogen; and
$R^3$ is selected from the group consisting of hydrogen, halo in particular fluoro, and $N_3$;

and the pharmaceutically acceptable salts and the solvates thereof.

In another embodiment, the invention provides compounds of Formula (I') as defined herein, wherein
Base is (B-1); $R^1$ is a group of formula (a-1); $R^2$ is hydrogen; and $R^3$ is hydrogen or $N_3$; or
Base is (B-2); $R^1$ is hydrogen or a group of formula (a-1); $R^2$ is hydrogen; and $R^3$ is halo, in particular fluoro; wherein
$R^4$ is phenyl optionally substituted with 1 halo substituent;
$R^5$ and $R^{5'}$ are each independently selected from the group consisting of hydrogen and $C_1$-$C_6$alkyl, in particular methyl; and
$R^6$ is $C_1$-$C_{10}$alkyl, in particular i-propyl;

and the pharmaceutically acceptable salts and the solvates thereof.

In another embodiment, the invention provides compounds of Formula (I') as defined herein, wherein
Base is (B-1);
$R^1$ is a group of formula (a-1), wherein
$R^4$ is phenyl optionally substituted with 1 halo substituent;
$R^5$ and $R^{5'}$ are each independently selected from the group consisting of hydrogen and $C_1$-$C_6$alkyl, in particular methyl;
$R^6$ is $C_1$-$C_{10}$alkyl, in particular i-propyl or n-butyl;
$R^2$ is hydrogen; and
$R^3$ is hydrogen or halo in particular fluoro;

and the pharmaceutically acceptable salts and the solvates thereof.

In another embodiment, the invention provides compounds of Formula (I') as defined herein, wherein Base is selected from the group consisting of (B-1), (B-2) and (B-3a);

$R^1$ is

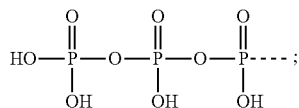

$R^2$ is hydrogen; and $R^3$ is selected from the group consisting of hydrogen, halo in particular fluoro, and $N_3$;

and the pharmaceutically acceptable salts and the solvates thereof.

Of interest are compounds 7, 9, 12, 17, 22, 31 and 45, or 9, 17, 22, 23, 25, 27, 31, 34, 39, 45 or 35 and 58 to 63 mentioned in the section "Examples" as well as the pharmaceutically acceptable acid addition salts of these compounds. Of particular interest are compounds 7, 9, 12, 17, 22, 23, 25, 27, 31, 35, 39, 44, 45, 57 and 58 to 63, either in the free-form (i.e. non-salt form) of these compounds or as a pharmaceutically acceptable acid addition salt thereof.

The compounds of Formula (I), in particular of Formula (I'), have several centers of chirality, in particular at the carbon atoms 1', 2', 3', and 4'. Although the stereochemistry at these carbon atoms is fixed, the compounds may display at least 75%, preferably at least 90%, such as in excess of 95%, or of 98%, enantiomeric purity at each of the chiral centers.

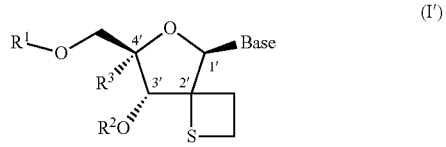

(I')

Chirality may also be present in the substituents, such as where R' is (a-1)

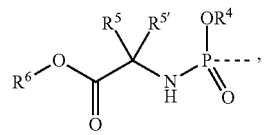

which can have chirality at the $R^5$ bearing carbon (where $R^5$ and $R^{5'}$ are different) and at the phosphorus atom. The phosphorus center can be present as $R_P$ or $S_P$, or a mixture of such stereoisomers, including racemates. Diastereoisomers resulting from the chiral phosphorus center and a chiral carbon atom may exist as well.

The compounds of Formula (I), and in particular of Formula (I'), are represented with defined stereoconfiguration at the 1', 3', 4' and 5' positions, but not at the 2'-position, nor e.g., at the phosphorous atom of the phosphoramidate group when present. The absolute configuration of such compounds can be determined using art-known methods such as, for example, X-ray diffraction or NMR and/or implication from starting materials of known stereochemistry. Pharmaceutical compositions in accordance with the invention will preferably comprise stereoisomerically pure forms of the indicated stereoisomer of the particular compound of Formula (I) or (I').

In a particular embodiment, the compound of Formula (I) as defined herein has the Formula (Ia)

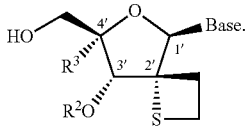

(Ia)

In a particular embodiment, the compound of Formula (I') as defined herein has the Formula (Ia')

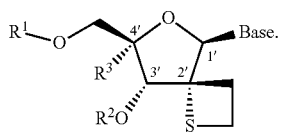

(Ia')

In a particular embodiment, the compounds of the present invention are also intended to include pharmaceutically acceptable salts of the 5'-triphosphate ester as well as pharmaceutically acceptable salts of 5'-diphosphate and 5'-monophosphate ester derivatives of the following structural formulae:

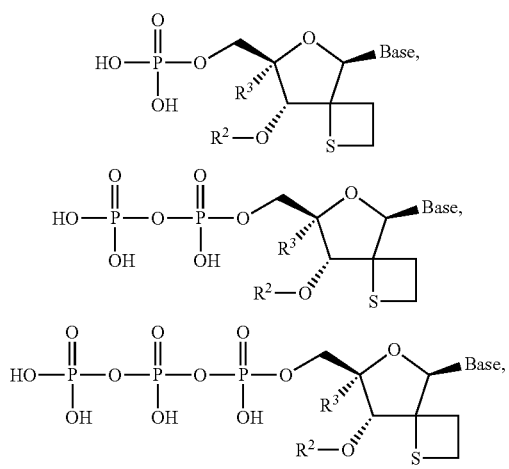

in particular

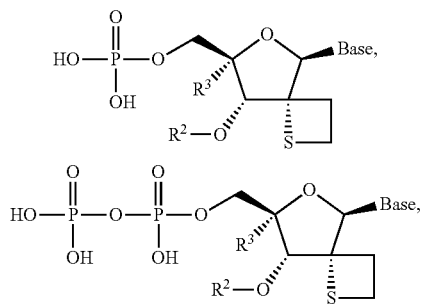

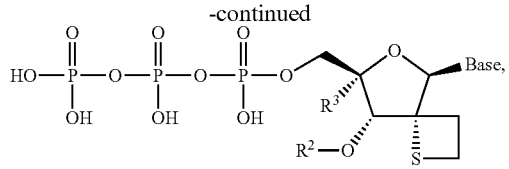

wherein Base, $R^2$ and $R^3$ are as defined herein; and in particular, wherein $R^2$ is hydrogen.

General Synthetic Approaches

Scheme 1

In general, compounds of Formula (I) according to the scope of the present invention, in particular of Formula (I'), wherein R' is a phosphoramidate or a phosphate, herein referred to as compounds of Formula (I'-a1) or (I'-a2), respectively, can be prepared according to the following reaction Scheme 1. In said scheme, all variables are defined as according to the scope of the present invention.

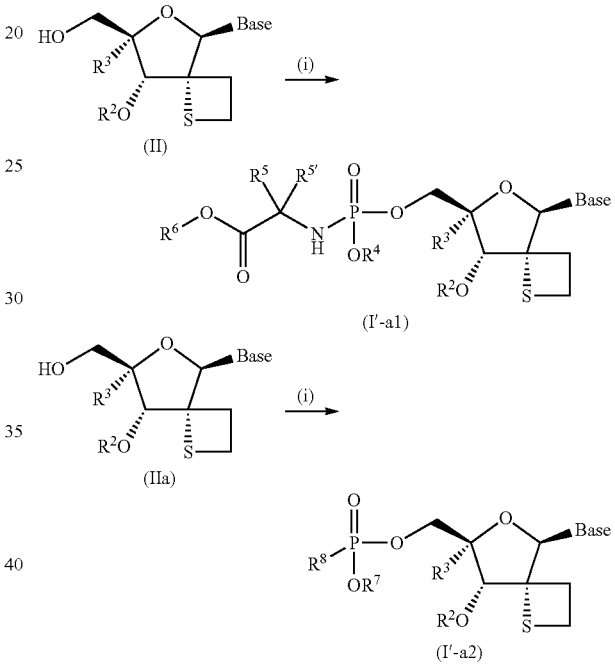

In Scheme 1, the following reaction conditions apply:

(i): pre-treatment with pyridine then concentration and suspension of the resulting product in a suitable solvent, such as for example dry dichloromethane, in the presence of a suitable base, such as for example methyl imidazole, and reacted with a suitable phosphoramidochloridate or phosphorochloridate, at a suitable temperature, such as for example room temperature.

The compound of formula (II) can be for example a deprotected nucleoside, e.g. the compound of formula (1) (Scheme 4), or a protected nucleoside, e.g. the compound of formula (17) (Scheme 4), from which the protecting group can be cleaved after reaction with the appropriate phosphoramidochloridate or phosphorochloridate.

Scheme 2

The phosphoramidochloridate or phosphorochloridate reagents referred to in Scheme 1, are either commercially available or can be synthesized by procedures known to the skilled person, for example, the synthesis of suitable phosphoramidochloridate mentioned in step (i) can be prepared by reacting an alcohol of Formula (III) with $POCl_3$ in the presence of a base, such as DIPEA, to obtain phosphoryl dichloride (IV), which is further reacted with an amino acid of formula (V) to yield the desired phosphoramidochloridate (VI).

SCHEME 3
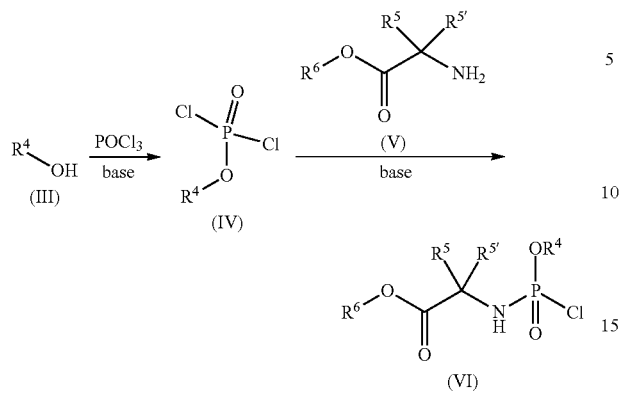
Intermediate compounds of Formula (II) wherein $R^2$ and $R^3$ are hydrogen and Base is uracil, herein referred to as (1), can be prepared according to the following reaction Scheme 3, wherein PMB means p-methoxybenzyl, and Ms means methanesulfonyl.
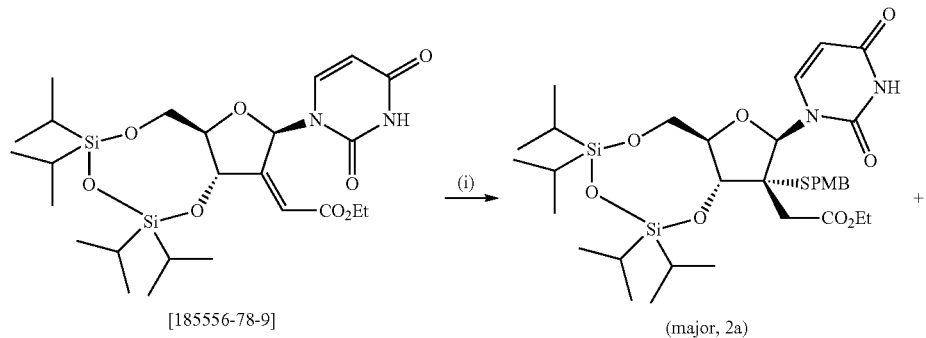
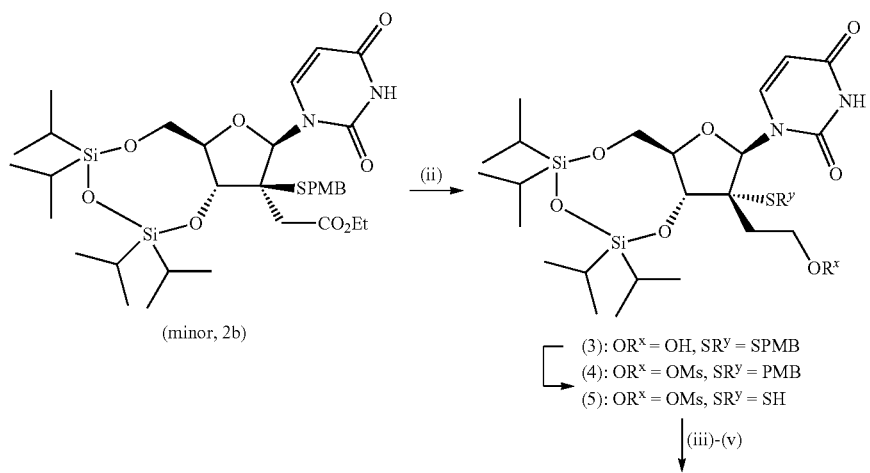

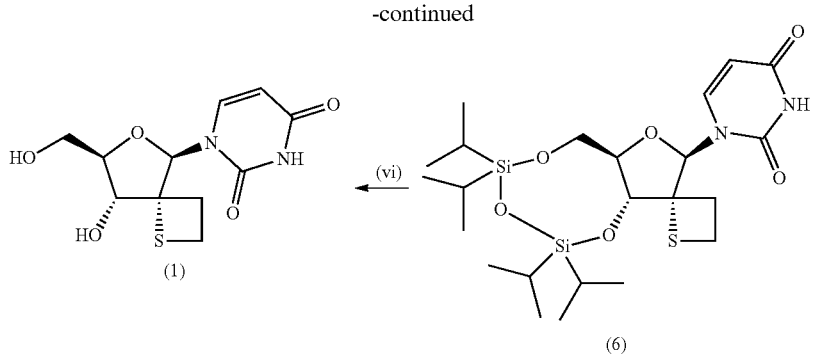

In Scheme 3, the following reaction conditions apply:

(i) (4-methoxyphenyl)methanethiol at a suitable temperature, such as for example room temperature, in a suitable solvent, such as for example THF; mixture cooled to a suitable temperature, such as for example −40° C. in the presence of a suitable base, such as for example KHMDS or NaH; column chromatography (ii) in the presence of a suitable reducing agent, such as for example, lithium aluminium hydride in a suitable solvent, such as for example diethyl ether, at a suitable temperature, such as for example 0° C.;

(iii) under suitable conditions to form a leaving group, such as for example, mesyl, by reaction with a suitable agent, such as methanesulfonyl chloride, in the presence of a suitable base/solvent system, such as for example pyridine, at a suitable temperature, such as for example room temperature;

(iv) under suitable reaction conditions to cleave the PMB protecting group, by reaction with a suitable reagent, such as for example mercury(II) acetate in the presence of a suitable acid, such as for example trifluoroacetic acid, in the presence of a suitable solvent, such as for example phenol, at a suitable temperature, such as for example 0° C.;

(v) in the presence of a suitable base, such as for example sodium hydride, in a suitable solvent, such as tetrahydrofuran, at a suitable temperature, such as at room temperature;

(vi) under suitable conditions to cleave the alcohol protecting group, such as for example, by subjecting the compound of Formula (6) to a source of fluoride, such as for example ammonium fluoride, in a suitable solvent, such as for example methanol, at a suitable temperature, such as for example room temperature, then 50° C. for a sufficient period of time to bring the reaction to completion.

Scheme 4

Alternatively, intermediate compounds of Formula (II) wherein $R^3$ is hydrogen or fluoro, $R^1$ and $R^2$ are hydrogen and the Base is uracil, cytosine or a protected cytosine, such as for example cytosine protected with a dimethoxytrityl protecting group (DMT), herein referred to as compounds of Formulae (11), (18), and (17), can be prepared according to the following reaction Scheme 4.

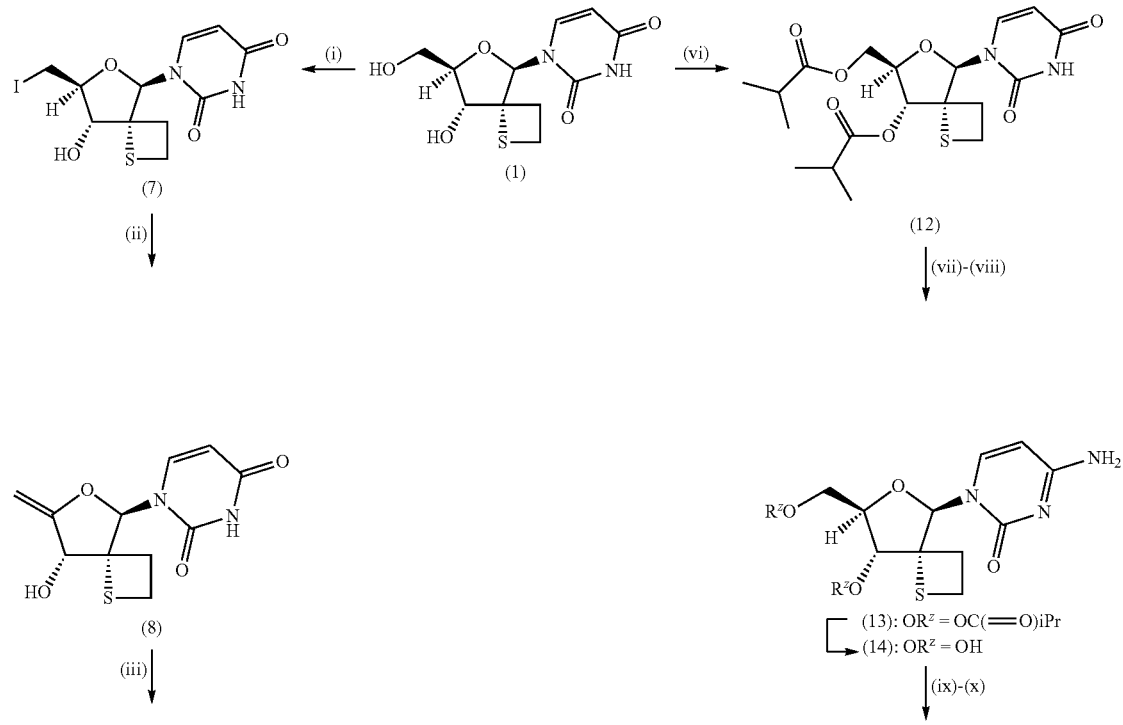

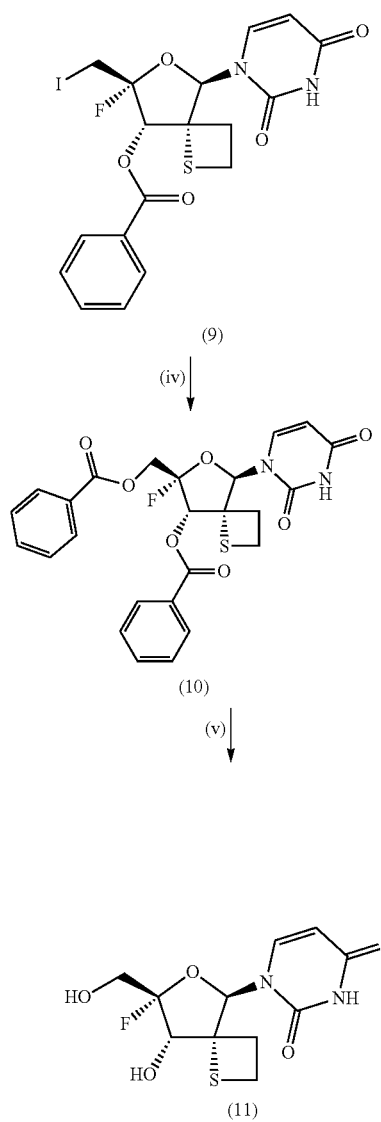

(9)

(10)

(11)

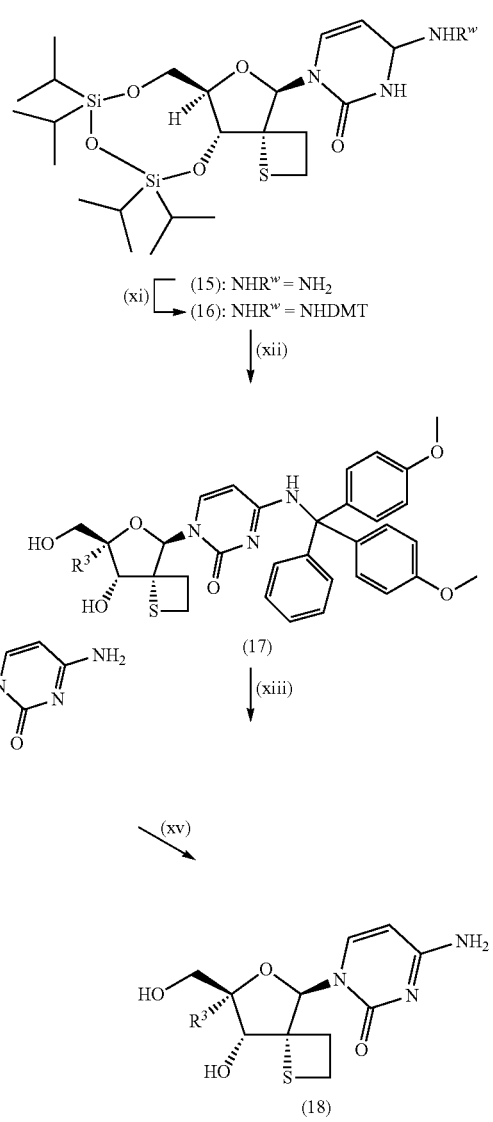

(xi) ┌ (15): NHR^w = NH_2
     └ (16): NHR^w = NHDMT (17)

(19)

(18)

In Scheme 4, the following reaction conditions apply:

(i) at a suitable temperature, such as room temperature, in a suitable solvent, such as tetrahydrofuran, by reaction with iodine in the presence of triphenylphosphine and a suitable base, such as pyridine;

(ii) by reaction with a suitable base, such as for example, sodium methoxide, in a suitable solvent, such as for example methanol, at a suitable temperature, such as at reflux;

(iii) in a suitable solvent, such as for example a mixture of acetonitrile and tetrahydrofuran, at a suitable temperature such as for example −15° C., by reaction with triethylamine trihydrofluoride, followed by N-iodosuccinimide, followed by reaction with benzoyl chloride in the presence of a base such as for example triethylamine in the presence of a catalyst such as 4-(dimethylamino)pyridine at a suitable temperature, such as 0° C., followed by room temperature;

(iv) at a suitable temperature such as for example 120° C., in a suitable solvent such as dimethylformamide, by reaction with sodium benzoate in the presence of a complexing agent, such as for example 15-crown-5;

(v) under suitable conditions to cleave the alcohol protecting group, such as for example, by subjecting the compound of Formula (10) to ammonia, in a suitable solvent, such as for example methanol, at a suitable temperature, such as for example room temperature;

(vi) under suitable conditions to form a protected alcohol, such as for example, by reaction with isobutyric anhydride, in the presence of a suitable base such as for example pyridine, in a suitable solvent, such as for example toluene, at a suitable temperature, such as for example 0° C. and subsequently allowing to reach room temperature;

(vii)-(viii): at a suitable temperature, such as for example room temperature, by reaction with a suitable reagent, such as for example 2,4,6-triisopropylbenzenesulfonyl chloride, in the presence of a suitable base such as triethylamine and a catalyst such as 4-(dimethylamine)pyridine, followed by reaction with ammonia;

(ix) under suitable conditions to cleave the alcohol protecting group, such as for example, by subjecting the compound of Formula (10) to ammonia, in a suitable solvent, such as for example methanol, at a suitable temperature, such as for example room temperature;

(x): at a suitable temperature, such as for example, at room temperature, by reaction with 1,3-dichloro-1,1,3,3- tetraisopropyldisiloxane in the presence of a base, such as for example triethylamine in the presence of a catalyst, such as for example 4-(dimethylamino)pyridine, in a suitable solvent, such as for example dichloromethane, for a period of time sufficient to bring the reaction to completion; followed by reaction with ammonia, stirring vigorously;

(xi): at a suitable temperature, such as for example room temperature, by reaction with a protecting group agent, such as for example 4,4'-(chloro(phenyl)methylene)bis(methoxybenzene) in an suitable solvent, such as for example dichloromethane, in the presence of silver nitrate and 2,3,5-trimethylpyridine;

(xii): under suitable conditions to cleave the alcohol protecting group, such as for example, by subjecting the compound of Formula (16) to a source of fluoride, such as for example TBAF, in a suitable solvent, such as for example tetrahydrofuran, at a suitable temperature, such as for example room temperature, for a sufficient period of time to bring the reaction to completion;

(xiii): under suitable conditions to cleave the amino protecting group, such as for example, by subjecting the compound of Formula (17) to an acid, such as for example trifluoroacetic acid, in a suitable solvent, such as for example, in dichloromethane, at a suitable temperature, such as for example room temperature;

(xiv): at a suitable temperature, such as for example room temperature, by reaction with a suitable reagent, such as for example 2,4,6-triisopropylbenzenesulfonyl chloride, in the presence of a suitable base such as triethylamine and a catalyst such as 4-(dimethylamine)pyridine, followed by reaction with ammonia;

(xv): under suitable conditions to cleave the alcohol protecting group, such as for example, by subjecting the compound of Formula (19) to ammonia, in a suitable solvent, such as for example methanol, at a suitable temperature, such as for example room temperature.

Scheme 5

Alternatively, intermediate compounds of Formula (II) wherein $R^3$ is azide, and the Base is uracil, herein referred to as a compound of Formula (22), wherein PG and PG' represent suitable alcohol protecting groups, such as for example benzoyl, can be prepared according to the following reaction Scheme 5.

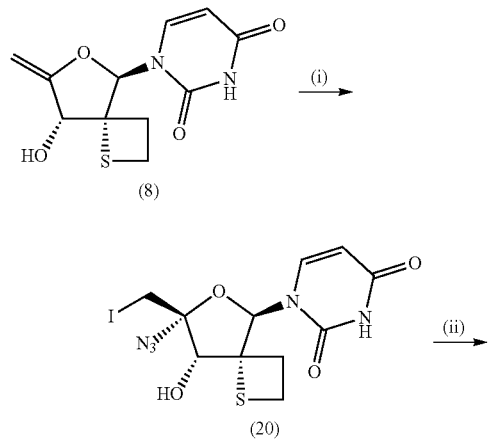

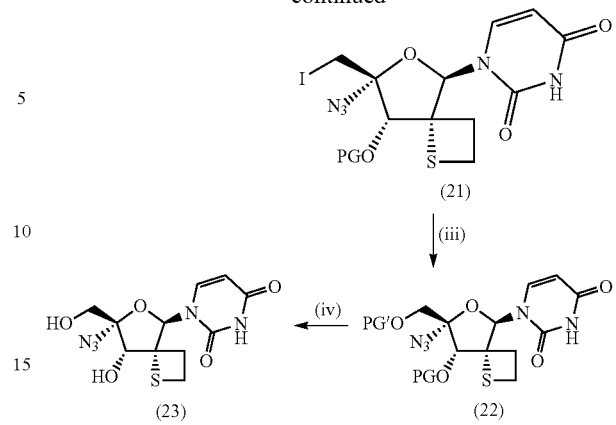

In Scheme 5, the following reaction conditions apply:

(i) at a suitable temperature, such as room temperature, in a suitable solvent, such as THF, by reaction with sodium azide in the presence of N-benzyl-N,N-diethylethanaminium chloride and NMM for a sufficient period of time to bring the reaction to completion, followed by addition of iodine in a suitable solvent, such as tetrahydrofuran, at a suitable temperature, such as room temperature, for a sufficient period of time, such as approximately 5 h, followed by addition of N-acetyl-cysteine until no gas evolution was observed, and saturated aqueous $Na_2S_2O_3$.

(ii) under suitable conditions to form a protected alcohol, such as for example, by reaction with benzoyl chloride, in the presence of a suitable base such as for example $Et_3N$, and a catalyst such as DMP, in a suitable solvent, such as for example THF, at a suitable temperature, such as for example 0° C. and subsequently allowing to reach room temperature;

(iii) under suitable conditions to form a protected alcohol, such as for example, by reaction with sodium benzoate, in the presence of a complexing agent such as 15-crown-5, in a suitable solvent, such as for example DMF, at a suitable temperature, such as for example 120° C. for a sufficient period of time to bring the reaction to completion, for example 12 h.

(iv) under suitable conditions to cleave the alcohol protecting group, such as for example, by subjecting the compound of Formula (22) to ammonia, in a suitable solvent, such as for example methanol, at a suitable temperature, such as for example room temperature.

Compound 22 can be then subjected to further functional group interconversion into a nucleoside bearing different base, for example, following procedures analogous to those described in Scheme 4 hereinabove.

Scheme 6

Compounds of Formula (I) or (I') wherein $R^1$ and $R^2$ are bound to form a cyclic phosphate or phosphoramidate type group or derivative thereof, herein referred to as a compound of Formula (I'-a3), can be prepared according to the following reaction Scheme 6.

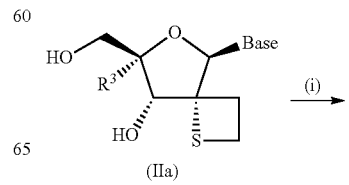

33

-continued

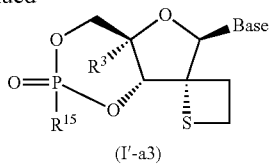

(I'-a3)

In Scheme 6, the following reaction conditions apply:

(i) pre-treatment with pyridine then concentration and treatment of the resulting product with an appropriate phosphorochloridate or phosphoramidochloridate, at a suitable temperature, such as room temperature, in a suitable solvent, such as DCM, by reaction with N-methylimidazole for a sufficient period of time to bring the reaction to completion, followed by treatment with a suitable base, such as tBuOK in the presence of a suitable solvent such as for example THF, at a suitable temperature, such as for example room temperature, for a sufficient period of time to bring the reaction to completion.

The phosphorochloridate or phosphoramidochloridate reagents are either commercially available or can be synthesized according to procedures known to the skilled person.

Scheme 7

Alternatively, intermediate compounds of Formula (II) wherein $R^2, R^3$ are hydrogen and the Base is guanine, herein referred to as a compound of Formula (24), can be prepared according to the following reaction Scheme 7.

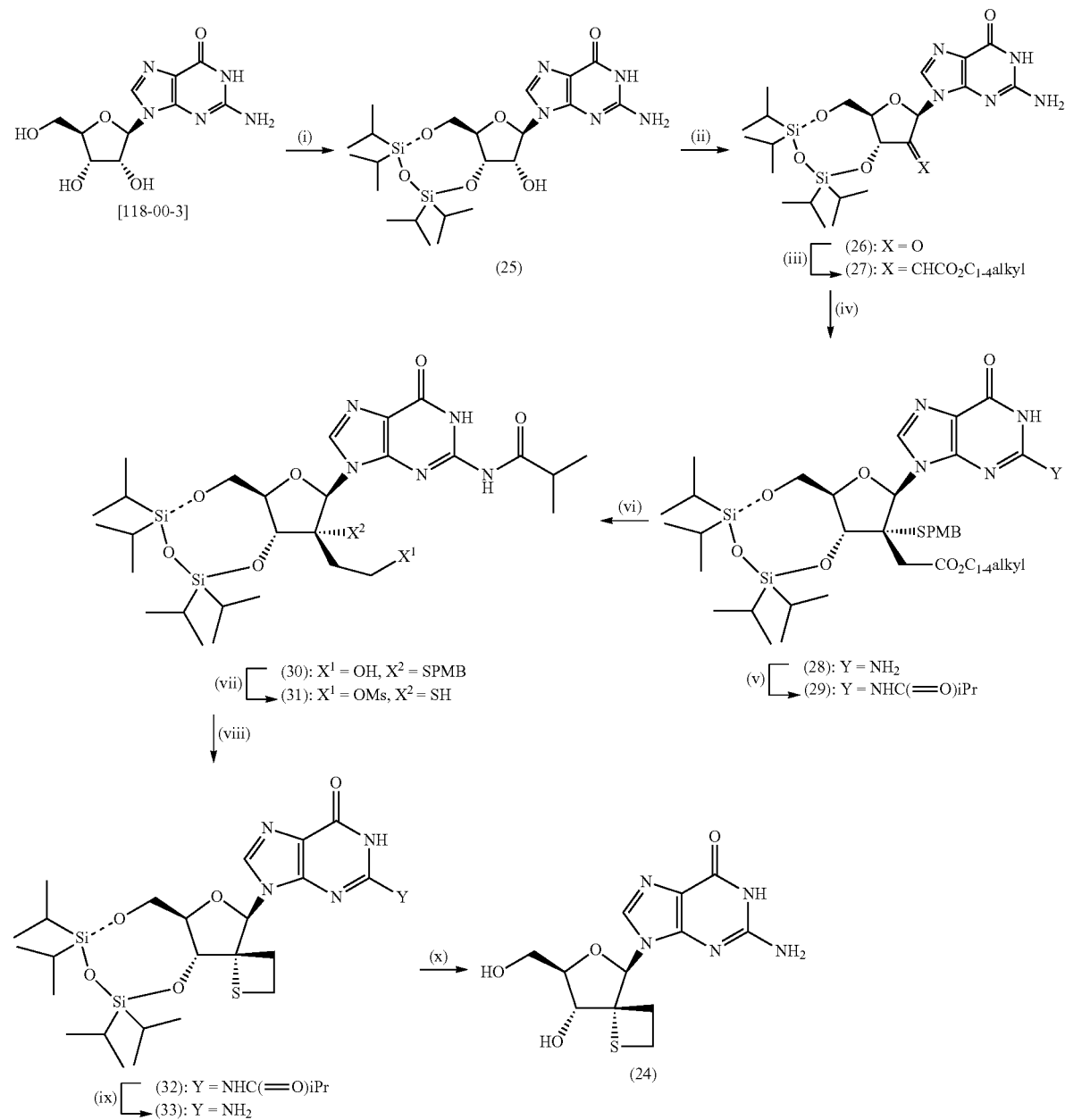

In Scheme 7, the following reaction conditions apply:

(i) at a suitable temperature, such as for example, at room temperature, by reaction of guanosine with 1,3-dichloro-1,1,3,3-tetraisopropyldisiloxane in the presence of a base, such as for example imidazole, in a suitable solvent, such as for example DMF, for a period of time sufficient to bring the reaction to completion;

(ii) at a suitable temperature, such as for example, at 0° C., in a suitable solvent, such as DCM, by reaction with Dess Martin Periodinane;

(iii) at a suitable temperature, such as at room temperature, in a suitable solvent such as 20° C., by reaction with a suitable alkyl triphenylphosphanylideneacetate;

(iv) by reaction with (4-methoxyphenyl)methanethiol at a suitable temperature, such as for example room temperature, in a suitable solvent, such as for example THF, then cooled to a suitable temperature, such as for example −40° C. in the presence of a suitable base, such as for example KHMDS;

(v) in a suitable solvent, such as pyridine, at a suitable temperature, such as at room temperature, by reaction with isobutyric anhydride followed by addition of TEA and subsequently raising the temperature for example, to 80° C. for a sufficient time to allow completion of the reaction;

(vi) in the presence of a suitable reducing agent, such as for example, lithium aluminium hydride in a suitable solvent, such as for example THF, at a suitable temperature, such as for example 0° C. followed by room temperature;

(vii) under suitable conditions to form a leaving group, such as for example, mesyl, by reaction with a suitable agent, such as methanesulfonyl chloride, in the presence of a suitable base/solvent system, such as for example pyridine, at a suitable temperature, such as for example room temperature;

(viii) under suitable reaction conditions to cleave the PMB protecting group, by reaction with a suitable reagent, such as for example mercury(II) acetate in the presence of a suitable acid, used as solvent such as for example trifluoroacetic acid, in the presence of an excess of phenol, at a suitable temperature, such as for example 0° C., followed by addition of 1,4-dimercaptobutane-2,3-diol at 0° C.;

(ix) in the presence of a suitable base, such as for example sodium hydride, in a suitable solvent, such as tetrahydrofuran, at a suitable temperature, such as at room temperature;

(x) under suitable conditions to cleave the amino protecting group, such as for example, by treating the compound of Formula (32) with ammonia, in a suitable solvent, such as for example methanol, at a suitable temperature, such as for example room temperature;

(xi) under suitable conditions to cleave the alcohol protecting group, such as for example, by subjecting the compound of Formula (33) to a source of fluoride, such as for example ammonium fluoride, in a suitable solvent, such as for example methanol, at a suitable temperature, such as for example room temperature, then 50° C. for a sufficient period of time to bring the reaction to completion.

Scheme 8

Alternatively, intermediate compounds of Formula (II) wherein $R^2$, $R^3$ are hydrogen and the Base is Adenine, herein referred to as a compound of Formula (42), can be prepared per the following reaction Scheme 8.

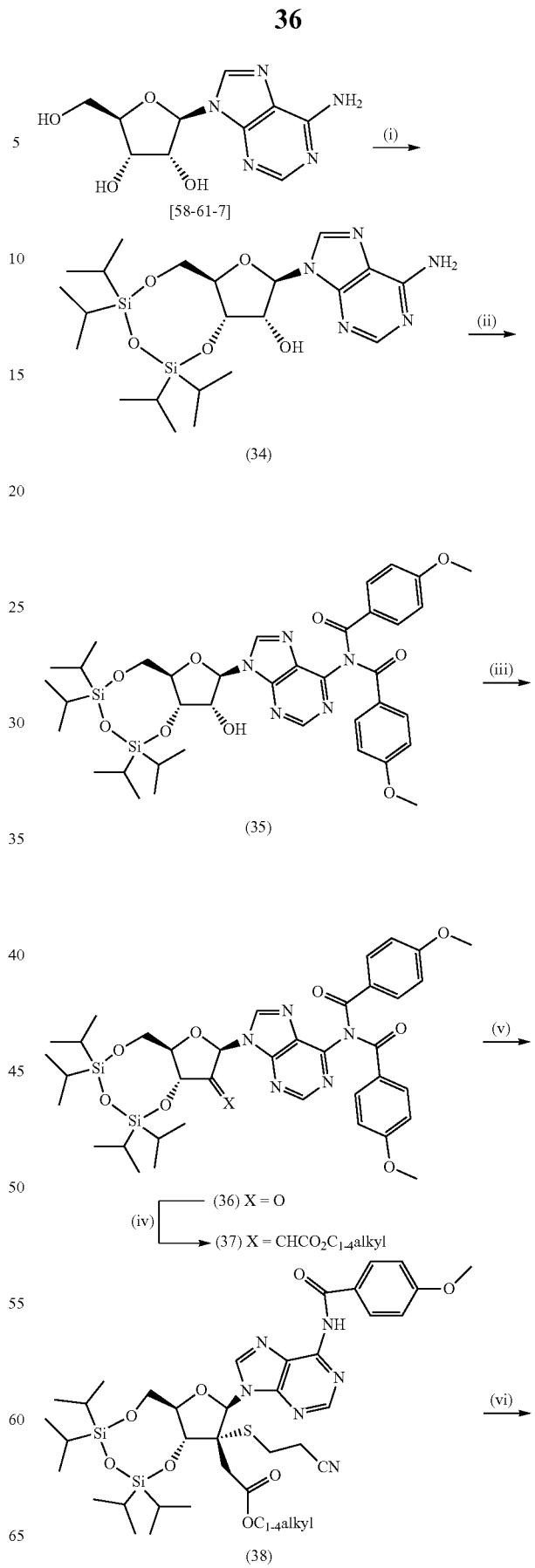

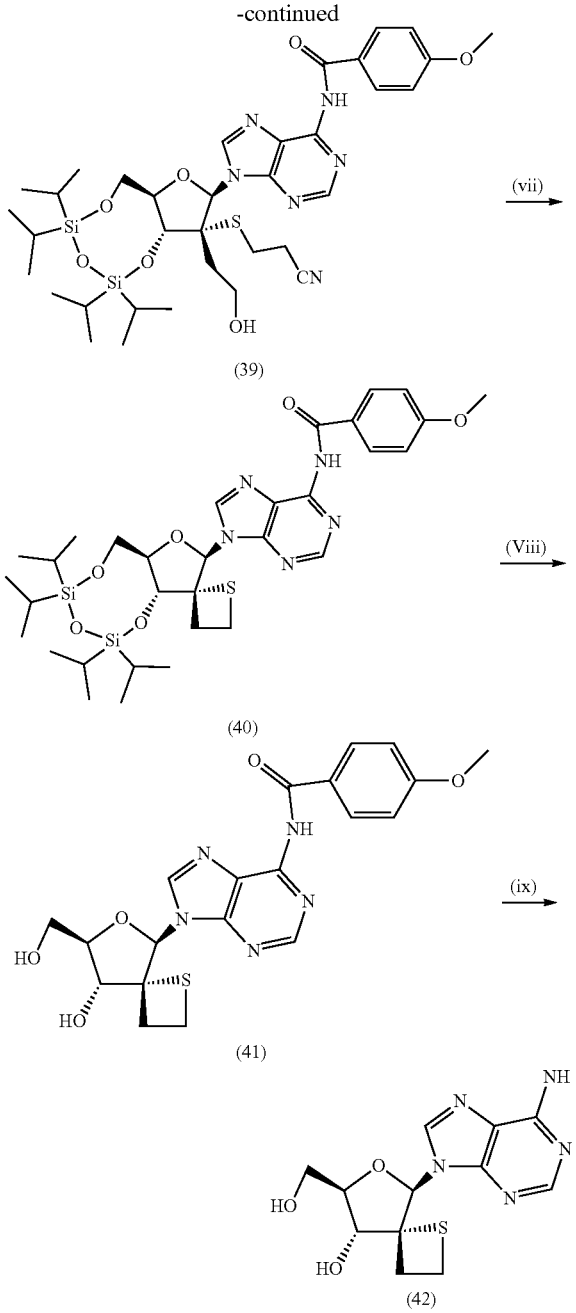

In Scheme 8, the following reaction conditions apply:
(i) at a suitable temperature, such as for example, at room temperature, by reaction of adenosine with 1,3-dichloro-1,1,3,3-tetraisopropyldisiloxane in the presence of a base, such as for example imidazole, in a suitable solvent, such as for example DMF, for a period sufficient to bring the reaction to completion;
(ii) using a suitable oxygen protecting group such as TMS at a suitable temperature such as room temperature in a suitable solvent such as pyridine, amine group was protected using a suitable protecting group such as paramethoxybenzoyl group.
(iii) at a suitable temperature, such as for example, at 0° C., in a suitable solvent, such as DCM, by reaction with Dess Martin Periodinane;
(iv) at a suitable temperature, such as at room temperature, in a suitable solvent such as 20° C., by reaction with a suitable alkyl triphenylphosphanylideneacetate;
(v) by reaction with 3-mercaptopropanenitrile at a suitable temperature, such as for example room temperature, in a suitable solvent, such as for example THF, then cooled to a suitable temperature, such as for example 0° C. in the presence of a suitable base, such as for example NaH;
(vi) in the presence of a suitable reducing agent, such as for example, lithium aluminum hydride in a suitable solvent, such as for example THF, at a suitable temperature, such as for example −60° C.;
(vii) under suitable conditions to form a leaving group, such as for example, mesyl, by reaction with a suitable agent, such as methanesulfonyl chloride, in the presence of a suitable base/solvent system, such as for example pyridine, at a suitable temperature, such as for example room temperature; then in the presence of a suitable base, such as for example potassium terbutoxide, in a suitable solvent, such as tetrahydrofuran, at a suitable temperature, such as at −78° C.;
(viii) under suitable conditions to cleave the alcohol protecting group, such as for example, by subjecting the compound of Formula (40) to a source of fluoride, such as for example ammonium fluoride, in a suitable solvent, such as for example methanol, at a suitable temperature, such as for example room temperature for a sufficient period to bring the reaction to completion.
(ix) under suitable conditions to cleave the amino protecting group, such as for example, by treating the compound of Formula (41) with ammonia, in a suitable solvent, such as for example methanol, at a suitable temperature, such as for example 70° C.;

Pharmacology

It has been found that the compounds of the present invention show activity against Flaviviridae and/or alphaviruses, in particular HCV, Dengue and/or chikungunya viruses and/or Sindbis viruses and/or Simliki Forest viruses.

Therefore, in one embodiment, the invention provides compounds of Formula (I) and the phosphates and the prodrugs thereof, and the pharmaceutically acceptable salts and solvates thereof, for use in the treatment or prevention (or the manufacture of a medicament for the treatment or prevention) of HCV infection. The latter include progressive liver fibrosis, inflammation and necrosis leading to cirrhosis, end-stage liver disease, and HCC.

The in vitro antiviral activity against HCV of the compounds of Formula (I) can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

In a further embodiment, the invention provides compounds of Formula (I) and the phosphates and the prodrugs thereof, and the pharmaceutically acceptable salts and solvates thereof, for use in the treatment or prevention (or the manufacture of a medicament for the treatment or prevention) of Dengue viral infection.

In yet another embodiment, the invention provides compounds of Formula (I) and the phosphates and the prodrugs thereof, and the pharmaceutically acceptable salts and solvates thereof, for use in the treatment or prevention (or the manufacture of a medicament for the treatment or prevention) of Chikungunya and/or Sindbis and/or Simliki Forest viral infection.

Due to their anti-viral properties, the compounds of Formula (I), including any possible stereoisomers, and the phosphates and the prodrugs thereof, and the pharmaceutically acceptable salts and solvates thereof, can be useful in the treatment of warm-blooded animals, in particular humans, infected with Flaviviridae and/or alphaviruses, and in the prevention of Flaviviridae and/or alphavirus infections. The compounds of the present invention may therefore be used as a medicine, in particular as a Flaviviridae and/or alphavirus anti-viral or viral-inhibiting medicine. The present invention also relates to the use of the present compounds in the manufacture of a medicament for the treatment or the prevention of a Flaviviridae and/or alphavirus infection. In a further aspect, the present invention relates to a method of treating a warm-blooded animal, in particular a human, infected by Flaviviridae and/or alphavirus, or being at risk of becoming infected by Flaviviridae and/or alphavirus, said method comprising the administration of an anti-Flaviviridae and/or anti-alphavirus effective amount of a compound of Formula (I), as specified herein. Said use as a medicine or method of treatment comprises the systemic administration to Flaviviridae and/or alphavirus-infected subjects or to subjects susceptible to Flaviviridae and/or alphavirus infection of an amount effective to combat the conditions associated with Flaviviridae and/or alphavirus infection.

In a particular embodiment, the Flavivirus is selected from hepatitis C virus and Dengue virus. In a further embodiment, the Flavivirus is hepatitis C virus. In another embodiment, the Flavivirus is Dengue virus. In another embodiment, the alphavirus is selected from Chikungunya virus and Sindbis virus and Simliki Forest virus, in particular, Chikungunya virus.

In a further aspect, the present invention concerns a pharmaceutical composition comprising a therapeutically effective amount, in particular an anti-virally effective amount, of a compound of Formula (I) as specified herein, and a pharmaceutically acceptable carrier. Said composition may contain from 1% to 50%, or from 10% to 40% of a compound of Formula (I) and the remainder of the composition is the said carrier. A therapeutically effective amount, in particular an anti-virally effective amount, in this context is an amount sufficient to act in a prophylactic way against the Flavivirus and/or alphavirus infection, to inhibit the Flavivirus and/or alphavirus, to stabilize or to reduce the Flavivirus and/or alphavirus infection, in infected subjects or subjects being at risk of becoming infected. In still a further aspect, this invention relates to a process of preparing a pharmaceutical composition as specified herein, which comprises intimately mixing a pharmaceutically acceptable carrier with a therapeutically effective amount, in particular an anti-virally effective amount, of a compound of Formula (I), as specified herein.

The compounds of Formula (I) or of any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In general it is contemplated that an antiviral effective daily amount would be from about 1 to about 200 mg/kg, or about 5 to about 175 mg/kg, or about 10 to about 150 mg/kg, or about 20 to about 100 mg/kg, or about 50 to about 75 mg/kg body weight. Average daily doses can be obtained by multiplying these daily amounts by about 70. It may be appropriate to administer the required dose as two, three, four or more sub-doses at appropriate intervals throughout the day. Said sub-doses may be formulated as unit dosage forms, for example, containing about 1 to about 5000 mg, or about 50 to about 3000 mg, or about 100 to about 1000 mg, or about 200 to about 600 mg, or about 100 to about 400 mg of active ingredient per unit dosage form.

EXAMPLES

Several methods for preparing the compounds of this invention are illustrated in the following examples. Unless otherwise noted, all starting materials were obtained from commercial suppliers and used without further purification.

Hereinafter, the term "KHMDS" means potassium hexamethyldisilazide, "THF" means tetrahydrofuran, "EA" or "EtOAc" means ethyl acetate, "PE" means petroleum ether, "TFA" means trifluoroacetic acid, "MeOH" means methanol, "TIPSCl" means triisopropylsilyl chloride, "DCM" means dichloromethane, "TBAF" means tetrabutylammonium fluoride, "prep" means preparative, "HPLC" means high performance liquid chromatography, "TPP" means triphenylphosphine, "NMI" means N-methylimidazole, "NaOMe" means sodium methoxide, "CAN" or "MeCN" means acetonitrile, "NIS" means N-iodosuccinimide, "DMAP" means 4-dimethylaminopyridine, "TPSCl" means 2,4,6-triisopropylbenzenesulfonyl chloride, "DIPEA" means N,N-diisopropylethylamine, "DBU" means 1,8-diazabicycl[5.4.0]undec-7-ene, "NMM" means 4-methylmorpholine, "MS" means mass spectrometry, "ES" means electrospray, "DMSO" means dimethylsulfoxide, "DMP" means Dess-Martin periodinane, "TEA" means trimethylamine, "RT" means room temperature, "LC-MS" means liquid chromatography-mass spectrometry, "MsCl" means methanesulfonyl (or mesyl) chloride.

LC-MS analysis was done using either one of the following methods. NMR data were recorded on a Bruker 400 MHz spectrometer.

Purification by preparatory HPLC was performed according to the following methods:

Method A: Stationary phase: Uptisphere C18 ODB-10 μm, 200 g, 5 cm; Mobile phase: 0.25% $NH_4HCO_3$ solution in water, $CH_3CN$ Method B: Stationary phase: RP XBridge Prep C18 OBD-10 μm, 30×150 mm; Mobile phase: 0.25% $NH_4HCO_3$ solution in water, $CH_3CN$ Method C: Stationary phase: RP SunFire Prep C18 OBD-10 μm, 30×150 mm; Mobile phase: 0.25% $NH_4HCO_3$ solution in water, $CH_3CN$ Method D: Stationary phase: RP XBridge Prep $C_{18}$ ODB-5 μm, 30×250 mm; Mobile phase: 0.25% $NH_4HCO_3$ solution in water, MeOH The following schemes are just meant to be illustrative and are by no means limiting the scope.

Scheme 1: Synthesis of 1-((4R,5R,7R,8R)-8-hydroxy-7-(hydroxymethyl)-6-oxa-1-thiaspiro[3.4] octan-5-yl)pyrimidine-2,4(1H,3H)-dione 7

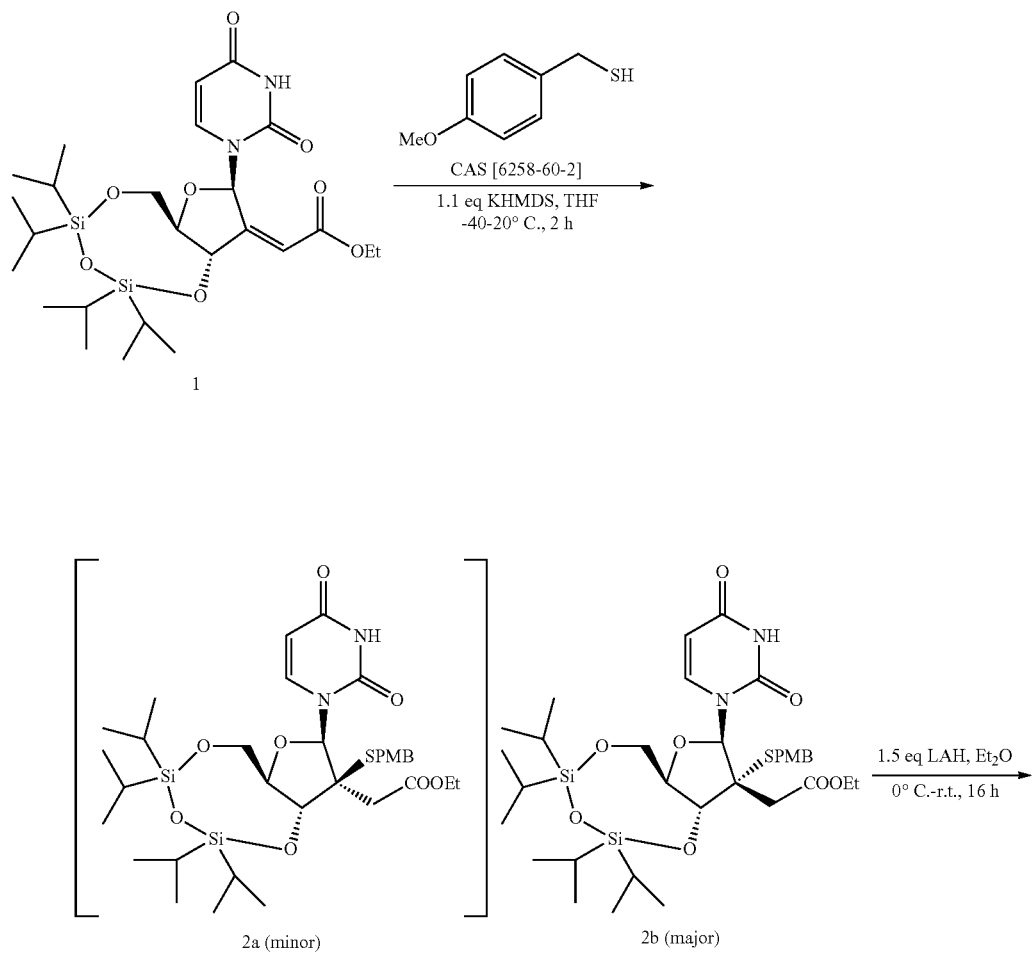

-continued
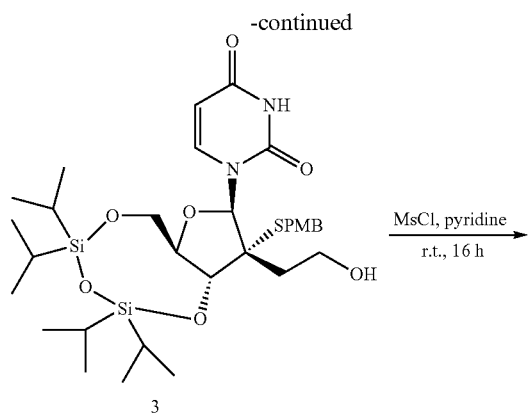
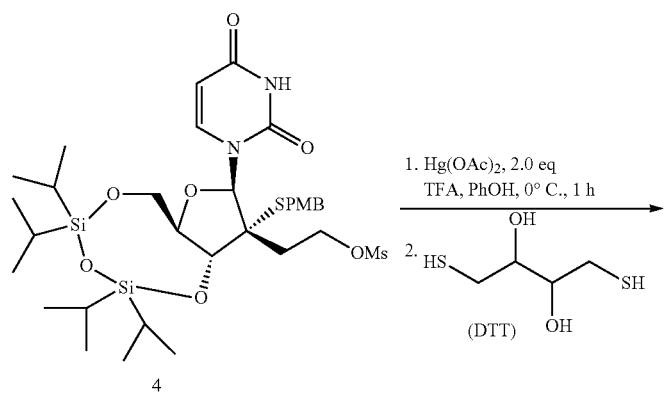
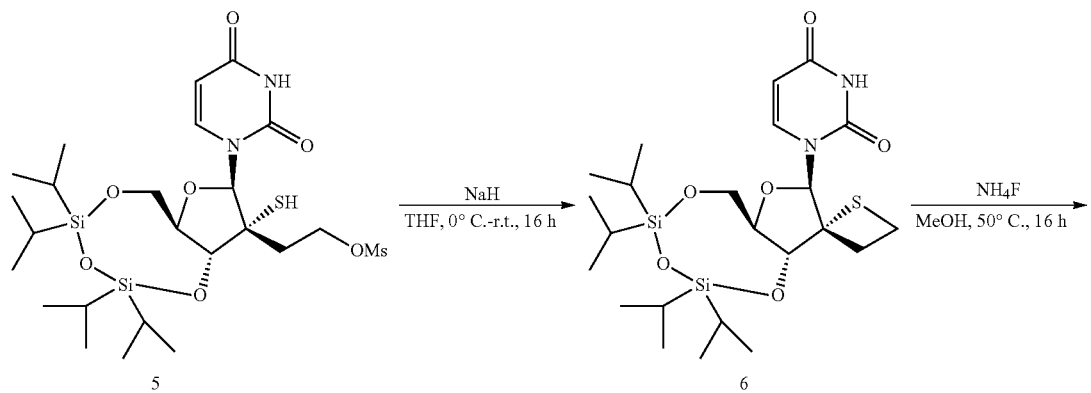
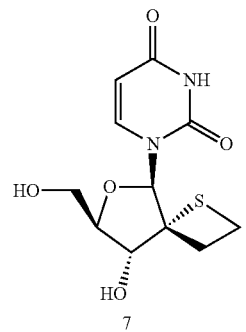

Step 1: Synthesis of ethyl 2-((6aR,8R,9R,9aR)-8-(2,4-dioxo-3,4-dihydropyrimidin-1(2H)-yl)-2,2,4,4-tetraisopropyl-9-(4-methoxybenzyl)thio)tetrahydro-6H-furo[3,2-f][1,3,5,2,4]trioxadisilocin-9-yl)acetate 2b (4-Methoxyphenyl)methanethiol CAS[258-60-22] (69.4 g, 450.6 mmol) in THF (5 L) was stirred at 20° C. under nitrogen. The mixture was cooled to −40° C. then KHMDS (1 M, 495.7 mL, 495.7 mmol) was added dropwise. The resulting white viscous liquid was stirred for 30 min then intermediate 1 (250 g, 450.6 mmol) in THF (1 L) was added at −40° C. The reaction mixture was allowed to warm slowly to 20° C. and stirred for 2 h. The reaction mixture was quenched by addition of aqueous solution 1 N of HCl (2 L) then extracted with EtOAc (2×2 L). The organic layer was successively washed with aqueous solution of sodium bicarbonate (2 L), brine (2 L), dried over $Na_2SO_4$ and evaporated. The resulting residue was purified by column chromatography (PE/EA=20/1 to 3/1) to yield compound 2b (159 g, 50%) as colorless oil.

m/z=710 (M+H)$^{-1}$; $^1$H NMR: (400 MHz, CDCl$_3$): δ 8.26 (s, 1H), 7.82 (d, J=8.0 Hz, 1H), 7.29 (d, J=8.4 Hz, 2H), 6.85 (d, J=8.4 Hz, 2H), 6.28 (s, 1H), 5.66-5.63 (m, 1H), 5.34-5.30 (m, 1H), 4.41-4.23 (m, 1H), 4.19-4.04 (m, 5H), 3.80-3.78 (m, 4H), 3.23-3.19 (m, 1H), 2.92 (d, J=16.4 Hz, 1H), 1.30-0.86 (m, 51H).

Step 2: Synthesis of 1-((6aR,8R,9R,9aR)-9-(2-hydroxyethyl)-2,2,4,4-tetraisopropyl-9-((4-methoxybenzyl)thio)tetrahydro-6H-furo[3,2-f][1,3,5,2,4]trioxadisilocin-8-yl)pyrimidine-2,4(1H,3H)-dione 3

Lithium aluminium hydride (4 g, 105 mml) was suspended in diethyl ether (1.5 L) under nitrogen at 0° C. then intermediate 2b (50 g, 70 mmol) in ether (200 mL) was added slowly at 0° C. The resulting white turbid solution was stirred at 20° C. for 16 h. The reaction mixture was quenched by addition of aqueous solution 1 N of HCl (1 L) then extracted with EtOAc (2×1 L). The organic layer was dried over $Na_2SO_4$ and evaporated. The resulting residue was purified by column chromatography (PE/EA=10/1 to 1/1) to yield compound 3 (27.8 g, 60%) as colorless oil.

m/z=668 (M+H)$^+$; $^1$H NMR: (400 MHz, CDCl$_3$): δ 8.78 (s, 1H), 7.89 (d, J=8 Hz, 1H), 7.30 (d, J=8.4 Hz, 2H), 6.85 (d, J=8.8 Hz, 2H), 6.35 (s, 1H), 5.73 (d, J=8 Hz, 1H), 4.36-3.91 (m, 12H), 3.79 (s, 3H), 2.23-2.20 (m, 2H), 1.78-1.73 (m, 1H), 1.11-0.97 (m, 30H).

Step 3: Synthesis of 2-((6aR,8R,9R,9aR)-8-(2,4-dioxo-3,4-dihydropyrimidin-1(2H)-yl)-2,2,4,4-tetraisopropyl-9-((4-methoxybenzyl)thio)tetrahydro-6H-furo[3,2-f][1,3,5,2,4]trioxadisilocin-9-yl)ethyl methanesulfonate 4

Intermediate 3 (50 g, 75 mmol) was dissolved in pyridine (500 mL) under nitrogen at 25° C., then mesylchloride (12.8 g, 112.5 mmol) was slowly added at 25° C. The resulting yellow solution was stirred at 25° C. for 16 h. The reaction mixture was quenched by addition of aqueous solution 1 N of HCl (1 L) then extracted with EtOAc (2×1 L). The organic layer was dried over $Na_2SO_4$ and evaporated. The resulting residue was purified by column chromatography (PE/EA=10/1 to 1/1) to yield compound 4 (43 g, 78%) as colorless oil.

m/z=746 (M+H)$^+$ $^1$H NMR: (400 MHz, CDCl$_3$): δ 8.56 (s, 1H), 7.92 (d, J=8.4 Hz, 1H), 7.31 (d, J=8.8 Hz, 2H), 6.87-6.85 (m, 2H), 6.27 (s, 1H), 5.77-5.74 (m, 1H), 4.55-4.53 (m, 2H), 4.38-4.02 (m, 8H), 3.79 (s, 3H), 2.95 (s, 3H), 2.28-2.21 (m, 1H), 1.12-1.01 (m, 31H).

Step 4: Synthesis of 2-((6aR,8R,9R,9aR)-8-(2,4-dioxo-3,4-dihydropyrimidin-1(2H)-yl)-2,2,4,4-tetraisopropyl-9-mercaptotetrahydro-6H-furo[3,2-f][1,3,5,2,4]trioxadisilocin-9-yl)ethyl methanesulfonate 5

To intermediate 4 (62 g, 83.2 mmol) in TFA (250 mL) at 25° C., mercury acetate (53 g, 166.4 mmol) and phenol (39.1 g, 416 mmol) were added slowly at 0° C. The resulting dark red solution was stirred at 0° C. for 1 h. The 1,4-dimercaptobutane-2,3-diol (25.6 g, 166.4 mmol) was added at 0° C. The resulting mixture was stirred 10 min then filtered over Celite® and washed with ethylacetate (1 L). The pH was adjusted to 7 by addition of an aqueous solution of sodium bicarbonate. The resulting mixture was filtered over Celite® and extracted with EtOAc (2×1 L). The organic layer was dried over $Na_2SO_4$ and evaporated at 25° C. to give intermediate 5 (64 g, crude) as brown oil.

Step 5: Synthesis of 1-((2'R,6aR,8R,9aR)-2,2,4,4-tetraisopropyltetrahydrospiro[furo[3,2-f][1,3,5,2,4]trioxadisilocine-9,2'-thietan]-8-yl)pyrimidine-2,4(1H,3H)-dione 6

Intermediate 5 (57 g, 91 mmol) was dissolved in THF (500 mL) at 20° C. under nitrogen. The resulting mixture was stirred at 0° C. then sodium hydride (3.6 g, 135 mmol) was added slowly. The reaction mixture was stirred at 20° C. for 16 h. The reaction mixture was quenched by addition of aqueous solution 1 N of HCl (1 L) then extracted with EtOAc (2×1 L). The organic layer was dried over $Na_2SO_4$ and evaporated. The resulting residue was purified by column chromatography (PE/EA=10/1 to 5/1) to yield compound 6 (18.3 g, 46%, 2 steps) as colorless oil.

m/z=529 (M+H)$^+$ $^1$H NMR: (400 MHz, CDCl$_3$): δ 8.55 (s, 1H), 7.93 (d, J=8 Hz, 1H), 6.58 (s, 1H), 5.69 (d, J=8 Hz, 1H), 4.20-4.17 (m, 1H), 4.05-3.96 (m, 2H), 3.54-3.51 (m, 1H), 3.33-3.32 (m, 1H), 2.96-2.87 (m, 2H), 2.85-2.69 (m, 1H), 1.17-0.98 (m, 30H).

Step 6: Synthesis of 1-((4R,5R,7R,8R)-8-hydroxy-7-(hydroxymethyl)-6-oxa-1-thiaspiro[3.4]octan-5-yl)pyrimidine-2,4(1H,3H)-dione 7

Intermediate 6 (50 g, 94.5 mmol) was dissolved in methanol (500 mL) at 20° C. under nitrogen. Ammonium fluoride (10.5 g, 283.6 mmol) was added at 20° C. The reaction mixture was stirred at 50° C. for 16 h. The reaction mixture was allowed to cool down to RT then the solvent was removed under reduced pressure. The resulting residue was purified by column chromatography (DCM/MeOH: 100/1 to 10/1) to yield (11.2 g, 42%) of 7 as white solid.

m/z=287 (M+H)$^+$ $^1$H NMR: (400 MHz, DMSO-d$_6$): δ 8.00 (d, J=8 Hz, 1H), 6.39 (s, 1H), 5.68 (d, J=6.4 Hz, 1H), 5.61 (d, J=8.4 Hz, 1H), 5.22 (t, J=4.8 Hz, 1H), 3.92-3.89 (m, 1H), 3.72-3.71 (m, 1H), 3.59-3.57 (m, 1H), 3.38 (d, J=8.4 Hz, 1H), 3.12-2.94 (m, 1H), 2.85-2.81 (m, 2H), 2.47-2.44 (m, 1H).

Scheme 2: Synthesis of (2S)-isopropyl 2-(((((4R, 5R,7R,8R)-5-(2,4-dioxo-3,4-dihydropyrimidin-1 (2H)-yl)-8-hydroxy-6-oxa-1-thiaspiro[3.4]octan-7-yl)methoxy)(phenoxy)phosphoryl)amino)propanoate 9

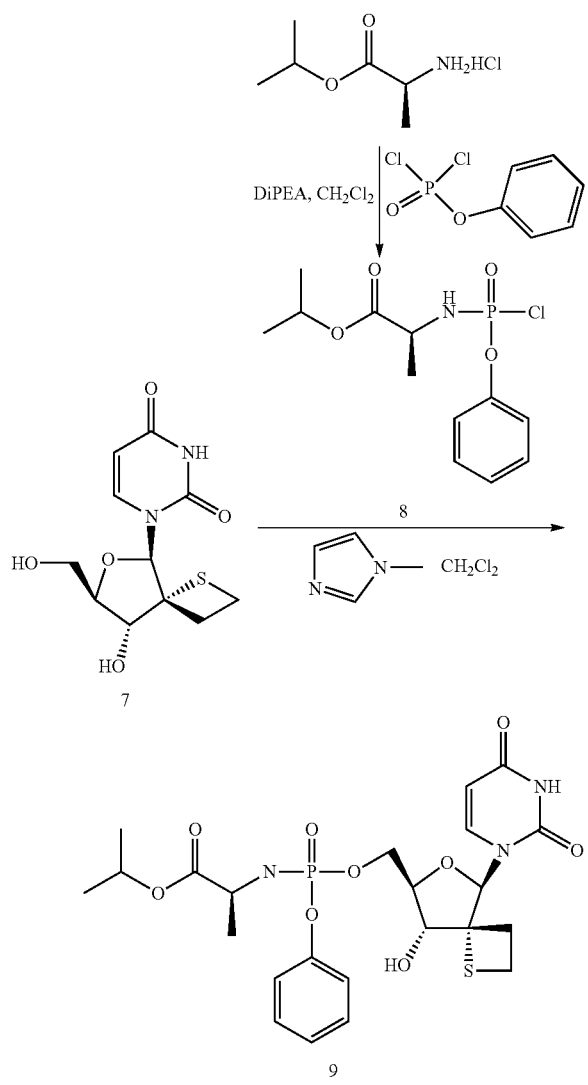

Step 1: Synthesis of (2S)-isopropyl 2-((chloro(phenoxy)phosphoryl)amino)propanoate 8

To a solution of (S)-isopropyl 2-aminopropanoate hydrochloride (5 g, 29.8 mmol) in dichloromethane (50 mL), phenyl phosphorodichloridate (4.45 g, 29.8 mmol) was added at 20° C. The resulting mixture was cooled to −78° C. then diisopropylethyl amine (10.4 mL, 59.6 mmol) was added dropwise. The reaction mixture was stirred at −78° C. for 1 h then the temperature of the reaction was allowed to rise to 20° C. After 1 h the solvent was removed under reduced pressure.

Dry Et$_2$O (about 50 ml) was added and the formed precipitate was filtered off and washed two times with dry Et$_2$O under nitrogen. The filtrate was evaporated to dryness to give yellow colorless oil 8 (8.32 g) which was stored as a 1 M solution in dry tetrahydrofuran (THF) in the freezer at −20° C.

$^1$H NMR (400 MHz, CDCl$_3$) δ ppm 1.24-1.31 (m, 6H), 1.50 (dd, J=7.0, 2.1 Hz, 3H), 4.06-4.20 (m, 1H), 4.23-4.41 (m, 1H), 5.02-5.14 (m, 1H), 7.19-7.30 (m, 3H), 7.34-7.41 (m, 2H).

Step 2: Synthesis of (2S)-isopropyl 2-(((((4R,5R, 7R,8R)-5-(2,4-dioxo-3,4-dihydropyrimidin-1(2H)-yl)-8-hydroxy-6-oxa-1-thiaspiro[3.4]octan-7-yl) methoxy)(phenoxy)phosphoryl)amino)propanoate 9

Compound 7 (500 mg, 1.7 mmol) was dissolved in dry pyridine (15 mL) and stirred for 1 h at RT then evaporated to dryness.

The resulting precipitate was suspended in dry dichloromethane (15 mL) and methyl imidazole (1.3 mL, 17.4 mmol) was added dropwise. The resulting solution was treated with phosphorochloridate 8 (2.62 mL, 2.62 mmol) 1 M solution in dry THF under nitrogen. The reaction mixture was stirred at 20° C. for 16 h and was diluted with DCM (20 mL) and washed with aqueous solution of 1M HCl (3×20 mL). The combined aqueous layers were extracted with DCM (30 mL). The combined organic layers were dried over Na$_2$SO$_4$, filtered and concentrated. The residue was purified by column chromatography (gradient DCM/MeOH 1 to 10%) to yield (100 mg, 12%) of 9 as white foam.

m/z=556 (M+H)$^+$; $^1$H NMR (400 MHz, CDCl$_3$) δ ppm 1.18-1.26 (m, 6H), 1.30-1.38 (m, 2H), 2.62 (s, 1H), 2.66-2.90 (m, 2H), 3.01 (td, J=8.7, 5.6 Hz, 1H), 3.14-3.22 (m, 1H), 3.46-3.63 (m, 1H), 3.70 (s, 1H), 3.85-4.04 (m, 3H), 4.32-4.54 (m, 2H), 4.97-5.07 (m, 1H), 5.59-5.65 (m, 1H), 6.50-6.55 (m, 1H), 7.15-7.25 (m, 3H), 7.30-7.37 (m, 2H), 7.46-7.55 (m, 1H), 9.07 (br s, 1H).

Scheme 3: Synthesis of 4-amino-1-((4R,5R,7R,8R)-8-hydroxy-7-(hydroxymethyl)-6-oxa-1-thiaspiro[3.4] octan-5-yl)pyrimidin-2(1H)-one 12

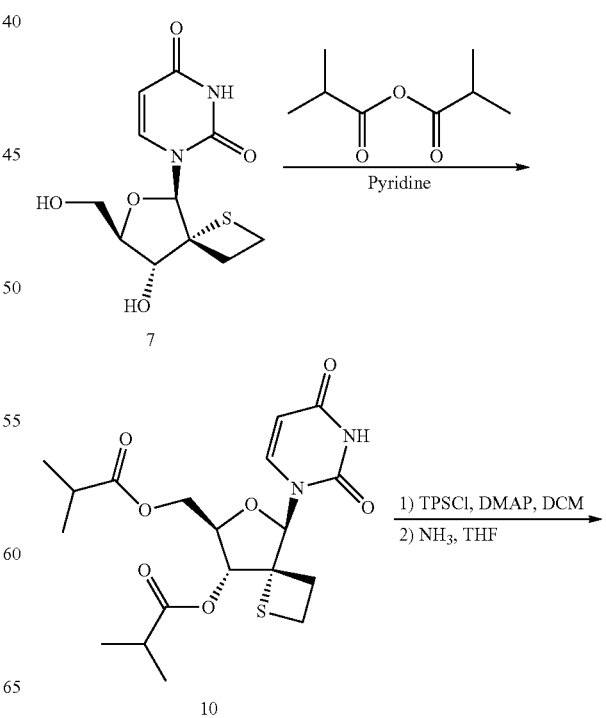

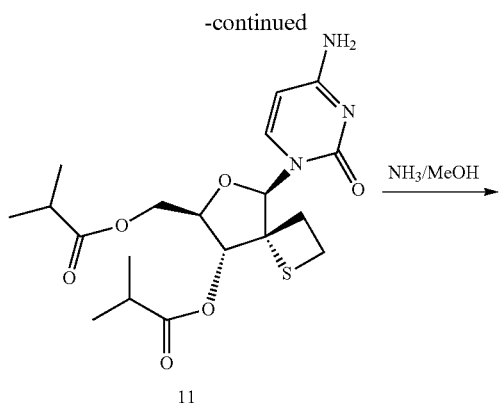

Step 1: Synthesis of (4R,5R,7R,8R)-5-(2,4-dioxo-3,4-dihydropyrimidin-1(2H)-yl)-7-((isobutyryloxy)methyl)-6-oxa-1-thiaspiro[3.4]octan-8-yl isobutyrate 10

Compound 7 (1 g, 3.5 mmol) was evaporated twice with toluene, then dissolved in dry pyridine and the solution was cooled to 0° C. under nitrogen. To the resulting solution isobutyric anhydride (2.9 mL, 17.5 mmol) was added and the mixture was stirred at 20° C. overnight.

The reaction mixture was quenched with MeOH and it was stirred at 20° C. for 1 h. Volatiles were evaporated in vacuum and the crude was purified by column chromatography (gradient heptane and EtOAc 1 to 30%) to yield 10 (1.16 g, 77%) as white solid.

m/z=427 (M+H)⁺; ¹H NMR (360 MHz, DMSO-d₆) δ ppm 1.06-1.24 (m, 12H), 2.52-2.60 (m, 1H), 2.67-2.92 (m, 5H), 3.98-4.03 (m, 1H), 4.18-4.28 (m, 2H), 5.37 (d, J=6.6 Hz, 1H), 5.73 (d, J=8.1 Hz, 1H), 6.19 (s, 1H), 7.64 (d, J=8.1 Hz, 1H), 11.57 (br s, 1H).

Step 2: Synthesis of (4R,5R,7R,8R)-5-(4-amino-2-oxopyrimidin-1(2H)-yl)-7-((isobutyryloxy)methyl)-6-oxa-1-thiaspiro[3.4]octan-8-yl isobutyrate 11

To a mixture of intermediate 10 (1 g, 2.345 mmol), DMAP (57.29 mg, 0.469 mmol) and Et₃N (0.489 mL, 3.52 mmol) in dry DCM (50 mL) at 20° C., TIPSCl (1.065 g, 3.517 mmol) was added. The resulting mixture was stirred at 20° C. under nitrogen for 3 h. Ammonia (4.8 mL, 2.43 mmol, 0.5M in THF) was added and the reaction mixture was stirred vigorously at 20° C. overnight.

The reaction mixture was diluted with CH₂Cl₂ (50 mL) and saturated aqueous solution of NaHCO₃ (50 mL) was added. The two layers were separated; the aqueous layer was extracted with CH₂Cl₂ (3×25 mL). The combined organic layers were dried over Na₂SO₄, filtered off and concentrated under reduced pressure.

The residue was purified by column chromatography ((DCM:MeOH 9:1)/DCM, from 0 to 100%) to yield (1.16 g, 78%) of intermediate 11 as white solid.

m/z=426 (M+H)⁺; ¹H NMR (400 MHz, DMSO-d₆) δ ppm 1.07-1.13 (m, 6H), 1.16-1.20 (m, 3H), 1.23 (d, J=7.0 Hz, 3H), 2.57 (dt, J=13.9, 7.0 Hz, 1H), 2.61-2.75 (m, 1H), 2.78-2.89 (m, 2H), 3.93-3.99 (m, 1H), 4.19-4.28 (m, 2H), 5.35 (d, J=7.0 Hz, 1H), 5.83 (d, J=7.5 Hz, 1H), 6.30 (s, 1H), 7.61 (d, J=7.5 Hz, 1H)

Step 3: Synthesis of 4-amino-1-((4R,5R,7R,8R)-8-hydroxy-7-(hydroxymethyl)-6-oxa-1-thiaspiro[3.4]octan-5-yl)pyrimidin-2(1H)-one 12

Intermediate 11 (588 mg, 1.36 mmol) was dissolved in a solution of methanol ammonia (7N) (25 mL). The reaction mixture was stirred at 20° C. for 16 hours. The solvent was removed and the residue was purified by prep HPLC using method D.

The organic solvents were removed at 40° C. and the aqueous layer was lyophilized to yield 12 (250 mg, 65%) as white solid.

m/z=286 (M+H)⁺; ¹H NMR (400 MHz, DMSO-d₆) δ ppm 2.34-2.45 (m, 1H), 2.69-2.84 (m, 2H), 3.08-3.16 (m, 1H), 3.30 (br s, 1H), 3.32 (br d, J=2.4 Hz, 1H), 3.59 (br d, J=12.1 Hz, 1H), 3.75 (br d, J=12.1 Hz, 1H), 3.84 (d, J=8.8 Hz, 1H), 5.17 (br s, 1H), 5.55 (br s, 1H), 5.69 (d, J=7.5 Hz, 1H), 6.50 (s, 1H), 7.17 (br d, J=23.8 Hz, 2H), 7.95 (d, J=7.5 Hz, 1H).

Scheme 4: Synthesis of (2S)-isopropyl 2-(((((4R,5R,7R,8R)-5-(4-amino-2-oxopyrimidin-1(2H)-yl)-8-hydroxy-6-oxa-1-thiaspiro[3.4]octan-7-yl)methoxy)(phenoxy)phosphoryl)amino)propanoate 17

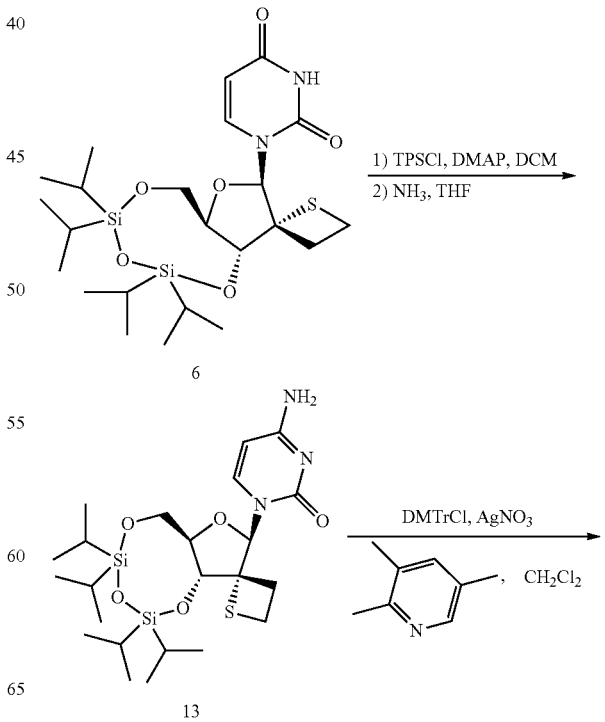

51

-continued

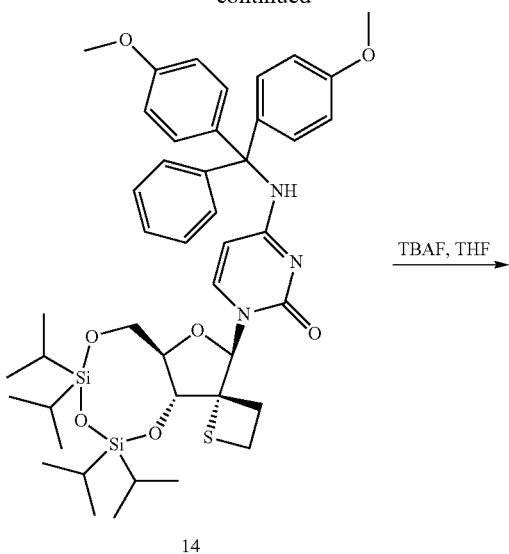

14

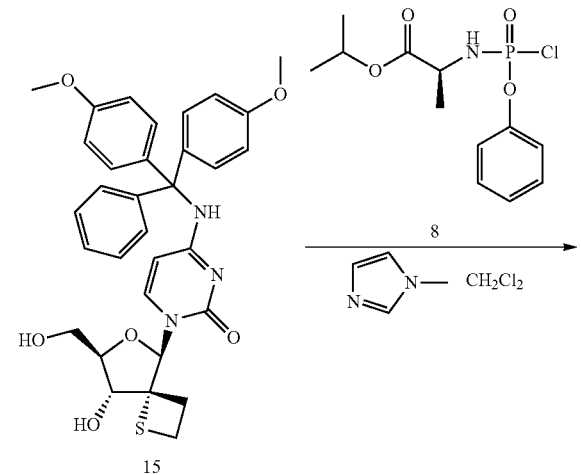

15

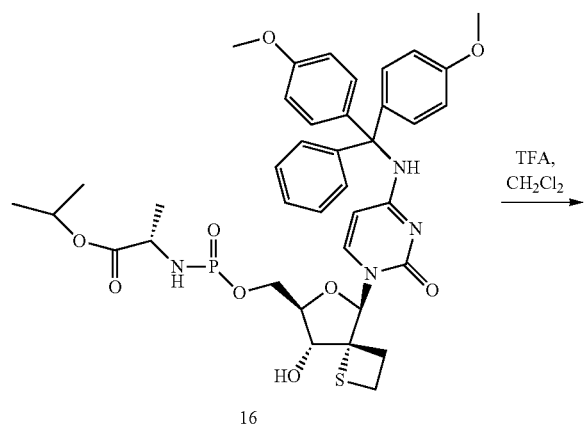

16

52

-continued

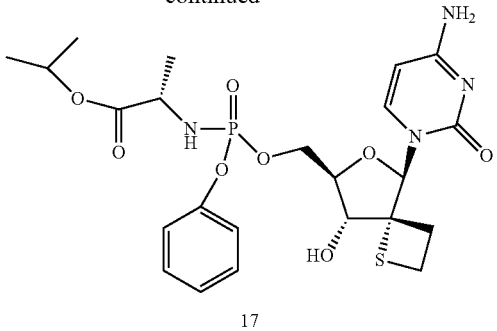

17

Step 1: Synthesis of 4-amino-1-42′R,6aR,8R,9aR)-2,2,4,4-tetraisopropyltetrahydrospiro[furo[3,2-f][1,3,5,2,4]trioxadisilocine-9,2′-thietan]-8-yl)pyrimidin-2(1H)-one 13

To a mixture of intermediate 6 (1.6 g, 3.026 mmol), DMAP (73.9 mg, 0.605 mmol) and Et₃N (0.631 mL, 4.5 mmol) in dry dichloromethane (100 mL) at 20° C., TIPSCl (1.37 g, 4.53 mmol) was added. The resulting mixture was stirred under nitrogen at 20° C. overnight. Then ammonia (60 mL, 30.25 mmol, 0.5M in THF) was added and the reaction mixture was stirred vigorously at 20° C. 3 h. The reaction mixture was diluted with dichloromethane (50 mL) and saturated aqueous solution of NaHCO₃ (100 mL) was added. The two layers were separated, the aqueous layer was extracted with dichloromethane (3×30 mL) and the combined organic layers were dried over Na₂SO₄, filtered off and concentrated under reduced pressure.

The residue was purified by column chromatography ((DCM:MeOH 9:1)/DCM, from 0 to 100%) to yield 13 (1.12 g, 70%) as white foam.

m/z=528 (M+H)⁺

Step 2: Synthesis of 4-((bis(4-methoxyphenyl)(phenyl)methyl)amino)-1-((2′R,6aR,8R,9aR)-2,2,4,4-tetraisopropyltetrahydrospiro[furo[3,2-f][1,3,5,2,4]trioxadisilocine-9,2′-thietan]-8-yl)pyrimidin-2(1H)-one 14

Intermediate 13 (1.12 g, 2.12 mmol) was dissolved in dry dichloromethane (100 mL) then 2,3,5-trimethylpyridine (2.26 mL, 17.4 mmol), silver nitrate (6.34 g, 37.34 mmol) and 4,4′-(chloro(phenyl)methylene)bis(methoxybenzene) (2.15 g, 6.36 mmol) were added. The resulting bright orange suspension was stirred at 20° C. for 2 h.

Then the reaction mixture was quenched with MeOH (10 mL). The reaction mixture was poured into saturated NaHCO₃ solution (50 mL) and extracted with dichloromethane. The organic layer was dried over Na₂SO₄, filtered and evaporated to obtain 14 (1.65 g, 93%) as yellow foam.

m/z=831 (M+H)⁺

Step 3: Synthesis of 4-((bis(4-methoxyphenyl)(phenyl)methyl)amino)-1-((4R,5R,7R,8R)-8-hydroxy-7-(hydroxymethyl)-6-oxa-1-thiaspiro[3.4]octan-5-yl)pyrimidin-2(1H)-one 15

TBAF (1M in THF) [429-41-4] (1.987 mL, 1 M, 1.987 mmol) was added to a solution of intermediate 14 (1.65 g, 1.987 mmol) (crude) in THF [109-99-9] (50 mL). The resulting mixture was stirred under N₂ at 20° C. for 2 h.

The mixture was diluted with EtOAc (50 mL) and poured in water (100 mL) then extracted with EtOAc (3×25 mL). The organic layers were dried over MgSO₄ and the solvent was removed. The resulting residue was purified by column chromatography using dichloromethane and methanol (100/0 to 95/5) to yield 15 (1 g, 85%) as brown solid.

m/z=588 (M+H)⁺

Step 4: Synthesis of (2S)-isopropyl 2-(((((4R,5R,7R,8R)-5-(4-((bis(4-methoxyphenyl)(phenyl)methyl)amino)-2-oxopyrimidin-1 (2H)-yl)-8-hydroxy-6-oxa-1-thiaspiro[3.4]octan-7-yl)methoxy)(phenoxy)phosphoryl)amino)propanoate 16

Intermediate 15 (700 mg, 0.953 mmol) was dissolved in dry pyridine (5 mL) and stirred for 1 h at RT then evaporated to dryness. The obtained foam was suspended in dry dichloromethane (50 mL) and methyl imidazole (0.475 ml, 6 mmol) was added. The resulting solution was treated with (2S)-isopropyl 2-((chloro(phenoxy)phosphoryl)amino)propanoate 8 (1.78 mL, 1.78 mmol, 1 M solution in dry THF) under nitrogen.

The reaction mixture was stirred at 20° C. overnight, then diluted with dichloromethane (50 mL) and poured in water (100 mL), the resulting mixture was acidified by addition of aqueous HCl 1M solution until pH=4. The aqueous layer was extracted with dichloromethane. The combined organic layers were dried over Na₂SO₄, filtered and concentrated. The residue was purified by column chromatography (gradient DCM/MeOH 1 to 10%) to yield 16 (110 mg, 17%).

m/z=858 (M+H)⁺

Step 5: Synthesis of (2S)-isopropyl 2-(((((4R,5R,7R,8R)-5-(4-amino-2-oxopyrimidin-1(2H)-yl)-8-hydroxy-6-oxa-1-thiaspiro[3.4]octan-7-yl)methoxy)(phenoxy)phosphoryl)amino)propanoate 17

Intermediate 16 (110 mg, 0.128 mmol) was dissolved in dichloromethane (15 mL) at 20° C. then 2,2,2-trifluoroacetic acid (0.1 mL, 1.28 mmol) was added. The resulting mixture was stirred at 20° C. for 3 h.

The reaction mixture was quenched with methanol (10 mL) and diluted with dichloromethane (25 mL), the mixture was stirred for 30 min. The bright orange solution became yellow. The reaction mixture was basified with aqueous solution of Na₂CO₃ (until pH=8) and the mixture was stirred for 30 min. The two layers were separated and the aqueous layer was extracted with dichloromethane (3×15 mL). The combined organic layers were dried over Na₂SO₄, filtered off and concentrated under reduced pressure to afford yellow oil. This was purified by prep HPLC using Method D to yield compound 17 (39 mg, 53%) as white powder.

m/z=555 (M+H)⁺; ¹H NMR (400 MHz, CDCl₃) δ ppm 1.17-1.29 (m, 7H), 1.36 (s, 3H), 2.66-2.86 (m, 2H), 2.87-2.99 (m, 1H), 3.23-3.36 (m, 1H), 3.45-3.54 (m, 1H), 3.55-3.72 (m, 1H), 3.78-4.07 (m, 3H), 4.31-4.45 (m, 1H), 4.46-4.56 (m, 1H), 4.90-5.09 (m, 1H), 5.58-5.81 (m, 1H), 6.59-6.77 (m, 1H), 7.12-7.25 (m, 3H), 7.29-7.38 (m, 2H), 7.54-7.69 (m, 1H).

Scheme 5: Synthesis of 1-((4R,5R,7S,8R)-7-fluoro-8-hydroxy-7-(hydroxymethyl)-6-oxa-1-thiaspiro[3.4]octan-5-yl)pyrimidine-2,4(1H,3H)-dione 22

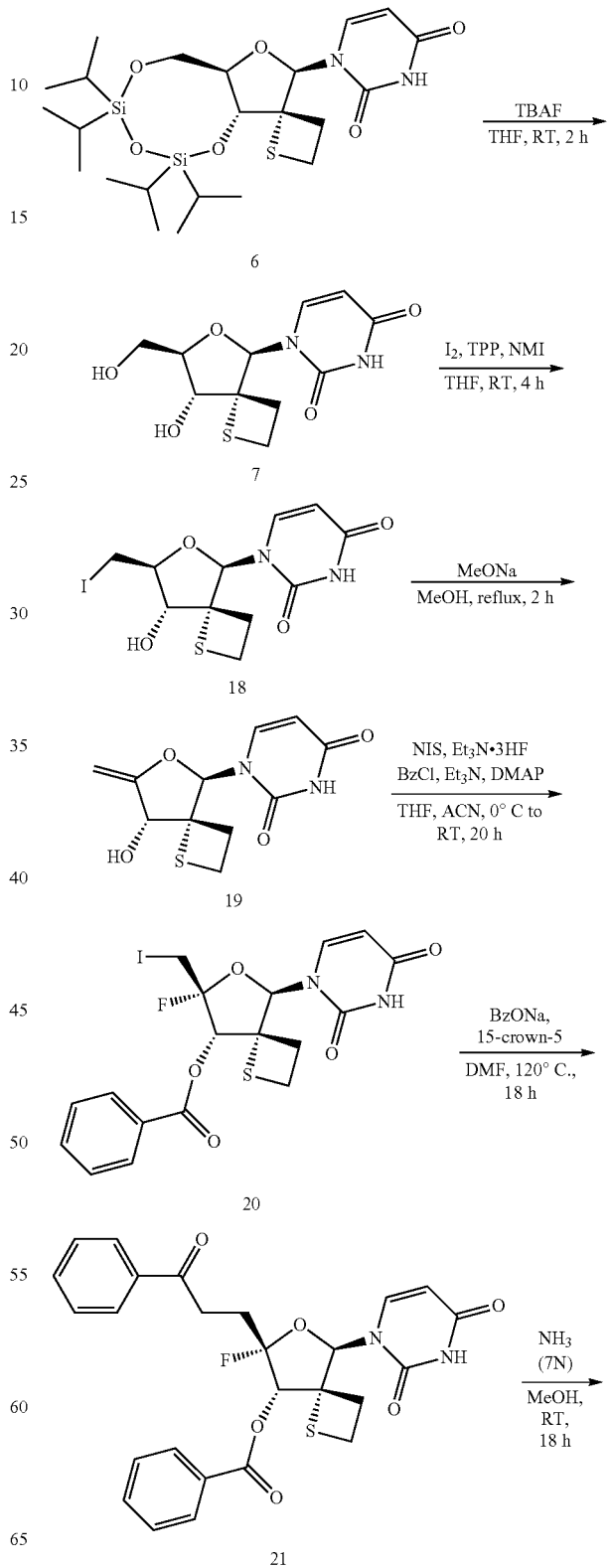

-continued

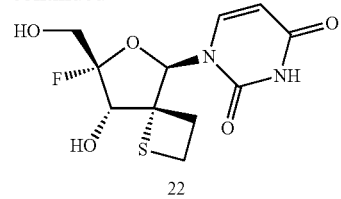

22

Step 1: Synthesis of 1-((4R,5R,7R,8R)-8-hydroxy-7-(hydroxymethyl)-6-oxa-1-thiaspiro[3.4]octan-5-yl)pyrimidine-2,4(1H,3H)-dione 7

To a solution of intermediate 6 (15 g, 28.365 mmol) in THF (300 mL), TBAF (56.7 mL, 56.7 mmol, 1M in THF) was added. The resulting mixture was stirred under $N_2$ atmosphere at RT for 2 h. Afterwards, the solvent was evaporated and the crude was purified by Prep HPLC using method A to yield intermediate 7 (7 g, 86%) as white powder.

MS (ES−): 285.0; $^1$H NMR (400 MHz, DMSO-$d_6$) δ ppm 2.44-2.49 (m, 1H), 2.78-2.90 (m, 2H), 2.99-3.09 (m, 1H), 3.39-3.45 (m, 1H), 3.59 (dd, J=12.4, 2.8 Hz, 1H), 3.74 (dd, J=12.4, 2.1 Hz, 1H), 3.92 (br d, J=8.1 Hz, 1H), 5.23 (br s, 1H), 5.62 (d, J=8.1 Hz, 1H), 5.68 (br s, 1H), 6.40 (s, 1H), 8.00 (d, J=8.1 Hz, 1H), 11.40 (br s, 1H).

Step 2: Synthesis of 1-((4R,5R,7S,8R)-8-hydroxy-7-(iodomethyl)-6-oxa-1-thiaspiro[3.4]octan-5-yl)pyrimidine-2,4(1H,3H)-dione 18

Iodine (6.649 g, 26.196 mmol) and TPP (6.871 g, 26.196 mmol) were added to a suspension of intermediate 7 (5 g, 17.464 mmol) in NMI (6.96 mL, 1.03 g/mL, 87.318 mmol) and THF (200 mL, 0.886 g/mL, 2457.462 mmol) at RT. The reaction mixture was stirred for 4 h under $N_2$ atmosphere. The reaction mixture was quenched with a saturated solution of $Na_2S_2O_3$, concentrated and diluted with EtOAc (100 mL). The organic layer was washed with brine (50 mL) dried over $MgSO_4$ and concentrated. The crude was purified by chromatography column using Heptane/EtOAc as eluent to afford a white solid (6 g) containing intermediate 18 80% and triphenylphosphine oxide 20%.

MS (ES−): 395.0; $^1$H NMR (400 MHz, DMSO-$d_6$) δ ppm 2.55-2.67 (m, 1H), 2.68-2.80 (m, 1H), 2.85-2.95 (m, 2H), 3.35-3.47 (m, 2H), 3.50-3.60 (m, 1H), 3.81 (t, J=6.7 Hz, 1H), 5.66 (d, J=8.1 Hz, 1H), 5.97 (d, J=6.2 Hz, 1H), 6.33 (s, 1H), 7.53 (d, J=8.1 Hz, 1H), 11.50 (s, 1H).

Step 3: 1-((4R,5R,8R)-8-hydroxy-7-methylene-6-oxa-1-thiaspiro[3.4]octan-5-yl)pyrimidine-2,4(1H,3H)-dione 19

The mixture containing intermediate 18 (6 g) was suspended in MeOH (100 mL). NaOMe (30% in MeOH) (14.022 mL, 5.4 M, 75.718 mmol) was added to the suspension. The resulting mixture was stirred at reflux for 2.5 h. The reaction mixture was allowed to cool down to RT and filtrated over a small pad of Decalite®. The filtrate was purified by prep HPLC using method A. The fractions were freeze-dried to deliver intermediate 19 (2.6 g, 55% for two steps) as white solid.

MS (ES−): 267.0
$^1$H NMR (400 MHz, DMSO-d6) δ ppm 2.54-2.68 (m, 1H), 2.72-2.84 (m, 1H), 2.91 (td, J=8.5, 5.7 Hz, 1H), 2.94-3.05 (m, 1H), 4.26 (s, 1H), 4.45 (t, J=1.8 Hz, 1H), 4.56 (br d, J=6.2 Hz, 1H), 5.66 (d, J=7.9 Hz, 1H), 6.06 (d, J=6.4 Hz, 1H), 6.51 (s, 1H), 7.33 (d, J=8.1 Hz, 1H), 11.54 (br s, 1H).

Step 4: Synthesis of (4R,5R,7R,8R)-5-(2,4-dioxo-3,4-dihydropyrimidin-1(2H)-yl)-7-fluoro-7-(iodomethyl)-6-oxa-1-thiaspiro[3.4]octan-8-yl benzoate 20

Intermediate 19 (1 g, 3.7 mmol) was dissolved in ACN (20 mL) and THF (30 mL), the resulting mixture was cooled to −15° C. under $N_2$ atmosphere then triethylamine trihydrofluoride (0.6 mL, 0.989 g/mL, 3.7 mmol) in 5 mL of ACN was added dropwise followed by the addition of NIS (1 g, 4.4 mmol). The resulting reaction mixture was stirred for 1 h at −15° C. under $N_2$ atmosphere. Afterwards, $Et_3N$ (2.6 mL, 0.728 g/mL, 18.6 mmol) and DMAP (9.107 mg, 0.08 mmol) were added to the reaction mixture. The reaction mixture was diluted with 40 mL of THF followed by the dropwise addition of benzoyl chloride (0.433 mL, 1.211 g/mL, 3.7 mmol) at 0° C. The reaction mixture was allowed to warm up to RT and stirred for 3 h. The reaction mixture was diluted with EtOAc (30 mL) and successively washed with brine, a saturated solution of $Na_2S_2O_3$, dried over $MgSO_4$ and purified by column chromatography (heptane/EtOAc) to afford intermediate 20 (1.2 g, yield 62%) as light yellow solid.

MS (ES−): 516.8; $^1$H NMR (400 MHz, DMSO-$d_6$) δ ppm 2.80 (br s, 2H), 2.93 (br d, J=5.3 Hz, 1H), 3.04-3.20 (m, 1H), 3.50-3.77 (m, 2H), 5.78 (br d, J=7.7 Hz, 1H), 6.04 (br s, 1H), 6.59 (br s, 1H), 7.63 (br t, J=7.3 Hz, 2H), 7.70-7.98 (m, 1H), 8.18 (br d, J=7.3 Hz, 2H), 11.65 (br s, 1H).

Step 5: Synthesis of ((4R,5R,7S,8R)-8-(benzoyloxy)-5-(2,4-dioxo-3,4-dihydropyrimidin-1(2H)-yl)-7-fluoro-6-oxa-1-thiaspiro[3.4]octan-7-yl)methyl benzoate 21

Intermediate 20 (1.2 g, 2.3 mmol), sodium benzoate (1.7 g, 11.6 mmol) and 15-crown-5 (4.6 mL, 1.11 g/mL, 23.2 mmol) were suspended in DMF (50 mL) under $N_2$ atmosphere. The reaction mixture was stirred for 18 h at 120° C. Afterwards, the reaction mixture was allowed to cool down to 45-50° C. then diluted with EtOAc (100 mL) and filtrated. The organic layer was washed successively with brine, a saturated solution of $Na_2S_2O_3$, and dried over $Na_2SO_4$. The solvent was removed, the crude was purified by column chromatography (heptane/EtOAc: 100/100 to 50/50) to afford intermediate 21 (700 mg, 59%) as light yellow solid.

MS (ES−): 511.0; $^1$H NMR (400 MHz, $CDCl_3$) δ ppm 2.76 (br s, 1H), 2.89-2.95 (m, 1H), 3.11 (br s, 1H), 3.17-3.30 (m, 1H), 4.54 (dd, J=12.3, 5.7 Hz, 1H), 4.72 (dd, J=12.2, 8.7 Hz, 1H), 5.53-5.64 (m, 1H), 5.92 (s, 1H), 6.58-6.79 (m, 1H), 7.28 (s, 1H), 7.33-7.42 (m, 2H), 7.47-7.54 (m, 2H), 7.54-7.59 (m, 1H), 7.65 (t, J=6.9 Hz, 1H), 7.98 (d, J=7.7 Hz, 2H), 8.25 (d, J=7.6 Hz, 2H).

Step 6: Synthesis of 1-((4R,5R,7S,8R)-7-fluoro-8-hydroxy-7-(hydroxymethyl)-6-oxa-1-thiaspiro[3.4]octan-5-yl)pyrimidine-2,4(1H,3H)-dione 22

Intermediate 21 (700 mg, 1.4 mmol) was solubilized in $NH_3$ (7M in MeOH) (200 mL) and stirred overnight at RT. The solvent was removed, and the solid was triturated in $Et_2O$ to obtain compound 22 (269 mg, 65%).

MS (ES−): 303.0; $^1$H NMR (400 MHz, DMSO-$d_6$) δ ppm 2.32-2.45 (m, 1H), 2.83 (br dd, J=8.4, 4.0 Hz, 1H), 2.88-3.03

(m, 1H), 3.08-3.20 (m, 1H), 3.51-3.67 (m, 2H), 4.08 (br d, J=19.4 Hz, 1H), 5.67 (d, J=7.9 Hz, 1H), 5.75 (br s, 1H), 5.93 (br s, 1H), 6.71 (br s, 1H), 7.65 (br d, J=8.4 Hz, 1H), 11.53 (br s, 1H).

Scheme 6: Synthesis of (2S)-isopropyl 2-(((((4R,5R,7S,8R)-5-(2,4-dioxo-3,4-dihydropyrimidin-1(2H)-yl)-7-fluoro-8-hydroxy-6-oxa-1-thiaspiro[3.4]octan-7-yl)methoxv)(phenoxy)phosphoryl)amino)propanoate 23

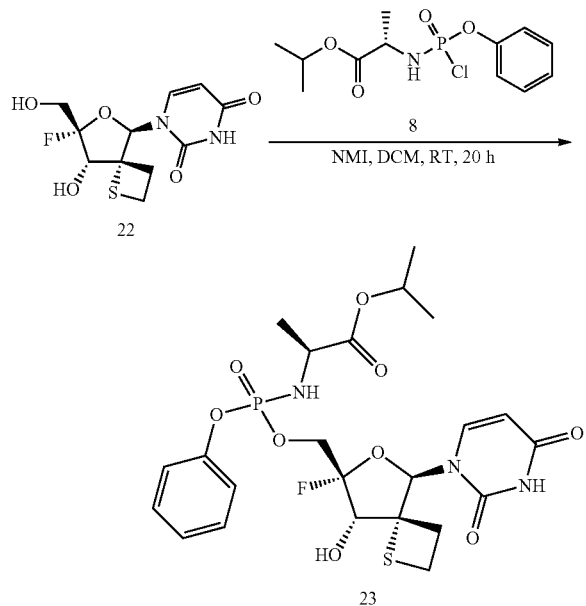

Compound 22 (100 mg, 0.329 mmol) was dissolved in dry pyridine (5 mL) and the solvent was removed under reduced pressure. The foam obtained was solubilized in dichloromethane (5 mL) and N-methyl imidazole (0.131 mL, 1.03 g/mL, 1.643 mmol). To this mixture intermediate 8 (0.5 mL, 1 M, 0.5 mmol) was added dropwise under $N_2$ atmosphere at RT. After 5 h of stirring, another equivalent of intermediate 8 was added. After stirring overnight, the reaction mixture was quenched with a mixture of 20 mL of cold water and 20 mL of dichloromethane. The resulting mixture was acidified with HCl 1M until pH=4 and extracted with dichloromethane (3×50 mL). The organic layer was dried over $Na_2SO_4$, filtrated and the solvent was removed under reduced pressure to afford 400 mg of foam containing the compound. A purification was performed by Prep HPLC using method B to yield 23 (44 mg, yield 23%).

MS (ES−): 572.1; $^1$H NMR (400 MHz, DMSO-$d_6$) δ ppm 1.15 (d, J=6.2 Hz, 6H), 1.21 (dd, J=10.6, 7.3 Hz, 3H), 2.53-2.64 (m, 1H), 2.82-2.97 (m, 2H), 3.05 (br s, 1H), 3.72-3.85 (m, 1H), 4.14-4.34 (m, 3H), 4.85 (dt, J=12.5, 6.3 Hz, 1H), 5.58 (d, J=8.1 Hz, 1H), 6.02-6.19 (m, 2H), 6.67 (br s, 1H), 7.14-7.25 (m, 3H), 7.37 (br t, J=7.9 Hz, 3H), 10.86-11.82 (m, 1H).

Scheme 7: Synthesis of (2R)-butyl 2-(((((4R,5R,7S,8R)-5-(2,4-dioxo-3,4-dihydropyrimidin-1(2H)-yl)-7-fluoro-8-hydroxy-6-oxa-1-thiaspiro[3.4]octan-7-yl)methoxy)(phenoxy)phosphoryl)amino)propanoate 25

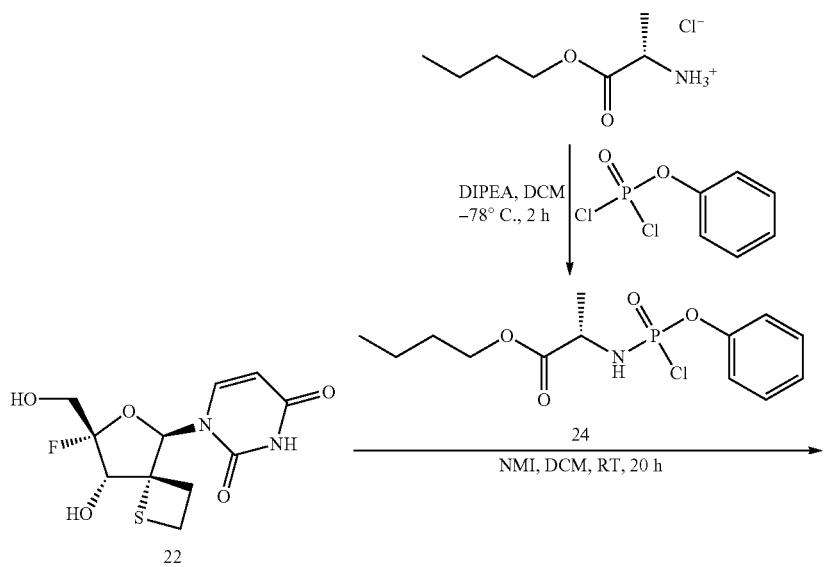

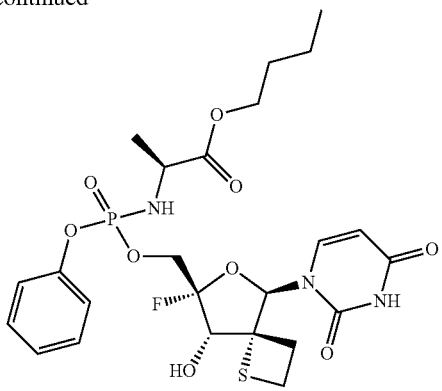

25

Step 1: Synthesis of (2S)-butyl 2-((chloro(phenoxy)phosphoryl)amino)propanoate 24

(S)-1-Butoxy-1-oxopropan-2-aminium (2 g, 11 mmol) was solubilized in dichloromethane (50 mL) and cooled to −78° C. To this mixture phenyl phosphorodichloridate (1.6 mL, 11 mmol) was added slowly followed by the dropwise addition of DIPEA (3.9 mL, 0.742 g/mL, 22 mmol) under $N_2$ atmosphere. The reaction mixture was stirred for 1 h then allowed to warm up until RT and stirred for 2 h. Afterwards, the solvent was removed. Dry $Et_2O$ (100 mL) was added under nitrogen the resulting mixture was filtrated and the filtrate was concentrated under nitrogen flow reduced pressure to afford intermediate 24 (2.877 g, yield 82%) as colorless oil. This oil was stored as a 1 M solution in dry tetrahydrofuran in the freezer at −20° C.

$^1$H NMR (400 MHz, $CDCl_3$) δ ppm 0.94 (td, J=7.4, 5.4 Hz, 3H), 1.33-1.45 (m, 2H), 1.49-1.54 (m, 3H), 1.59-1.70 (m, 2H), 4.09-4.26 (m, 3H), 4.53-4.67 (m, 1H), 7.20-7.30 (m, 3H), 7.33-7.41 (m, 2H).

Step 2: Synthesis of (2S)-butyl 2-(((((4R,5R,7S,8R)-5-(2,4-dioxo-3,4-dihydropyrimidin-1(2H)-yl)-7-fluoro-8-hydroxy-6-oxa-1-thiaspiro[3.4]octan-7-yl)methoxy)(phenoxy)phosphoryl)amino)propanoate 25

Compound 22 (100 mg, 0.329 mmol) was dissolved in pyridine (5 mL) and the solvent was removed under reduced pressure. The foam obtained was solubilized in dichloromethane (5 mL) and N-methyl imidazole (0.131 mL, 1.643 mmol). To the resulting mixture, intermediate 24 (0.657 mL, 1 M, 0.657 mmol) was added dropwise under $N_2$ atmosphere at RT. After 5 h of stirring, another equivalent of intermediate 24 was added and the mixture was stirred overnight, the reaction mixture was quenched with a mixture of 20 mL of cold water and 20 mL of dichloromethane. The resulting mixture was acidified with HCl 1M until pH=4 and extracted with dichloromethane (3×50 mL). The organic layer was dried over $Na_2SO_4$, filtrated and the solvent was removed under reduced pressure to afford 300 mg of foam containing the compound. Purification was performed by Prep HPLC using method B to yield 25 (32.6 mg, 17%).

MS (ES−): 586.1; $^1$H NMR (400 MHz, DMSO-$d_6$) δ ppm 0.85 (td, J=7.4, 2.6 Hz, 3H), 1.22 (dd, J=10.6, 7.3 Hz, 3H), 1.25-1.33 (m, 2H), 1.47-1.54 (m, 2H), 2.52-2.62 (m, 1H), 2.88 (br s, 2H), 3.05 (br s, 1H), 3.83 (br d, J=9.7 Hz, 1H), 4.00 (qd, J=6.4, 2.5 Hz, 2H), 4.22 (br d, J=9.2 Hz, 3H), 5.57 (d, J=8.4 Hz, 1H), 6.13 (br d, J=8.4 Hz, 2H), 6.60-6.73 (m, 1H), 7.20 (br t, J=8.2 Hz, 3H), 7.33-7.40 (m, 3H), 11.00-11.61 (m, 1H).

Scheme 8: Synthesis of 4-amino-1-((4R,5R,7S,8R)-7-fluoro-8-hydroxy-7-(hydroxymethyl)-6-oxa-1-thiaspiro[3.4]octan-5-yl)pyrimidin-2(1H)-one 27

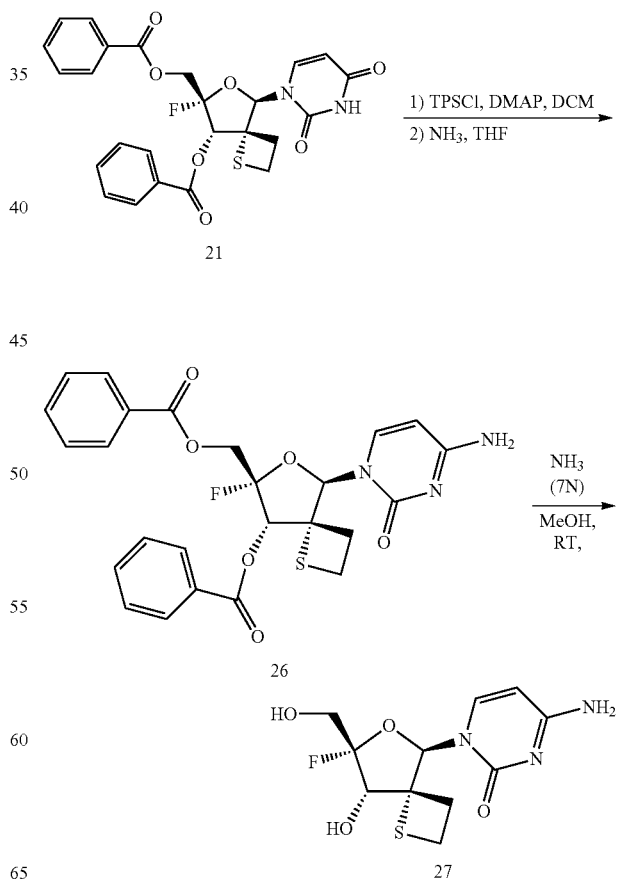

Step 1: Synthesis of (4R,5R,7S,8R)-5-(4-amino-2-oxopyrimidin-1(2H)-yl)-7-((benzoyloxy)methyl)-7-fluoro-6-oxa-1-thiaspiro[3.4]octan-8-yl benzoate 26

Intermediate 21 (600 mg, 1.171 mmol), DMAP (28.6 mg, 0.234 mmol) and Et$_3$N (0.244 mL, 0.728 g/mL, 1.8 mmol) were solubilized in dichloromethane (60 mL). To the resulting mixture TPSCl (532 mg, 1.8 mmol) was added. The reaction mixture was stirred for 20 h at RT. Afterwards, NH$_3$ (0.5 M in THF) (60 mL) was added to the reaction mixture. The resulting reaction mixture was stirred for 3 h. The reaction mixture was poured in a mixture of dichloromethane (60 mL) and saturated solution of NaHCO$_3$. The aqueous layer was extracted with dichloromethane (3×60 mL). The organic layer was dried over Na$_2$SO$_4$ and purified on column chromatography (heptane/EtOAc: 100/0 to 50/50) to afford intermediate 26 (350 mg, 58%).
MS (ES−): 510.0

Step 2: Synthesis of 4-amino-1-((4R,5R,7S,8R)-7-fluoro-8-hydroxy-7-(hydroxymethyl)-6-oxa-1-thiaspiro[3.4]octan-5-yl)pyrimidin-2(1H)-one 27

Intermediate 26 (150 mg, 0.293 mmol) was stirred in NH$_3$ (7M in MeOH) (50 mL) for 5 h at RT. The solvent was removed and the crude was purified by Prep HPLC using method C to yield compound 27 (54.8 mg, 62%).

MS (ES−): 302.0; $^1$H NMR (400 MHz, DMSO-d$_6$) δ ppm 2.35 (ddd, J=12.2, 8.6, 4.0 Hz, 1H), 2.74-2.93 (m, 2H), 3.16-3.22 (m, 1H), 3.56-3.68 (m, 2H), 4.05 (br d, J=21.1 Hz, 1H), 5.42 (s, 2H), 5.73 (d, J=7.5 Hz, 1H), 6.79 (s, 1H), 7.11 (s, 2H), 7.59 (d, J=7.5 Hz, 1H).

Scheme 9: Synthesis of (2S)-isopropyl 2-(((((4R,5R,7S,8R)-5-(4-amino-2-oxopyrimidin-1(2H)-yl)-7-fluoro-8-hydroxy-6-oxa-1-thiaspiro[3.4]octan-7-yl)methoxy)(phenoxy)phosphoryl)amino)propanoate 31

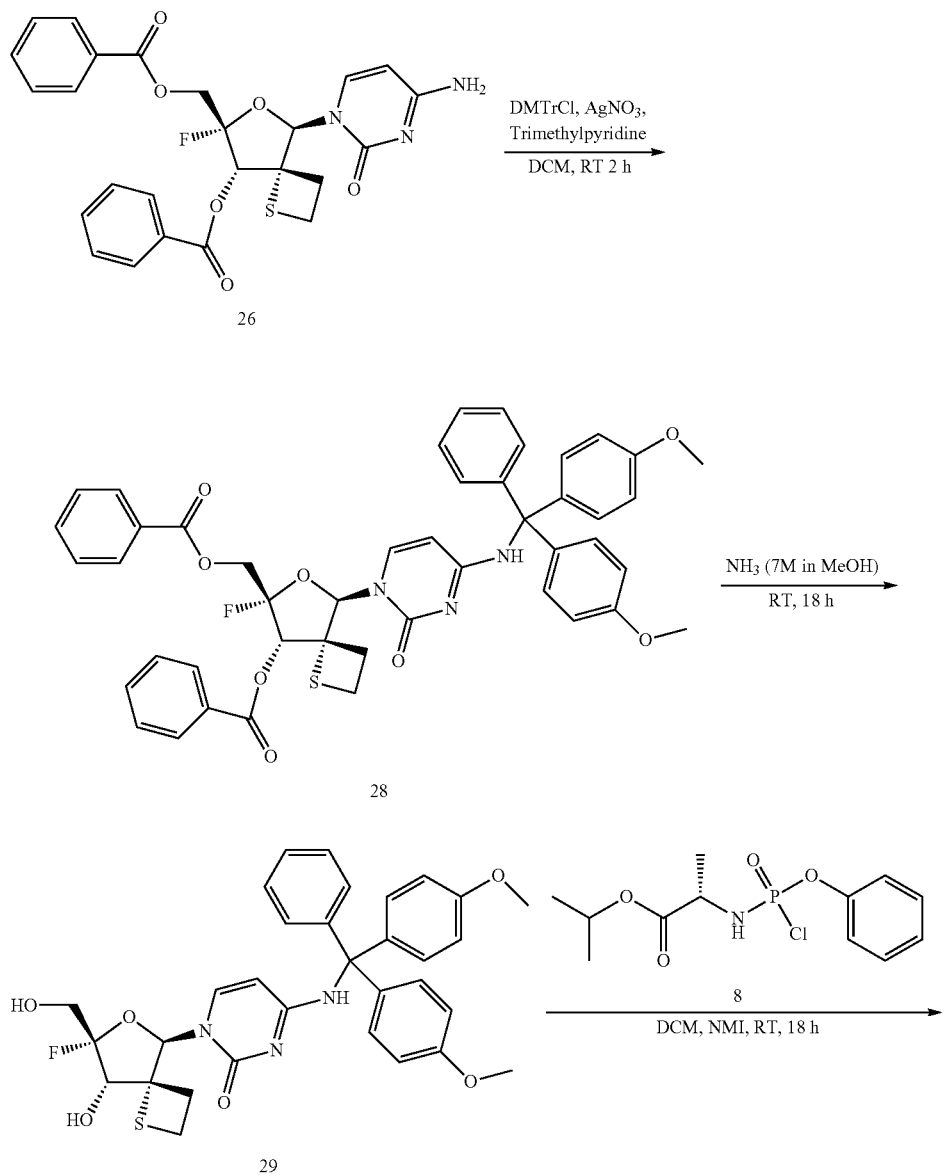

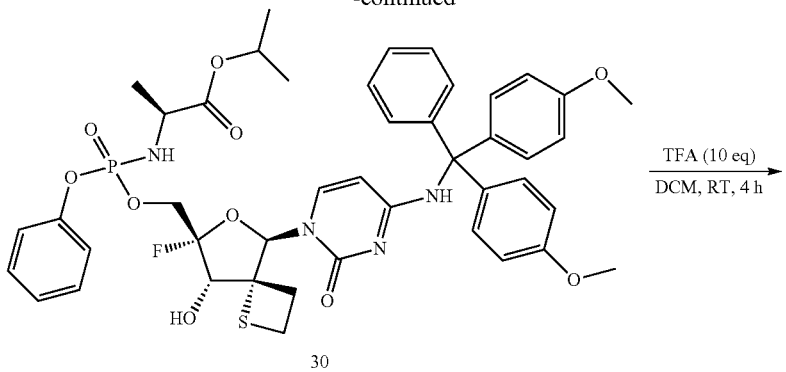

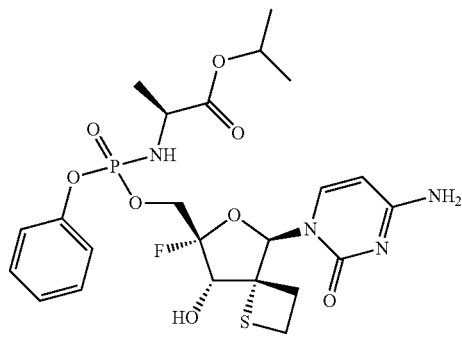

Step 1: Synthesis of ((4R,5R,7S,8R)-8-(benzoyloxy)-5-(4-((bis(4-methoxyphenyl)(phenyl)methyl)amino)-2-oxopyrimidin-1(2H)-yl)-7-fluoro-6-oxa-1-thiaspiro[3.4]octan-7-yl)methyl benzoate 28

Intermediate 26 (600 mg, 1.172 mmol) was dissolved in dichloromethane (20 mL). To the resulting mixture 4,4'-(chloro(phenyl)methylene)bis(methoxybenzene) (1.2 g, 3.5 mmol), Silver Nitrate (3.4 g, 20 mmol) and 2,3,5-trimethylpyridine (1.2 mL, 0.931 g/mL, 9.6 mmol) were added at RT. The reaction mixture was stirred for 2 h under $N_2$ atmosphere. Afterwards, the reaction mixture was poured in a mixture of dichloromethane (20 mL) and cold water (50 mL). The aqueous layer was extracted with dichloromethane (3×25 mL). The organic layer was dried over $Na_2SO_4$ and purified on column chromatography (Heptane/EtOAc: 100/0 to 70/30) to afford intermediate 28 (470 mg, 49%) as white solid.

MS (ES−): 812.2

Step 2: Synthesis of 4-((bis(4-methoxyphenyl)(phenyl)methyl)amino)-1-((4R,5R,7S,8R)-7-fluoro-8-hydroxy-7-(hydroxymethyl)-6-oxa-1-thiaspiro[3.4]octan-5-yl)pyrimidin-2(1H)-one 29

Intermediate 28 (470 mg, 0.577 mmol) was solubilized in $NH_3$ (7M in MeOH) (150 mL, 7 M, 1050 mmol) and stirred for 2 h at RT. The solvent was removed and the crude was triturated in $Et_2O$ to obtain: intermediate 29 (310 mg, 87%) as white solid. MS (ES−): 604.3

Step 3: Synthesis of (2S)-isopropyl 2-(((((4R,5R,7S,8R)-5-(4-((bis(4-methoxyphenyl)(phenyl)methyl)amino)-2-oxopyrimidin-1(2H)-yl)-7-fluoro-8-hydroxy-6-oxa-1-thiaspiro[3.4]octan-7-yl)methoxy)(phenoxy)phosphoryl)amino)propanoate 30

Intermediate 29 (310 mg, 0.512 mmol) was dissolved in pyridine and the solvent was removed under reduced pressure to obtain a foam. This foam was dissolved in THF (10 mL) and NMI (0.204 mL, 1.03 g/mL, 2.559 mmol) was added. The reaction mixture was stirred for 5 min at RT under $N_2$ atmosphere. Isopropyl (2S)-2-[[chloro(phenoxy)phosphoryl]amino]propanoate 8 (1.024 mL, 1 M, 1.024 mmol) was added slowly to the mixture and the resulting mixture was stirred for 6 h. The reaction mixture was poured in a mixture of cold water (50 mL) and DCM (50 mL), acidified until pH=4 with aqueous solution of HCl 1M. The aqueous layer was extracted with DCM (3×50 mL). The organic layer was dried over $MgSO_4$ and the solvent was removed under reduced pressure. The crude obtained was purified by prep HPLC using method B. The fraction obtained was freeze-dried to deliver intermediate 30 (100 mg, 22%).

MS (ES−): 873.2

Step 4: Synthesis of (2S)-isopropyl 2-(((((4R,5R,7S,8R)-5-(4-amino-2-oxopyrimidin-1(2H)-yl)-7-fluoro-8-hydroxy-6-oxa-1-thiaspiro[3.4]octan-7-yl)methoxy)(phenoxy)phosphoryl)amino)propanoate 31

TFA (0.0875 mL, 1.49 g/mL, 1.143 mmol) was added to a solution of intermediate 19 (100 mg, 0.114 mmol) in DCM (10 mL) at RT. The resulting mixture was stirred at RT under $N_2$ atmosphere for 1 h. The reaction mixture was poured in MeOH (50 mL) then then solvents were evaporated. The crude was purified by prep HPLC using method B. The fraction obtained was freeze-dried to deliver compound 31 (20 mg, 31%).

MS (ES−): 571.3; $^1$H NMR (400 MHz, DMSO-$d_6$) δ ppm 1.12-1.17 (m, 6H), 1.18-1.24 (m, 3H), 2.26-2.38 (m, 1H), 2.83 (s, 2H), 3.06-3.18 (m, 1H), 3.73-3.85 (m, 1H), 4.01-4.29 (m, 3H), 4.85 (td, J=6.3, 2.4 Hz, 1H), 5.70 (dd, J=7.5, 4.0 Hz, 1H), 6.12 (br s, 2H), 7.16-7.24 (m, 3H), 7.32-7.40 (m, 4H), 7.48-7.65 (m, 1H).

Scheme 10: Synthesis of 1-((2'R,4aS,6R,7aR)-2-(cyclopentyloxy)-4a-fluoro-2-oxidotetrahydrospiro[furo[3,2-d][1,3,2]dioxaphosphinine-7,2'-thietan]-6-yl)pyrimidine-2.4(1H,3H)-dione 35

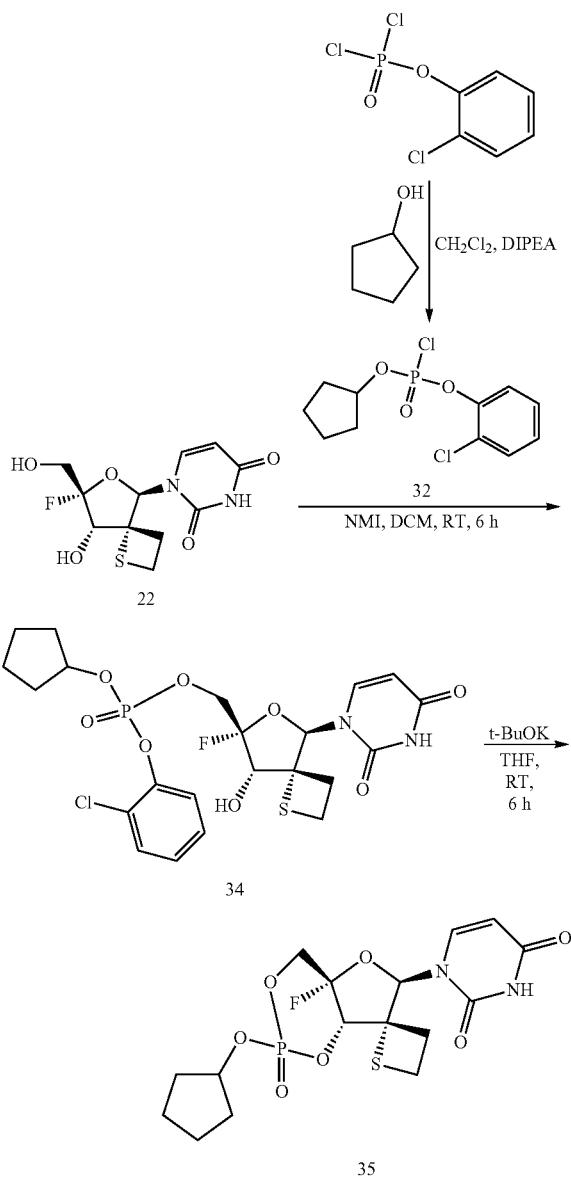

Step 1: Synthesis of 2-chlorophenyl cyclopentyl phosphorochloridate 32

Cyclopentanol (1.096 mL, 0.786 g/mL, 10 mmol) was solubilized in DCM (20 mL) and cooled down to −78° C. To this mixture, 2-chlorophenyl-dichlorophosphate (1.64 mL, 1.49 g/mL, 10 mmol) was added followed by the dropwise addition of DIPEA (1.72 mL, 0.75 g/mL, 10 mmol). The reaction mixture was stirred for 20 h from −78° C. to RT under $N_2$ atmosphere. The solution was used as such in step 2.

Step 2: Synthesis of 2-chlorophenyl cyclopentyl (((4R,5R,7S,8R)-5-(2,4-dioxo-3,4-dihydropyrimidin-1(2H)-yl)-7-fluoro-8-hydroxy-6-oxa-1-thiaspiro[3.4]octan-7-yl)methyl) phosphate 34

Intermediate 22 (284 mg, 0.933 mmol) was dissolved in pyridine (5 mL) and the solvent was removed under reduced pressure to obtain a foam. The foam was dissolved in DCM (10 mL) and NMI (0.372 mL, 1.03 g/mL, 4.666 mmol) at RT under $N_2$ atmosphere. To this mixture, intermediate 32 (2.24 mL, 0.5 M, 1.12 mmol) was added at RT. After 6 h, the reaction mixture was successively poured in a mixture of DCM (20 mL) and cold water (20 mL), acidified until pH=4 with aqueous HCl 1M solution and extracted with DCM (3×50 mL). The organic layer was dried over $MgSO_4$, concentrated and the crude was purified by column chromatography using DCM/MeOH as eluent to afford intermediate 34 (350 mg, 67%) as white solid.

MS (ES−): 561.1; $^1$H NMR (400 MHz, DMSO-$d_6$) δ ppm 1.51-1.71 (m, 4H), 1.77 (dt, J=7.3, 3.9 Hz, 4H), 2.56-2.70 (m, 1H), 2.83-2.94 (m, 2H), 2.94-3.04 (m, 1H), 4.26-4.48 (m, 3H), 5.00 (br d, J=3.3 Hz, 1H), 5.56-5.64 (m, 1H), 6.13 (br s, 1H), 6.62 (br s, 1H), 7.22-7.28 (m, 1H), 7.32-7.52 (m, 3H), 7.57 (d, J=7.9 Hz, 1H), 11.55 (br s, 1H).

Step 3: Synthesis of 1-((2'R,4aS,6R,7aR)-2-(cyclopentyloxy)-4a-fluoro-2-oxidotetrahydrospiro[furo[3,2-d][1,3,2]dioxaphosphinine-7,2'-thietan]-6-yl)pyrimidine-2,4(1H,3H)-dione 35

Intermediate 34 (300 mg, 0.533 mmol) was solubilized in THF (7 mL) and tBuOK (119.6 mg, 1.066 mmol) was added at RT under $N_2$ atmosphere. After 6 h, the reaction mixture was successively poured in a mixture of cold water (20 mL) and EtOAc (20 mL), acidified until pH=3 with aqueous HCl 1M solution and extracted with EtOAc (3×50 mL). The organic layer was dried over $MgSO_4$, concentrated and the crude was purified by prep HPLC using method B. The fraction obtained was freeze-dried to deliver 35 (46.3 mg, 20%).

MS (ES−): 433.0; $^1$H NMR (400 MHz, DMSO-$d_6$) δ ppm 1.61 (br s, 2H), 1.74 (br s, 2H), 1.88 (br s, 4H), 2.67-2.90 (m, 1H), 2.96 (br d, J=9.9 Hz, 1H), 2.98-3.09 (m, 2H), 4.26-4.39 (m, 1H), 4.55-4.71 (m, 1H), 5.00 (m, 1H), 5.46 (br d, J=19.8 Hz, 1H), 5.78 (br d, J=7.7 Hz, 1H), 6.39 (s, 1H), 8.02 (br d, J=7.7 Hz, 1H), 11.62 (br s, 1H).

Scheme 11: Synthesis of 4-chlorophenyl (((4R,5R, 7S,8R)-5-(2,4-dioxo-3,4-dihydropyrimidin-1(2H)-yl)-7-fluoro-8-hydroxy-6-oxa-1-thiaspiro[3.4]octan-7-yl)methyl) isopropyl phosphate (37)

Scheme 12: Synthesis of 1-((2R,2'R,4aS,6R,7aR)-2-(cyclobutylamino)-4a-fluoro-2-oxidotetrahydrospiro [furo[3,2-d][1,3,2]dioxaphosphinine-7,2'-thietan]-6-yl)pyrimidine-2,4(1H,3H)-dione 40a and 1-((2S,2'R, 4aS,6R,7aR)-2-(cyclobutylamino)-4a-fluoro-2-oxidotetrahydrospiro[furo[3,2-d][1,3,2] dioxaphosphinine-7,2'-thietan]-6-yl)pyrimidine-2,4 (1H,3H)-dione 40b

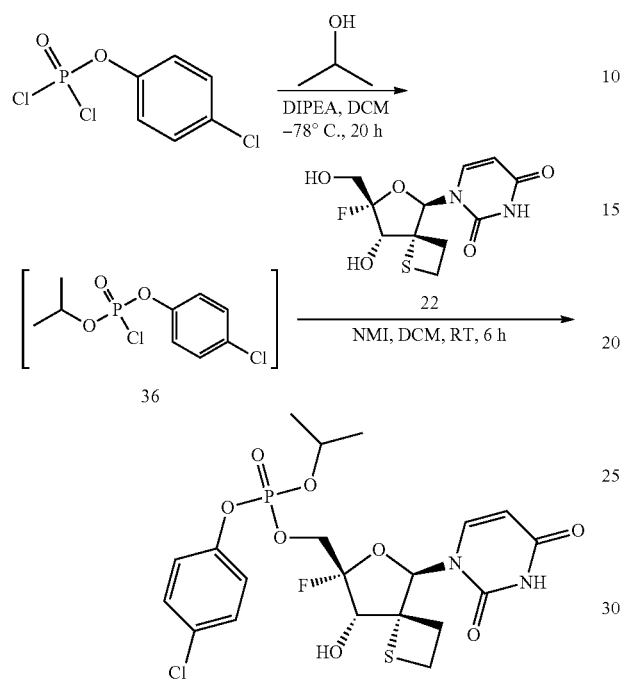

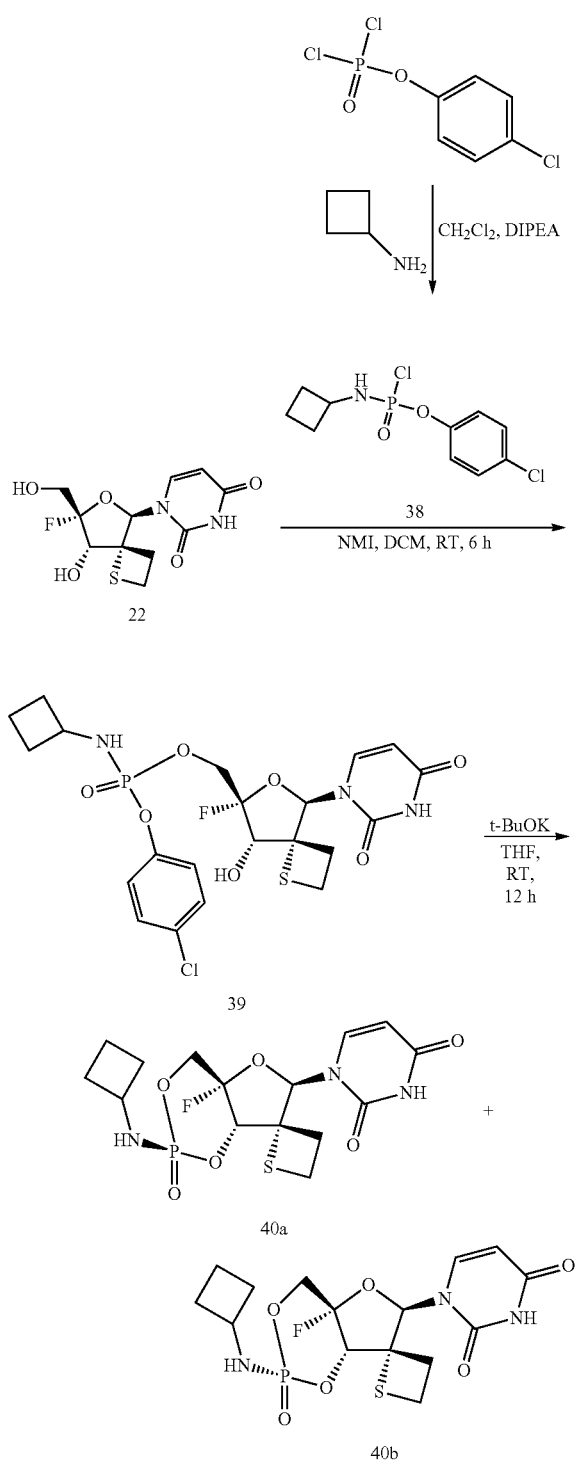

1-chloro-4-dichlorophosphoryloxy-benzene (1.628 mL, 1.508 g/mL, 10 mmol) was dissolved in DCM (25 mL) and the mixture was cooled to −15° C. under $N_2$ atmosphere. To this mixture, isopropanol (0.765 mL, 0.786 g/mL, 10 mmol) was added slowly followed by the dropwise addition of DIPEA (1.723 mL, 0.75 g/mL, 10 mmol). The reaction mixture was stirred for 20 h from −15° C. to RT to obtain reagent (36) in situ. Compound 22 (100 mg, 0.329 mmol) was dissolved in pyridine (5 mL) and the solvent was removed under reduced pressure. The foam was placed in DCM (5 mL) and NMI (0.131 mL, 1.03 g/mL, 1.643 mmol) was added. The reaction mixture was stirred for 5 min at RT. The mixture containing 36 (1.232 mL, 0.4 M, 0.493 mmol) was added and the reaction mixture was stirred for 4 h at RT under $N_2$ atmosphere. The reaction mixture was poured in a mixture of cold water (20 mL) and DCM (20 mL). The aqueous layer was extracted with DCM (3×50 mL). The organic layer was dried over $MgSO_4$ and the solvent was removed under reduced pressure. The crude obtained was purified by Prep HPLC using method E. The fractions obtained were freeze-dried to deliver compound 37 (50 mg, yield 28%) as white solid.

MS (ES−): 535.1; $^1$H NMR (400 MHz, DMSO-$d_6$) δ ppm 1.27 (dd, J=9.0, 6.1 Hz, 6H), 2.53-2.70 (m, 1H), 2.82-2.94 (m, 2H), 2.94-3.04 (m, 1H), 4.22-4.43 (m, 3H), 4.70 (dqd, J=12.6, 6.3, 6.3, 1.8 Hz, 1H), 5.62 (t, J=8.4 Hz, 1H), 6.11 (br s, 1H), 6.61 (br s, 1H), 7.20-7.27 (m, 2H), 7.44 (d, J=8.6 Hz, 3H), 11.50 (br s, 1H).

Step 1: Synthesis of 4-chlorophenyl cyclobutylphosphoramidochloridate 38

Cyclobutanamine (5 mL, 0.83 g/mL, 58.35 mmol) was dissolved in dry dichloromethane (50 mL, 1.326 g/mL, 780.622 mmol) the resulting mixture was stirred at −78° C. for 10 min, then 4-chlorophenyl phosphorodichloridate (9.497 mL, 1.508 g/mL, 58.35 mmol) was added dropwise (white precipitate). The resulting mixture was stirred at −78° C. for 10 min, then DIPEA [7087-68-5] (11.18 mL, 0.742 g/mL, 64.185 mmol) was added dropwise, and a clear solution developed. The resulting mixture was stirred at −78° C. for 2 hours and stirred at RT for 2 hours. The solvent was removed under reduced pressure.

Dry Et$_2$O (about 50 mL) was added and the formed precipitate was filtered off and washed two times with dry Et2O under a flow of nitrogen. The filtrate was evaporated to dryness and yellow colorless oil was isolated (18.7 g). This was dissolved in THF (66.8 mL) and kept in the freezer at −18° C. as 1 M solution of intermediate 38 in THF.

Step 2: Synthesis of 4-chlorophenyl (((4R,5R,7S,8R)-5-(2,4-dioxo-3,4-dihydropyrimidin-1(2H)-yl)-7-fluoro-8-hydroxy-6-oxa-1-thiaspiro[3.4]octan-7-yl)methyl) cyclobutylphosphoramidate 39

The starting material (400 mg, 1.314 mmol) was dissolved in pyridine (10 mL) and stirred for 30 min at RT then evaporated to dryness.

To a stirred solution of nucleoside 22 (400 mg, 1.314 mmol) in dry dichloromethane (50 mL, 1.326 g/mL, 780.622 mmol) was added methyl imidazole (1079.268 mg, 13.145 mmol) until all 22 was dissolved. The resulting solution was treated with the phosphorochloridate 38 (552.266 mg, 1.972 mmol) 1 M solution in dry THF under argon atmosphere. The reaction mixture was stirred at RT overnight and was diluted with DCM (50 mL) and poured in water (100 mL). The resulting mixture was acidified by addition of HCl 1M solution until pH=4. The resulting mixture was extracted with dichloromethane dried over MgSO4 and concentrated. The residue was purified by column chromatography to yield 39 (430 mg, 38%) as a white solid.

m/z=549 (M+H)$^+$; $^1$H NMR (400 MHz, DMSO-d$_6$) δ ppm 1.32-1.56 (m, 2H), 1.72-1.90 (m, 2H), 1.97-2.14 (m, 2H), 2.54-2.65 (m, 1H), 2.79-2.95 (m, 2H), 2.96-3.11 (m, 1H), 3.47-3.66 (m, 1H), 4.08-4.35 (m, 3H), 5.53-5.67 (m, 1H), 5.92-6.18 (m, 2H), 6.58-6.73 (m, 1H), 7.15-7.28 (m, 2H), 7.30-7.61 (m, 3H), 11.38-11.62 (m, 1H)

Step 3: Synthesis of 1-((2R,2'R,4aS,6R,7aR)-2-(cyclobutylamino)-4a-fluoro-2-oxidotetrahydrospiro[furo[3,2-d][1,3,2]dioxaphosphinine-7,2'-thietan]-6-yl)pyrimidine-2,4(1H,3H)-dione 40a and 1-((2S,2'R,4aS,6R,7aR)-2-(cyclobutylamino)-4a-fluoro-2-oxidotetrahydrospiro[furo[3,2-d][1,3,2]dioxaphosphinine-7,2'-thietan]-6-yl)pyrimidine-2,4(1H,3H)-dione 40b Intermediate 39 (130 mg, 0.237 mmol) was dissolved in DMSO (5 mL, 1.092 g/mL, 69.879 mmol) and treated at RT with potassium terbutoxide (0.0399 g, 0.356 mmol). The resulting mixture was stirred at RT overnight. This was purified using HPLC. The aqueous layer was lyophilized and the compounds were isolated as white powder 40a (22.8 mg, 23%) and 40b (18 mg, 18%). m/z=420 (M+H)$^+$; $^1$H NMR (600 MHz, Acetone, −11° C.) δ ppm 1.50-1.66 (m, 4H), 2.04-2.07 (m, 4H), 2.20-2.26 (m, 2H), 2.32-2.40 (m, 2H), 2.86 (ddd, J=13.1, 8.7, 4.7 Hz, 1H), 2.94-3.04 (m, 3H), 3.04-3.22 (m, 4H), 3.69-3.81 (m, 2H), 4.38-4.47 (m, 2H), 4.52 (ddd, J=22.2, 12.0, 9.4 Hz, 1H), 4.83 (dd, J=31.0, 11.3 Hz, 1H), 4.96 (d, J=18.8 Hz, 1H), 5.49 (br dd, J=15.0, 9.8 Hz, 1H), 5.55 (dd, J=15.1, 9.9 Hz, 1H), 5.61 (dd, J=19.9, 1.9 Hz, 1H), 5.73 (d, J=8.2 Hz, 1H), 5.83 (d, J=7.9 Hz, 1H), 6.25 (s, 1H), 7.05 (s, 1H), 7.68 (d, J=8.2 Hz, 1H), 8.02 (d, J=8.1 Hz, 1H)

Scheme 13: Synthesis of 1-[(4R,5R,6R,8R)-6-azido-5-hydroxy-6-(hydroxymethyl)-7-oxa-1-thiaspiro[3.4]octan-8-yl]pyrimidine-2,4-dione 44

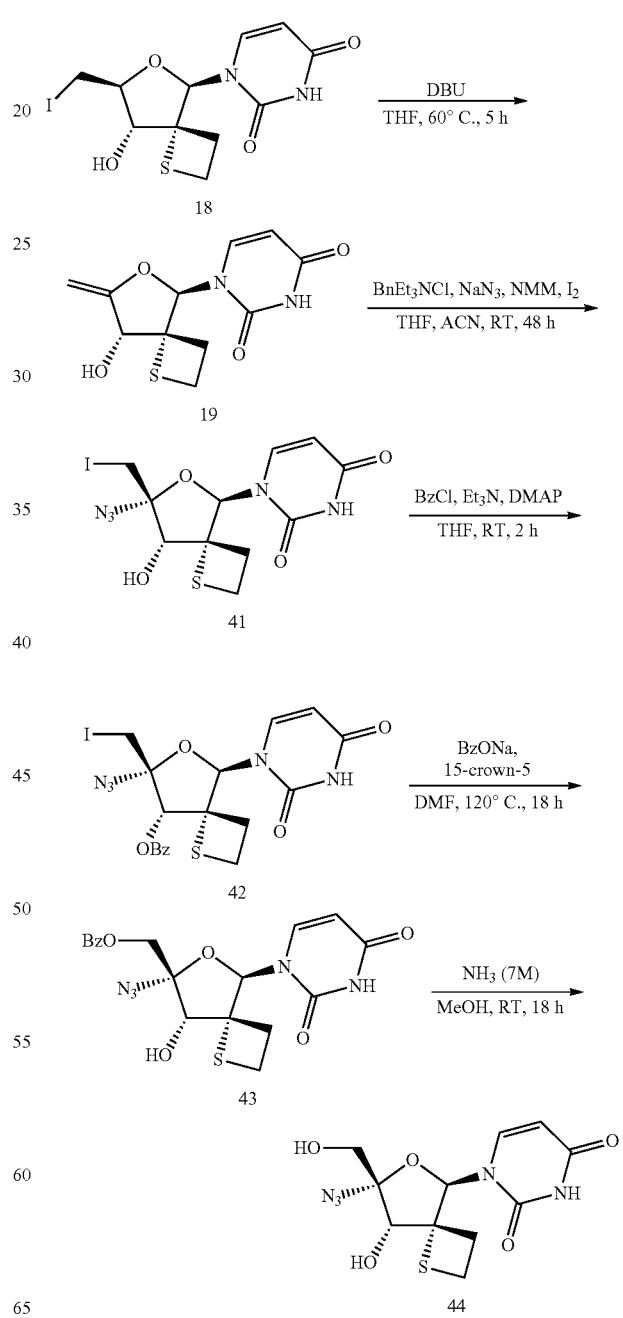

Step 1: Synthesis of 1-((4R,5R,8R)-8-hydroxy-7-methylene-6-oxa-1-thiaspiro[3.4]octan-5-yl)pyrimidine-2,4(1H,3H)-dione 19

Intermediate 18 (5.29 g, 13.352 mmol) was solubilized in THF (150 mL) and added dropwise over 1 h to a stirred solution of DBU (3.174 mL, 1.019 g/mL, 21.245 mmol) in THF (100 mL) at 60° C. The resulting mixture was stirred at 60° C. for 5 h. The reaction mixture was allowed to cool down to RT and poured in water (200 mL). The mixture was acidified until pH=4 with 1M HCl solution. The organic layer was extracted 3 times with EtOAc (200 mL), dried over MgSO$_4$ and concentrated to dryness. The solid was triturated in DCM and filtrated to afford intermediate 19 (2.68 g, yield 75%) as white solid.

MS (ES−): 267.0; $^1$H NMR (400 MHz, DMSO-d$_6$) δ ppm 2.54-2.68 (m, 1H), 2.72-2.84 (m, 1H), 2.91 (td, J=8.5, 5.7 Hz, 1H), 2.94-3.05 (m, 1H), 4.26 (s, 1H), 4.45 (t, J=1.8 Hz, 1H), 4.56 (br d, J=6.2 Hz, 1H), 5.66 (d, J=7.9 Hz, 1H), 6.06 (d, J=6.4 Hz, 1H), 6.51 (s, 1H), 7.33 (d, J=8.1 Hz, 1H), 11.54 (br s, 1H).

Step 2: Synthesis of 1-((4R,5R,7S,8R)-7-azido-8-hydroxy-7-(iodomethyl)-6-oxa-1-thiaspiro[3.4]octan-5-yl)pyrimidine-2,4(1H,3H)-dione 41

N-benzyl-N,N-diethylethanaminium Chloride (BnEt$_3$NCl) (4.585 g, 20.127 mmol) and sodium azide (NaN$_3$) (1.308 g, 20.127 mmol) were suspended in MeCN (30 mL) and stirred for 16 h. The mixture was filtrated into a solution of intermediate 19 (900 mg, 3.355 mmol) and NMM (5.4 mL, 0.917 g/mL, 48.956 mmol) in THF (60 mL). The reaction mixture was cooled to 0° C. and Iodine (5.11 g, 20.127 mmol) in THF (18 mL) was added. The reaction mixture was stirred for 5 h at RT. N-acetyl-cysteine (2 g) was added to the mixture until no gas evolved. Saturated aqueous Na$_2$S$_2$O$_3$ was added to the mixture until a light yellow solution developed. The solution was concentrated under reduced pressure then diluted in EtOAc (50 mL). The organic layer was washed with brine and dried over MgSO$_4$. Solvent was removed and the crude was purified by column chromatography using Heptane/EtOAc as eluent to afford intermediate 41 (1.49 g, yield 99%).

MS (ES−): 436.0; $^1$H NMR (400 MHz, DMSO-d$_6$) δ ppm 2.52-2.61 (m, 1H), 2.76-2.98 (m, 3H), 3.75 (s, 2H), 4.34 (br s, 1H), 5.68 (d, J=8.1 Hz, 1H), 6.47 (br d, J=6.2 Hz, 2H), 7.43-7.57 (m, 1H), 11.57 (s, 1H).

Step 3: Synthesis of (4R,5R,7S,8R)-7-azido-5-(2,4-dioxo-3,4-dihydropyrimidin-1(2H)-yl)-7-(iodomethyl)-6-oxa-1-thiaspiro[3.4]octan-8-yl benzoate 42

Intermediate 41 (1.49 g, 3.408 mmol) was dissolved in THF (45 mL) and the mixture was cooled to 0° C. Et$_3$N (2.368 mL, 0.728 g/mL, 17.04 mmol) and DMAP (8.327 mg, 0.0682 mmol) were added to the mixture followed by the dropwise addition of benzoyl chloride (0.475 mL, 1.211 g/mL, 4.089 mmol). The reaction mixture was stirred for 1.5 h at RT. The reaction mixture was diluted in EtOAc (100 mL). The organic layer was washed with brine, dried over MgSO$_4$ and concentrated. The crude was purified by column chromatography using Heptane/EtOAc as eluent to afford intermediate 42 (1.5 g, yield 81%) as white foam.

MS (ES−): 540.0; $^1$H NMR (400 MHz, DMSO-d$_6$) δ ppm 2.73-2.84 (m, 2H), 2.84-2.94 (m, 1H), 3.02-3.12 (m, 1H), 3.79 (br d, J=11.7 Hz, 1H), 3.92 (br d, J=11.7 Hz, 1H), 5.77 (dd, J=8.0, 2.1 Hz, 1H), 6.02 (br s, 1H), 6.50 (br s, 1H), 7.63 (t, J=7.2 Hz, 2H), 7.72-7.85 (m, 2H), 8.18 (d, J=7.6 Hz, 2H), 11.63 (s, 1H).

Step 4: Synthesis of [(4R,5R,6R,8R)-6-azido-5-benzoyloxy-8-(2,4-dioxopyrimidin-1-yl)-7-oxa-1-thiaspiro[3.4]octan-6-yl]methyl benzoate 43

Intermediate 42 (1.5 g, 2.771 mmol) and BzONa (1.997 g, 13.855 mmol) were suspended in DMF (80 mL) followed by the addition of 15-crown-5 (5.499 mL, 1.11 g/mL, 27.71 mmol). The reaction mixture was stirred overnight at 120° C. The reaction mixture was diluted in EtOAc (100 mL), filtrated over a small bed of decalite and washed with water. The organic layer was dried over MgSO$_4$ and the solvent was removed. The crude was purified by column chromatography using Heptane/EtOAc as eluent to afford intermediate 43 (700 mg, yield 47%) as light yellow solid 63% pure as determined by LC-MS. The compound was used as such.

MS (ES−): 534.1

Step 5: Synthesis of (4R,5R,7R,8R)-7-azido-7-((benzoyloxy)methyl)-5-(2,4-dioxo-3,4-dihydropyrimidin-1(2H)-yl)-6-oxa-1-thiaspiro[3.4]octan-8-yl benzoate 44

Intermediate 43 (700 mg, 1.307 mmol) was dissolved in NH$_3$ (7M in MeOH) (150 mL, 7 M, 1050 mmol) and the mixture was stirred overnight at RT. The reaction mixture was concentrated until dryness and the solid was triturated in Et$_2$O to afford 1-[(4R,5R,6R,8R)-6-azido-5-hydroxy-6-(hydroxymethyl)-7-oxa-1-thiaspiro[3.4]octan-8-yl]pyrimidine-2,4-dione 44 (360 mg, yield 84%) as light yellow solid MS (ES−): 326.0; $^1$H NMR (400 MHz, DMSO-d$_6$) δ ppm 2.38-2.48 (m, 1H), 2.78-2.92 (m, 2H), 3.02-3.10 (m, 1H), 3.69-3.78 (m, 2H), 4.11 (br d, J=5.3 Hz, 1H), 5.67 (d, J=8.1 Hz, 1H), 5.76 (br s, 1H), 5.93 (br d, J=4.2 Hz, 1H), 6.60 (br s, 1H), 7.66 (d, J=8.1 Hz, 1H), 11.31 (br s, 1H).

Scheme 14: Synthesis of isopropyl (2R)-2-[[[(4R,5R,6R,8R)-6-azido-8-(2,4-dioxopyrimidin-1-yl)-5-hydroxy-7-oxa-1-thiaspiro[3.4]octan-6-yl]methoxyphenoxy-phosphoryl]amino]propanoate 45

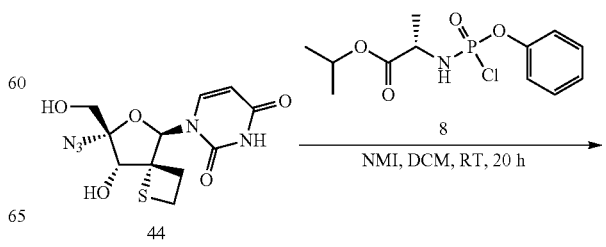

44

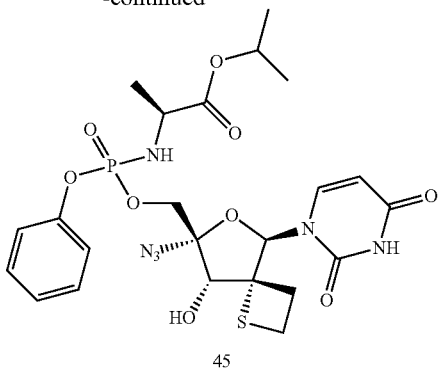

45

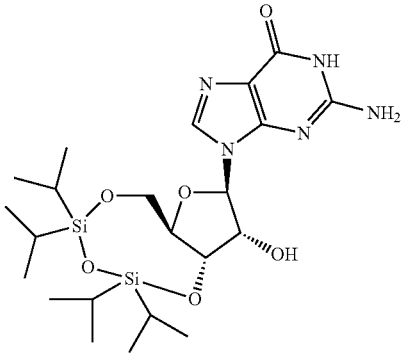

47

Intermediate 44 (200 mg, 0.611 mmol) was dissolved in dry pyridine (5 mL) and the solvent was removed under reduced pressure to obtain a foam. The foam was dissolved in DCM (10 mL) and (0.244 mL, 1.03 g/mL, 3.055 mmol) of N-methylimidazole was added. The reaction mixture was stirred for 5 min at RT under $N_2$ atmosphere. Isopropyl (2R)-2-[[chloro(phenoxy)phosphoryl]amino]propanoate 8 (1M in THF) (0.917 mL, 1 M, 0.917 mmol) was added and the reaction mixture was stirred for 20 h at RT under $N_2$ atmosphere. The reaction mixture was poured in cold water (20 mL) and DCM (20 mL). The aqueous layer was extracted with DCM (3×50 mL). The organic layer was dried over $MgSO_4$ and the solvent was removed under reduced pressure. The crude obtained was purified by Prep HPLC using method E. The obtained fraction was freeze-dried to deliver isopropyl (2R)-2-[[[(4R,5R,6R,8R)-6-azido-8-(2,4-dioxopyrimidin-1-yl)-5-hydroxy-7-oxa-1-thiaspiro[3.4]octan-6-yl]methoxy-phenoxy-phosphoryl]amino]propanoate 45 (80 mg, yield 22%).

MS (ES−): 595.2; $^1$H NMR (400 MHz, DMSO-$d_6$) δ ppm 1.14 (dd, J=6.2, 2.4 Hz, 6H), 1.22 (d, J=7.3 Hz, 3H), 2.52-2.60 (m, 1H), 2.80-2.90 (m, 2H), 2.95-3.04 (m, 1H), 3.72-3.84 (m, 1H), 4.21-4.38 (m, 3H), 4.84 (quind, J=6.3, 6.3, 6.3, 6.3, 4.0 Hz, 1H), 5.60 (dd, J=7.9, 3.3 Hz, 1H), 6.06-6.22 (m, 2H), 6.49-6.62 (m, 1H), 7.15-7.24 (m, 3H), 7.33-7.40 (m, 2H), 7.47 (br d, J=7.0 Hz, 1H), 11.52 (br s, 1H).

Scheme 15: Synthesis of 2-amino-9-((4R,5R,7R,8R)-8-hydroxy-7-(hydroxymethyl)-6-oxa-1-thiaspiro[3,4]octan-5-yl)-1H-purin-6(9H)-one 57

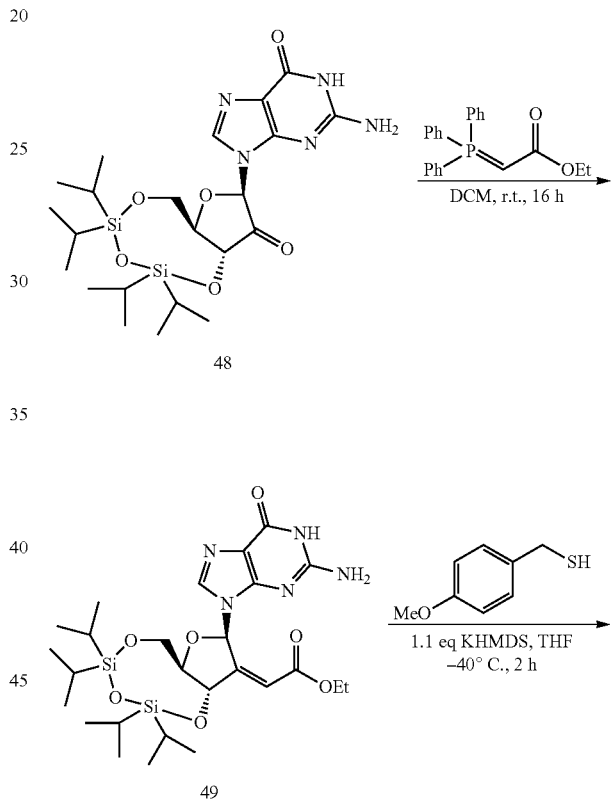

48

49

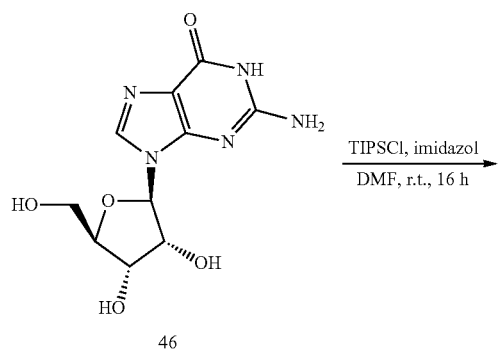

46

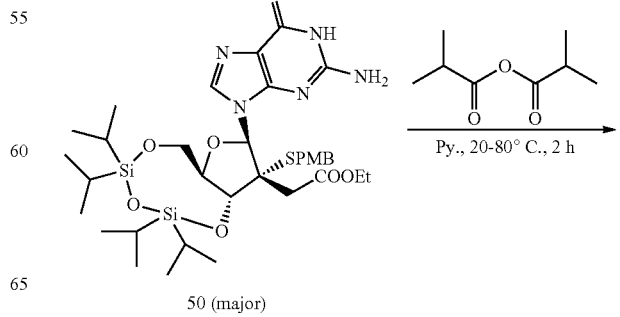

50 (major)

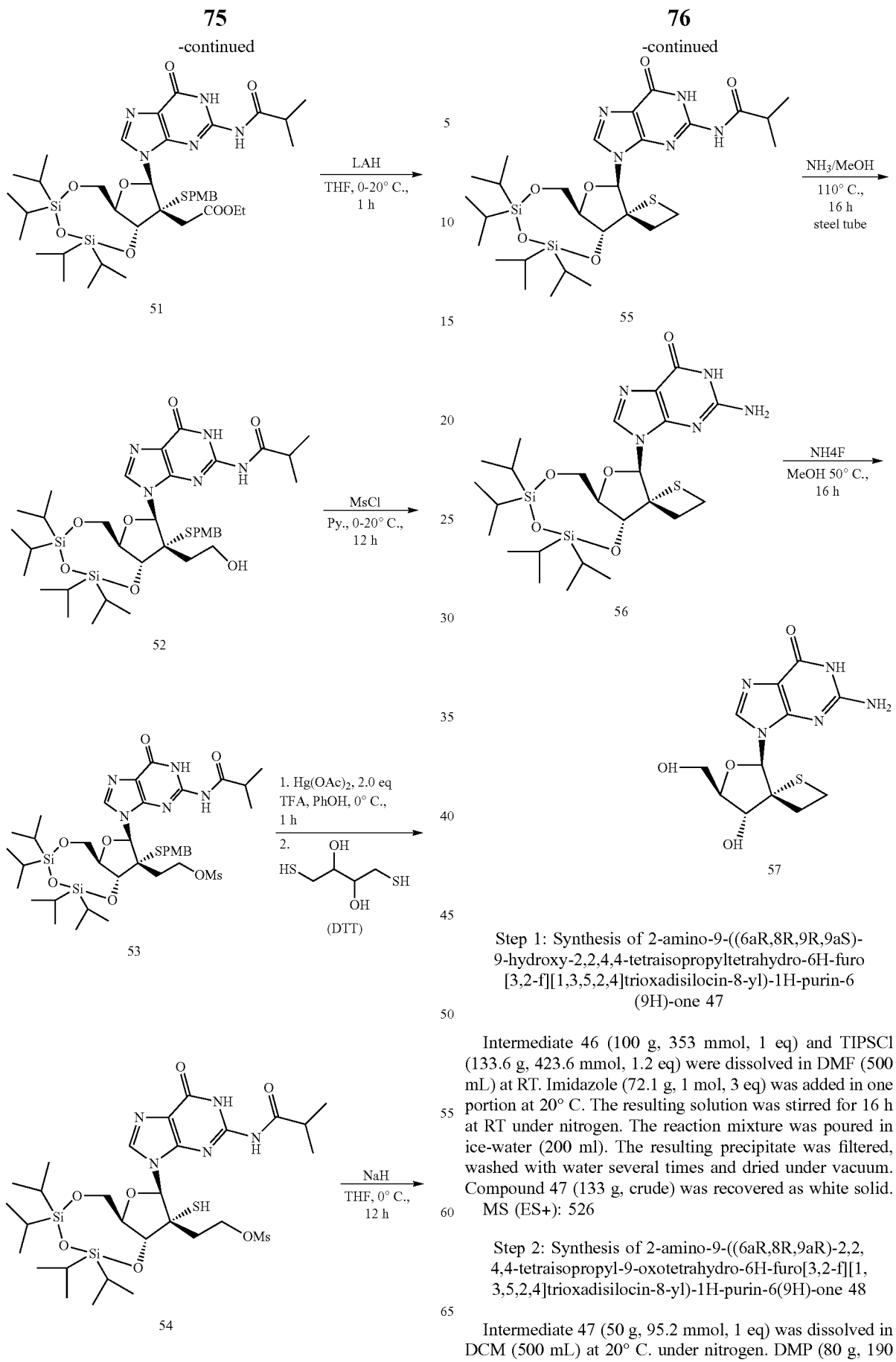

Step 1: Synthesis of 2-amino-9-((6aR,8R,9R,9aS)-9-hydroxy-2,2,4,4-tetraisopropyltetrahydro-6H-furo[3,2-f][1,3,5,2,4]trioxadisilocin-8-yl)-1H-purin-6(9H)-one 47

Intermediate 46 (100 g, 353 mmol, 1 eq) and TIPSCl (133.6 g, 423.6 mmol, 1.2 eq) were dissolved in DMF (500 mL) at RT. Imidazole (72.1 g, 1 mol, 3 eq) was added in one portion at 20° C. The resulting solution was stirred for 16 h at RT under nitrogen. The reaction mixture was poured in ice-water (200 ml). The resulting precipitate was filtered, washed with water several times and dried under vacuum. Compound 47 (133 g, crude) was recovered as white solid. MS (ES+): 526

Step 2: Synthesis of 2-amino-9-((6aR,8R,9aR)-2,2,4,4-tetraisopropyl-9-oxotetrahydro-6H-furo[3,2-f][1,3,5,2,4]trioxadisilocin-8-yl)-1H-purin-6(9H)-one 48

Intermediate 47 (50 g, 95.2 mmol, 1 eq) was dissolved in DCM (500 mL) at 20° C. under nitrogen. DMP (80 g, 190 mmol, 2 eq) was added at 0° C. The resulting mixture was stirred at 20° C. for 16 h under nitrogen. The reaction mixture was poured in an aqueous solution of NaHCO$_3$(100 mL) and aqueous solution of Na$_2$SO$_3$ (100 mL).

The solid was filtered off the filtrate was extracted with DCM (2×100 mL), dried over Na$_2$SO$_4$ and concentrated in vacuum to yield compound 48 (70 g, crude) as dark red solid.

MS (ES+): 524

Step 3: Synthesis of (Z)-ethyl 2-((6aR,8R,9aS)-8-(2-amino-6-oxo-1H-purin-9(6H)-yl)-2,2,4,4-tetraisopropyl-6H-furo[3,2-f][1,3,5,2,4]trioxadisilocin-9(6aH,8H,9aH)-ylidene)acetate 49

Intermediate 48 (70 g, 133.8 mmol, 1 eq) was dissolved in DCM (1 L) at 20° C. under nitrogen.

Ethyl 2-(triphenyl-phosphanylidene)acetate (32.6 g, 93.7 mol, 0.7 eq) was added in one portion at 20° C. The resulting mixture was stirred at 20° C. for 16 h under nitrogen. The reaction mixture was filtered and concentrated and the residue was purified by column chromatography (DCM: MeOH=100/1 to 20:1) to yield compound 49 (39 g, crude) as white solid.

MS (ES+): 595

Step 4: Synthesis of ethyl 2-((6aR,8R,9R,9aR)-8-(2-amino-6-oxo-1H-purin-9(6H)-yl)-2,2,4,4-tetraisopropyl-9-((4-methoxybenzyl)thio)tetrahydro-6H-furo[3,2-f][1,3,5,2,4]trioxadisilocin-9-yl)acetate 50

(4-Methoxyphenyl)methanethiol (38.4 g, 249.2 mmol, 3.7 eq) was dissolved in THF (500 mL) at 20° C. The resulting solution was cooled at −40° C. then KHMDS (1 M, 74.1 mL, 1.1 eq) was added dropwise at −40° C. During the addition, the yellow solution slowly turned into white viscous liquid. The reaction mixture was stirred for 0.5 h after addition, then intermediate 49 (40 g, 67.3 mmol, 1 eq) dissolved in THF (1 L) was added at −40° C. dropwise to the solution. The reaction mixture was allowed slowly to warm up to 20° C. then the stirring was kept for 2 h. The reaction mixture was successively quenched with aqueous HCl (200 mL), extracted with EtOAc (2×200 mL), the organic layer was washed with aqueous NaHCO$_3$ (200 mL) and brine (200 mL), dried over Na$_2$SO$_4$ and evaporated in vacuum. The resulting residue was purified by column chromatography (DCM/MeOH=100/0 to 95/5) to yield compound 50 (12.5 g, crude) as colorless oil.

MS (ES+): 749

Step 5: Synthesis of ethyl 2-((6aR,8R,9R,9aR)-8-(2-isobutyramido-6-oxo-1H-purin-9(6H)-yl)-2,2,4,4-tetraisopropyl-9-((4-methoxybenzyl)thio)tetrahydro-6H-furo[3,2-f][1,3,5,2,4]trioxadisilocin-9-yl)acetate 51

Intermediate 50 (25 g, 33.4 mmol, 1 eq) was dissolved in pyridine (200 mL) at 20° C. then isobutyric anhydride (15.8 g, 100 mmol, 3 eq) was added. The resulting mixture was stirred at 20° C. then TEA (16.9 g, 167.1 mmol, 5 eq) was added slowly. The reaction mixture was then stirred at 80° C. for 2 h, then allowed to cool down to RT and quenched by addition of aqueous solution of NH$_4$Cl (200 mL). The resulting mixture was extracted with EtOAc (2×200 mL). The organic layer was dried over Na$_2$SO$_4$, evaporated in vacuum. The resulting residue was purified by column chromatography (PE/EA=10/1 to 1/1) to yield compound 51 (11.8 g, crude) as brown oil.

MS (ES+): 819

Step 6: Synthesis N-(9-(((6aR,8R,9R,9aR)-9-(2-hydroxyethyl)-2,2,4,4-tetraisopropyl-9-((4-methoxybenzyl)thio)tetrahydro-6H-furo[3,2-f][1,3,5,2,4]trioxadisilocin-8-yl)-6-oxo-6,9-dihydro-1H-purin-2-yl)isobutyramide 52

Intermediate 51 (3 g, 3.6 mmol, 1 eq) was dissolved in THF (30 mL) under nitrogen at 20° C. The resulting solution was cooled to 0° C. then LiAlH$_4$ (417.4 mg, 11 mmol, 3 eq) was added slowly at 0° C. The reaction mixture was stirred at 20° C. for 1 h. The reaction was then successively quenched with aqueous HCl (30 mL), extracted with EtOAc (2×30 mL), washed with aqueous NaHCO$_3$ (20 mL) and brine (20 mL). The organic layer was dried over Na$_2$SO$_4$, and evaporated in vacuum. The resulting residue was purified by column chromatography (DCM/MeOH=100/1 to 50/1). Compound 52 (240 mg, 10% yield) was isolated as yellow solid.

MS (ES+): 777

Step 7: Synthesis of 2-((6aR,8R,9R,9aR)-8-(2-isobutyramido-6-oxo-1H-purin-9(6H)-yl)-2,2,4,4-tetraisopropyl-9-((4-methoxybenzyl)thio)tetrahydro-6H-furo[3,2-f][1,3,5,2,4]trioxadisilocin-9-yl)ethyl methanesulfonate 53

Intermediate 52 (1.6 g, 2 mmol, 1 eq) was dissolved in pyridine (20 mL) at 20° C. The resulting mixture was cooled to 0° C. then MSCl (0.35 g, 3 mmol, 1.5 eq) was added slowly. Then the resulting mixture was stirred at 20° C. for 12 h. The reaction mixture was successively quenched with water (10 mL), extracted with EtOAc (2×10 mL), and the organic layer was dried over Na$_2$SO$_4$ and the solvent was evaporated. The resulting residue was purified by column chromatography (DCM/MeOH=100/1 to 30/1) to yield compound 53 (1.6 g, 90% yield) as yellow oil.

MS (ES+): 854

Step 8: Synthesis of 2-((6aR,8R,9R,9aR)-8-(2-isobutyramido-6-oxo-1H-purin-9(6H)-yl)-2,2,4,4-tetraisopropyl-9-mercaptotetrahydro-6H-furo[3,2-f][1,3,5,2,4]trioxadisilocin-9-yl)ethyl methanesulfonate 54

Intermediate 53 (1.6 g, 1.8 mmol, 1 eq) was dissolved in TFA (1.5 mL) at 25° C. The resulting solution was cooled to 0° C. then mercury acetate (Hg(OAc)$_2$) (1.1 g, 3.7 mmol, 2 eq) and phenol (0.87 g, 9.3 mmol, 5 eq) were added slowly. The resulting dark red solution was stirred at 0° C. for 1 h. Then 1,4-dimercaptobutane-2,3-diol (DTT) (0.57 g, 3.7 mmol, 2 eq) was added at 0° C.

The resulting mixture was stirred for 10 min, filtered over Celite® and washed with EtOAc (10 mL).

The organic layer was mixed with water and the pH of the solution was adjusted to pH-7 with addition of saturated aqueous solution of NaHCO$_3$. The resulting mixture was successively filtered over Celite®, extracted with EtOAc (2×30 mL), and evaporated in vacuum at 25° C. The resulting residue was purified by column chromatography (DCM:MeOH=100:1 to 30:1) to yield compound 54 (2 g, crude) as brown oil.

MS (ES+): 734

Step 9: Synthesis of N-(6-oxo-9-((2'R, 6aR, 8R, 9aR)-2,2,4,4-tetraisopropyltetrahydro spiro[furo[3,2-f][1,3,5,2,4]trioxadisilocine-9,2'-thietan]-8-yl)-6,9-dihydro-1H-purin-2-yl)isobutyramide 55

Intermediate 54 (2 g, 2.7 mmol, 1 eq) was dissolved in THF (20 mL) at 20° C. The resulting mixture was cooled to 0° C. then NaH (0.16 g, 4 mmol, 60% purity, 1.5 eq) was added slowly at 0° C. The reaction mixture (white turbid solution) was stirred at 20° C. for 16 h. The mixture was poured in ice water solution then quenched with aqueous HCl 1M solution (20 mL). The resulting mixture was successively extracted with EtOAc (2×20 mL), dried over $Na_2SO_4$ and evaporated. The resulting residue was purified by column chromatography (DCM/MeOH: 100/0 to 95/5) to yield compound 55 (200 mg, 9.5% yield/2 steps) as yellow oil.

MS (ES+): 637

Step 10: Synthesis of 2-amino-9-((2'R,6aR,8R, 9aR)-2,2,4,4-tetraisopropyltetrahydrospiro[furo[3,2-f][1,3,5,2,4]trioxadisilocine-9,2'-thietan]-8-yl)-1H-purin-6(9H)-one 56

Intermediate 55 (160 mg, 250.8 µmol, 1 eq) was placed in a sealed tube under nitrogen then $MeOH/NH_3$ (4 mL) was added at 20° C. The resulting solution was stirred at 110° C. for 16 h. The reaction mixture was concentrated in vacuum to yield compound 16 (120 mg, crude) as yellow oil.

MS (ES+): 568

Step 11: Synthesis of 2-amino-9-((4R,5R,7R,8R)-8-hydroxy-7-(hydroxymethyl)-6-oxa-1-thiaspiro[3.4] octan-5-yl)-1H-purin-6(9H)-one 57

Intermediate 56 (120 mg, 211 µmol, 1 eq) was dissolved in MeOH (5 mL) at 20° C. under nitrogen then $NH_4F$ (23.5 mg, 633 µmol, 3 eq) was added. The reaction mixture was stirred at 50° C. for 16 h, then it was concentrated. The resulting residue was purified by prep HPLC to yield compound 57 (20 mg, 29% yield) as white solid.

MS (ES+): 326; $^1$H NMR (400 MHz, MeOD): δ 7.93 (s, 1H), 6.19 (s, 1H), 4.43 (d, J=5.6 Hz, 1H), 3.76-3.74 (m, 2H), 3.74-3.73 (m, 1H), 3.67-3.65 (m, 1H), 2.90-2.87 (m, 2H), 2.76-2.73 (m, 1H).

Scheme 16: Synthesis of (4R,5R,7R,8R)-5-(6-amino-9H-purin-9-yl)-7-(hydroxymethyl)-6-oxa-1-thiaspiro[3.4]octan-8-ol 67

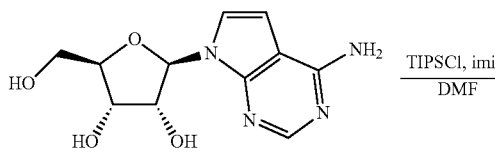

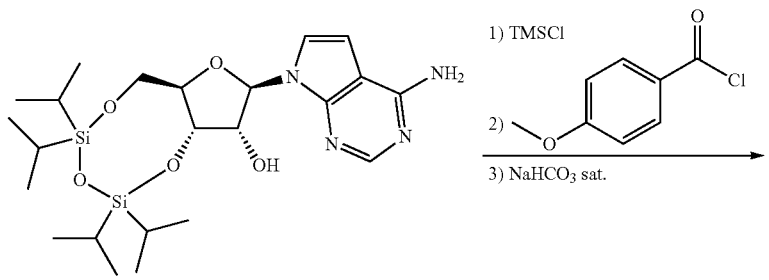

58

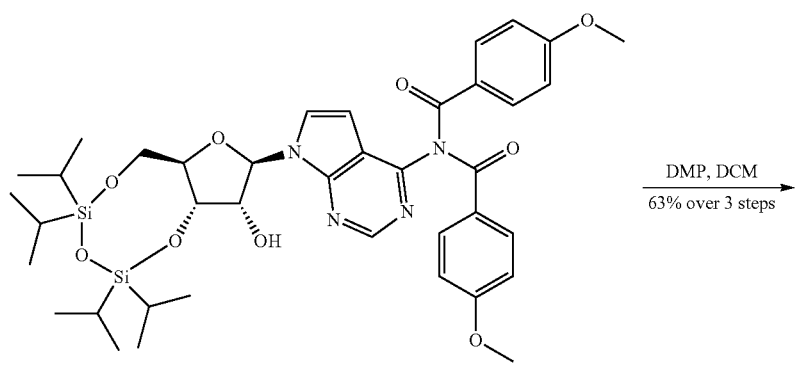

59

-continued
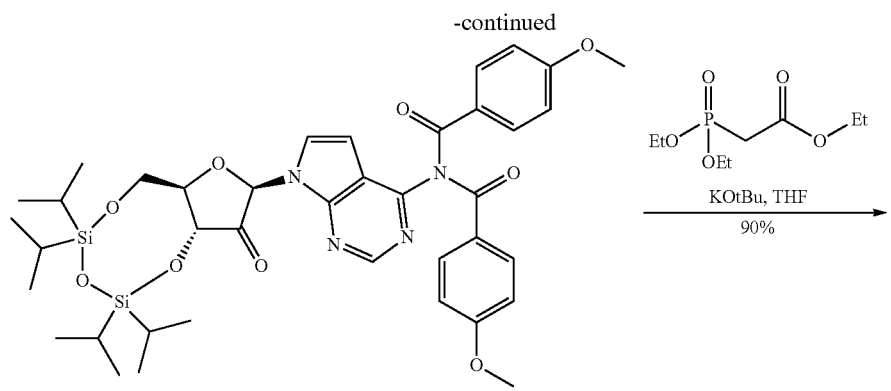
60
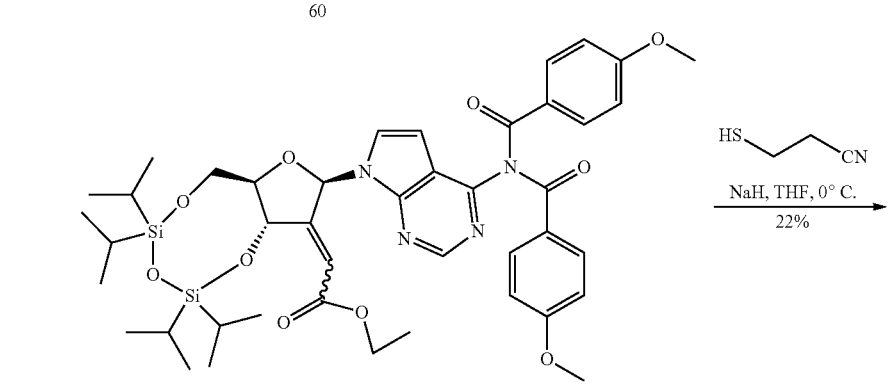
61
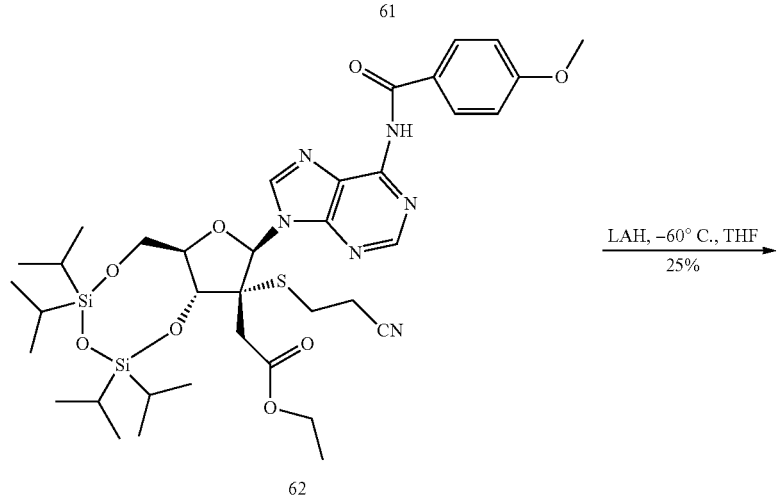
62
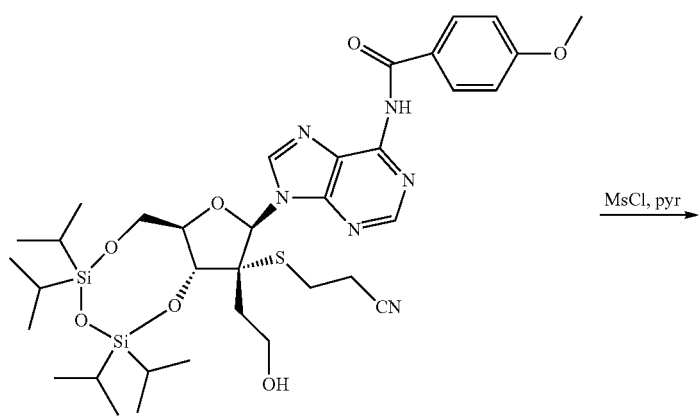
63

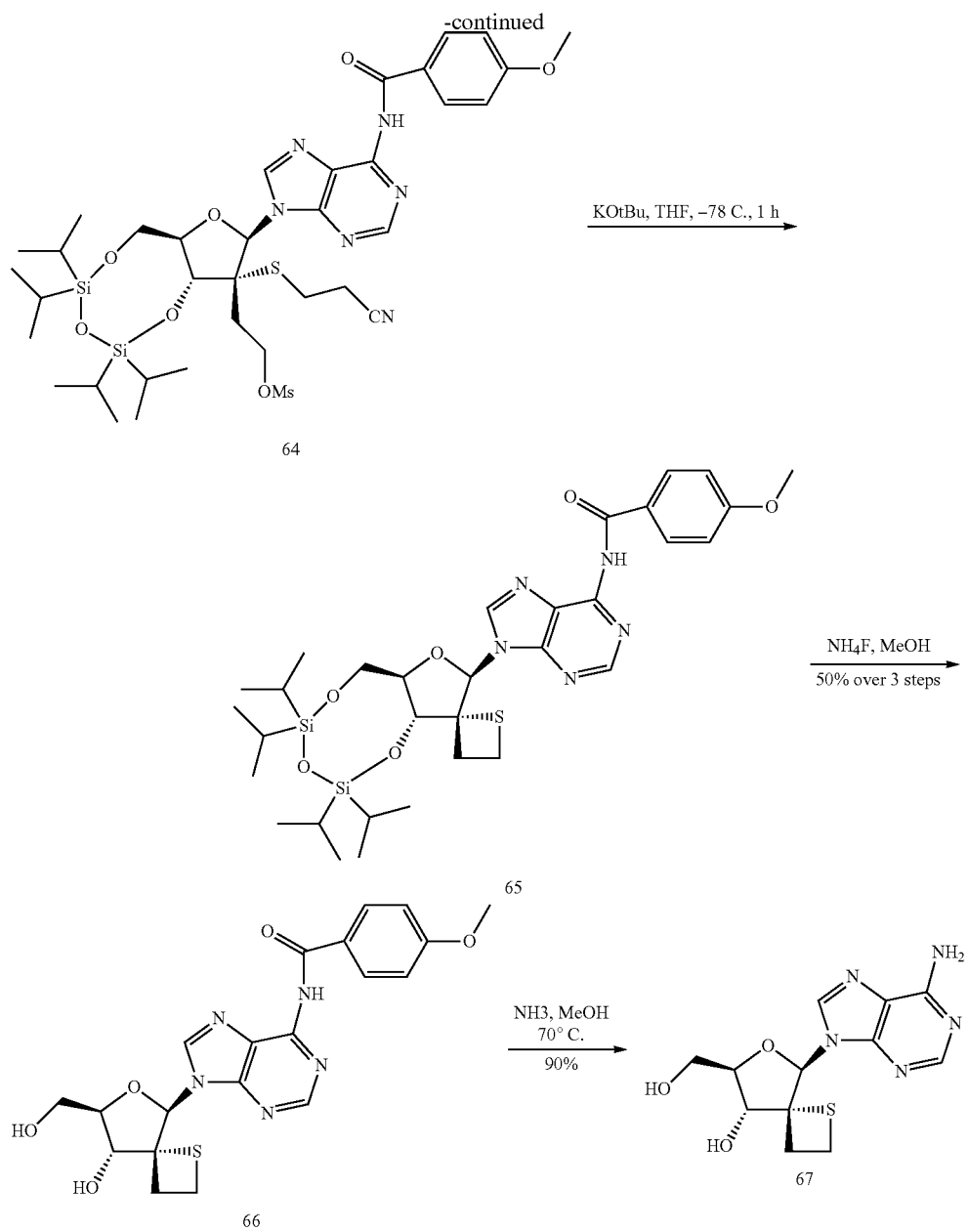

Step 1: (6aR,8R,9R,9aS)-8-(6-amino-9H-purin-9-yl)-2,2,4,4-tetraisopropyltetrahydro-6H-furo[3,2-f][1,3,5,2,4]trioxadisilocin-9-ol 58

To a solution of adenosine (20 g, 74.838 mmol) and imidazole (7.642 g, 112.257 mmol) in dry DMF (100 mL) at r.t. was added 1,3-dichloro-1,1,3,3-tetraisopropyldisiloxane (26.335 mL, 0.986 g/mL, 82.322 mmol) under nitrogen atmosphere. The mixture was stirred at r.t. for 2 h.

The mixture was poured into a mixture of ice and water (200 mL), and then extracted with EtOAc (2×300 mL). The organic layer was successively washed with brine (4×300 mL), dried over $Na_2SO_4$, filtered and concentrated to afford crude intermediate 58 as white foam (41.3 g) that was used as such for the next step.

$^1$H NMR (400 MHz, DMSO-$d_6$) δ ppm 1.01-1.09 (m, 28H), 3.91-3.96 (m, 1H), 4.00 (dt, J=8.5, 2.9 Hz, 1H), 4.04 (d, J=3.3 Hz, 1H), 4.52 (t, J=4.5 Hz, 1H), 4.80 (dd, J=8.5, 5.2 Hz, 1H), 5.59 (d, J=4.6 Hz, 1H), 5.87 (d, J=1.1 Hz, 1H), 7.29 (s, 2H), 8.07 (s, 1H), 8.20 (s, 1H)

MS (ES+): 560.3,

Step 2: N-(9-((6aR,8R,9R,9aS)-9-hydroxy-2,2,4,4-tetraisopropyltetrahydro-6H-furo[3,2-f][1,3,5,2,4]trioxadisilocin-8-yl)-9H-purin-6-yl)-4-methoxy-N-(4-methoxybenzoyl)benzamide 59

To a solution of crude intermediate 58 (20.5 g, 36.194 mmol) in dry pyridine (150 mL) was added at 20° C. under nitrogen atmosphere TMSCl (19.43 mL, 0.85 g/mL, 152.015 mmol). After 1 h 30 of stirring at r.t., paramethoxybenzoyl chloride (24.698 g, 144.776 mmol) was added. The resulting mixture was stirred at r.t. overnight. The reaction mixture was cooled with an ice bath and 10 mL of water was added.

After 5 min, a saturated aqueous solution of NaHCO$_3$ (200 mL) was added and the mixture was stirred at 40° C. overnight.

The resulting mixture was extracted with EtOAc (3×500 mL). The organic layers were successively combined, washed with an aqueous solution of HCl 1M (2×500 mL), brine (3×500 mL), dried over Na$_2$SO$_4$, filtered and concentrated to afford crude intermediate 59 (39.18 g) as a yellow solid.

MS (ES+): 778.5,

Step 3: 4-methoxy-N-(4-methoxybenzoyl)-N-(9-((6aR,8R,9aR)-2,2,4,4-tetraisopropyl-9-oxotetrahydro-6H-furo[3,2-f][1,3,5,2,4]trioxadisilocin-8-yl)-9H-purin-6-yl)benzamide 60

To a solution of crude intermediate 59 (38.5 g, 35.381 mmol) in dry dichloromethane (400 mL) was added Dess-Martin periodinane (45.021 g, 106.144 mmol) at r.t. under nitrogen atmosphere. The resulting mixture was stirred at r.t. overnight.

Then was diluted with dichloromethane (200 mL), washed with water (200 mL), and the water layer was extracted with DCM (200 mL). The organic layers were successively combined, washed with a saturated solution of NaHCO$_3$ (200 mL), brine (2×200 mL), dried over Na$_2$SO$_4$, filtered and concentrated.

The crude residue was purified by silica gel chromatography column (heptane/EtOAc, 10/0 to 6/4) to afford intermediate 60 as a white foam (17.11 g, 22.04 mmol, 63% over 3 steps). Intermediate 60 is obtained as a ketone, and as a hydrated ketone, and both are reactive in the Wittig reaction that follows.

$^1$H NMR (400 MHz, DMSO-d$_6$) δ ppm 0.99-1.19 (m, 28H), 3.80 (d, J=1.1 Hz, 6H), 3.82-3.85 (m, 1H), 3.95-4.06 (m, 2H), 5.36 (d, J=9.7 Hz, 1H), 6.32 (s, 1H), 6.98-7.03 (m, 4H), 7.71-7.76 (m, 4H), 8.47 (s, 1H), 8.81 (s, 1H)

MS (ES+): 776.3,

Step 4: ethyl 2-((6aR,8R,9aS)-2,2,4,4-tetraisopropyl-8-(6-(4-methoxy-N-(4-methoxybenzoyl)benzamido)-9H-purin-9-yl)dihydro-6H-furo[3,2-f][1,3,5,2,4]trioxadisilocin-9(8H)-ylidene)acetate 61

To a solution of triethyl phosphonoacetate (4.404 mL, 1.13 g/mL, 22.197 mmol) in Me-THF (250 mL) was added potassium tert-butoxide (2.874 g, 25.612 mmol) at −10° C. ~−5° C., and the mixture was stirred for 30 min. To this mixture was added dropwise a solution of intermediate 60 (13.25 g, 17.075 mmol) in Me-THF (250 mL) and it was allowed to warm up to r.t. and stirred for 1 h.

Water was added (100 mL) and the mixture was extracted with EtOAc (3×200 mL). Organic layers were combined, washed with brine (2×200 mL), dried over Na$_2$SO$_4$, filtered and concentrated. The residue was dissolved in DCM, and purified by silica gel column chromatography (hept/EtOAc, 9/1 to 6/4) to afford intermediate 61 as a white foam (13.03 g, 15.4 mmol, Z/E mixture, 90%).

Z: $^1$H NMR (400 MHz, DMSO-d$_6$) δ ppm 1.00-1.28 (m, 31H), 3.73-3.86 (m, 6H), 3.96-4.19 (m, 5H), 5.75-5.82 (m, 1H), 5.98-6.05 (m, 1H), 6.94-7.04 (m, 5H), 7.70-7.78 (m, 4H), 8.65 (s, 1H), 8.66-8.70 (m, 1H)

E: $^1$H NMR (400 MHz, DMSO-d$_6$) δ ppm 1.00-1.30 (m, 31H), 3.74-3.85 (m, 6H), 3.94-4.18 (m, 5H), 5.75-5.79 (m, 1H), 6.02 (t, J=2.2 Hz, 1H), 6.97-7.02 (m, 5H), 7.71-7.76 (m, 4H), 8.64 (s, 1H), 8.68 (s, 1H)

MS (ES+): 846.5,

Step 5: ethyl 2-(((6aR,8R,9R,9aR)-9-((2-cyanoethyl)thio)-2,2,4,4-tetraisopropyl-8-(6-(4-methoxybenzamido)-9H-purin-9-yl)tetrahydro-6H-furo[3,2-f][1,3,5,2,4]trioxadisilocin-9-yl)acetate 62

To a solution of 3-mercaptopropiononitrile (3.605 g, 41.366 mmol) in dry THF (100 mL) was added NaH (60% dispersion in mineral oil) (1.985 g, 49.64 mmol) at 0° C. under nitrogen atmosphere, and mixture was stirred for 30 min. To this mixture was added at 0° C. intermediate 61 (7 g, 8.273 mmol). The reaction mixture was stirred at 0° C. for 2 h.

The reaction mixture was poured slowly in a saturated aqueous solution of NH$_4$Cl and ice (100 mL), diluted with EtOAc (100 mL), and an aqueous solution of HCl 1M was added until pH 7. The two layers were separated, and the aqueous layer was extracted with EtOAc (2×100 mL). The organic layers were successively combined, washed with brine (2×100 mL), dried over Na$_2$SO$_4$, filtered and concentrated.

The crude residue was purified by silica gel column chromatography (Heptane/EtOAc, 10/0 to 6/4) to afford intermediate 62 as white foam (1.43 g, 1.789 mmol, 22%).

$^1$H NMR (400 MHz, DMSO-d$_6$) δ ppm 0.98-1.29 (m, 31H), 2.81-3.00 (m, 4H), 3.23 (m, 2H), 3.54-3.77 (m, 2H), 3.86 (s, 3H), 3.94-4.13 (m, 2H), 4.30 (br dd, J=7.9, 2.6 Hz, 1H), 5.72 (br d, J=7.9 Hz, 1H), 6.41 (s, 1H), 7.08 (d, J=8.6 Hz, 2H), 8.03 (d, J=8.8 Hz, 2H), 8.46 (s, 1H), 8.68 (s, 1H), 11.07 (s, 1H)

MS (ES+): 799.7,

Step 6: N-(9-((6aR,8R,9R,9aR)-9-((2-cyanoethyl)thio)-9-(2-hydroxyethyl)-2,2,4,4-tetraisopropyltetrahydro-6H-furo[3,2-f][1,3,5,2,4]trioxadisilocin-8-yl)-9H-purin-6-yl)-4-methoxybenzamide 63

To a solution of intermediate 62 (1.43 g, 1.789 mmol) in dry THF (50 mL) was added dropwise LAH (1M in THF) (8.947 mL, 8.947 mmol) at −60° C. under nitrogen atmosphere. The resulting mixture was stirred at −60° C. overnight.

A saturated aqueous solution of NH$_4$Cl (30 mL) was added dropwise at −60° C. to the reaction mixture. The resulting mixture was then allowed to slowly heat back to r.t. and EtOAc (50 mL) was added. The two layers were separated, and the aqueous layer was extracted with EtOAc (2×50 mL). The organic layers were successively combined, washed with brine (2×80 mL), dried over Na$_2$SO$_4$, filtered and concentrated.

The crude residue was purified by column chromatography (Hept/EtOAc, 1/9 to 0/10) to afford intermediate 63 as yellowish foam (285 mg, 0.376 mmol, 21%).

MS (ES+): 757.7,

Step 7: 2-46aR,8R,9R,9aR)-9-((2-cyanoethyl)thio)-2,2,4,4-tetraisopropyl-8-(6-(4-methoxybenzamido)-9H-purin-9-yl)tetrahydro-6H-furo[3,2-f][1,3,5,2,4]trioxadisilocin-9-yl)ethyl methanesulfonate 64

To a solution of intermediate 63 (427 mg, 0.564 mmol) in dry pyridine (15 mL) was added MSCl (0.0657 mL, 1.475 g/mL, 0.846 mmol) at r.t. The resulting mixture was stirred at r.t. for 1 h under nitrogen atmosphere.

The solvent was evaporated and the resulting residue was dissolved in ethyl acetate (10 mL), then washed with a saturated aqueous solution of NaHCO₃ (10 mL). The aqueous layer was extracted with ethyl acetate (2×10 mL). The combined organic layers were successively washed with brine (2×10 mL), dried over Na₂SO₄, filtered and concentrated to afford intermediate 64 as a crude yellow foam (471 mg), that was used immediately for the following step, as it is unstable.

MS (ES+): 835.5,

Step 8: 4-methoxy-N-(9-((6aR,8R,9R,9aR)-2,2,4,4-tetraisopropyldihydro-6H,8H-spiro[furo[3,2-f][1,3,5,2,4]trioxadisilocine-9,2'-thietan]-8-yl)-9H-purin-6-yl)benzamide 65

To a solution of crude intermediate 64 (471 mg, 0.564 mmol) in dry THF (15 mL) at −78° C. under nitrogen atmosphere was added dropwise a cold solution of KOtBu in THF (1.128 mL, 1 M, 1.128 mmol). The resulting mixture was stirred at −78° C. for 10 min.

The reaction mixture was quenched by pouring a saturated aqueous solution of NH₄Cl (5 mL) at −78° C. and the mixture was allowed to warm up slowly to r.t. EtOAc (20 mL) was added, the two layers were separated, and the water layer was extracted using EtOAc (2×20 mL). The organic layers were successively combined, washed with brine (20 mL), dried over Na₂SO₄, filtered and concentrated to afford crude intermediate 65 (380 mg). The crude contains 65, and 65 hydrolyzed in the 5' position. Both intermediates react in the same way in the next step.

MS (ES+): 686.5,

Step 9: N-(9-((4R,5R,7R,8R)-8-hydroxy-7-(hydroxymethyl)-6-oxa-1-thiaspiro[3.4]octan-5-yl)-9H-purin-6-yl)-4-methoxybenzamide 66

To a solution of crude intermediate 65 (380 mg, 0.554 mmol) in MeOH (10 mL) was added ammonium fluoride (0.205 g, 5.539 mmol) at r.t. under nitrogen atmosphere. The resulting mixture was stirred overnight at r.t.

The resulting mixture was diluted with water (20 mL) and EtOAc (20 mL). The two layers were separated, and the water layer was extracted using EtOAc (3×20 mL). The organic layers were successively combined, washed with brine (20 mL), dried over Na₂SO₄, filtered and concentrated.

The crude residue was purified by column chromatography (DCM/MeOH, 1% to 6%) to afford intermediate 66 as a white foam (140 mg, 0.278 mg, 88% pure, 50% over 3 steps).

MS (ES+): 444.3,

Step 10: (4R,5R,7R,8R)-5-(6-amino-9H-purin-9-yl)-7-(hydroxymethyl)-6-oxa-1-thiaspiro[3.4]octan-8-ol67

Intermediate 66 (140 mg, 0.278 mmol) was dissolved in NH₃ (7M in MeOH) (15 mL, 7 M, 105 mmol) and the reaction mixture was stirred at 70° C. for 10 h.

The resulting mixture was evaporated and the residue was purified by column chromatography (DCM/NH₃ (7M in MeOH), 3% to 9%) to afford pure product as white powder (77.1 mg, 0.249 mmol, 90%).

$^1$H NMR (400 MHz, DMSO-d₆) δ ppm 2.28 (ddd, J=12.5, 8.7, 5.6 Hz, 1H), 2.68 (ddd, J=12.4, 8.5, 6.8 Hz, 1H), 2.82-2.92 (m, 2H), 3.55 (dt, J=7.6, 3.0 Hz, 1H), 3.64 (dt, J=12.3, 4.4 Hz, 1H), 3.72-3.82 (m, 1H), 4.32 (br d, J=5.1 Hz, 1H), 5.23 (t, J=5.2 Hz, 1H), 5.70-5.77 (m, 1H), 6.55 (s, 1H), 7.32 (s, 2H), 8.20 (s, 1H), 8.46 (s, 1H)

$^{13}$C NMR (101 MHz, DMSO-d₆) δ ppm 19.11 (s, 1C), 30.15 (s, 1C), 59.48 (s, 1C), 60.86 (s, 1C), 72.17 (s, 1C), 82.31 (s, 1C), 91.32 (s, 1C), 118.56 (s, 1C), 138.68 (s, 1 C), 149.34 (s, 1C), 152.75 (s, 1C), 156.05 (s, 1C)

MS (ES+): 310.2,

Synthesis of Nucleoside 5'-Triphosphates

Dry nucleoside (0.05 mmol) was dissolved in dry PO(OMe)₃ (0.7 mL) N-Methylimidazole (0.009 mL, 0.11 mmol) was added followed by POCl₃ (0.009 mL, 0.11 mmol), and the mixture was kept at R.T. for 20-40 mins. The reaction was controlled by LCMS and monitored by the appearance of corresponding nucleoside 5'-monophosphate. After completion of the reaction, tetrabutylammonium salt of pyrophosphate (150 mg) was added, followed by DMF (0.5 mL) to get a homogeneous solution. After 1.5 h at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH7.5). Triphosphate was eluted at 75-80% B. Corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

| Co. No. | Structure | MS (M-1) | P(α) | P(β) | P(γ) |
|---|---|---|---|---|---|
| 58 | 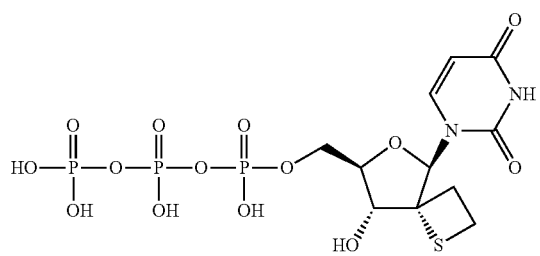 [SMILES: O=c1ccn([C@@H]2O[C@H](COP(=O)(O)OP(=O)(O)OP(=O)(O)O)[C@@H](O)[C@]23CCS3)c(=O)[nH]1] | 524.7 | −11.67 (d) | −23.34 (t) | −10.83 (d) |

-continued

| Co. No. | Structure | MS (M-1) | P(α) | P(β) | P(γ) |
|---|---|---|---|---|---|
| 59 | 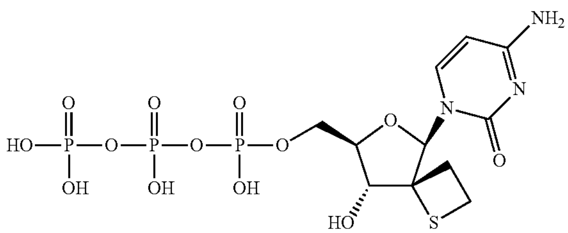 [SMILES: Nc1ccn([C@@H]2O[C@H](COP(=O)(O)OP(=O)(O)OP(=O)(O)O)[C@@H](O)[C@]23CCS3)c(=O)n1] | 524.4 | −11.57 (d) | −23.25 (t) | −10.89 (d) |
| 60 | 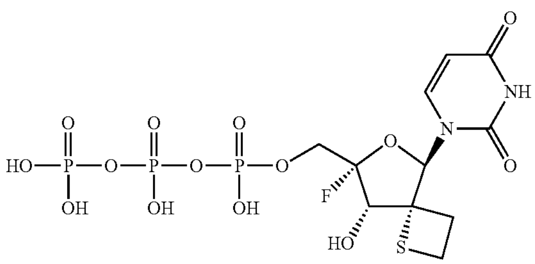 [SMILES: O=c1ccn([C@@H]2O[C@](F)(COP(=O)(O)OP(=O)(O)OP(=O)(O)O)[C@@H](O)[C@]23CCS3)c(=O)[nH]1] | 542.6 | −12.38 (d) | −23.33 (t) | −10.98 (d) |
| 61 | 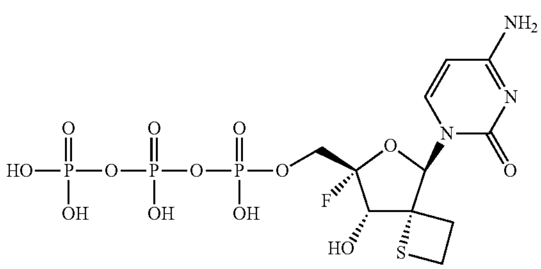 [SMILES: Nc1ccn([C@@H]2O[C@](F)(COP(=O)(O)OP(=O)(O)OP(=O)(O)O)[C@@H](O)[C@]23CCS3)c(=O)n1] | 541.3 | −12.33 (d) | −23.32 (t) | −10.97 (d) |
| 62 | 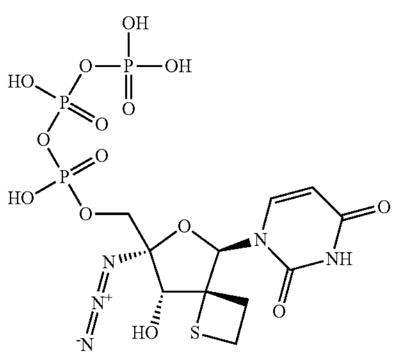 | 565.9 | −12.42 (d) | −23.35 (t) | −11.01 (d) |
| 63 | 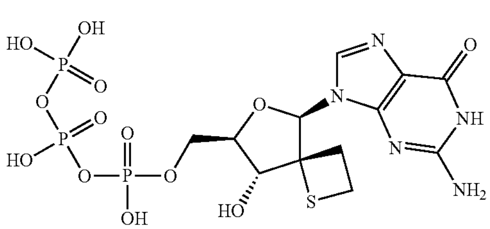 [SMILES: Nc1nc2c(ncn2[C@@H]2O[C@H](COP(=O)(O)OP(=O)(O)OP(=O)(O)O)[C@@H](O)[C@]23CCS3)c(=O)[nH]1] | 564.4 | −11.50 (d) | −23.38 (t) | −11.02 (d) |

Biological Examples

Replicon Assay

The compounds of Formula (I) were examined for activity against HCV in a cellular assay. The assay was used to demonstrate that the compounds of Formula (I) inhibited a HCV functional cellular replicating cell line, also known as HCV replicons. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an internal ribosome entry site (IRES) from encephalomyocarditis virus (EMCV), preceded by a reporter portion (FfL-luciferase), and a selectable marker portion (neo$^R$, neomycine phosphotransferase). The construct is bordered by 5' and 3' NTRs (non-translated regions) from HCV genotype 1b. Continued culture of the replicon cells in the presence of G418 (neo$^R$) is dependent on the replication of the HCV-RNA. The stably transfected replicon cells that express HCV-RNA, which replicates autonomously and to high levels, encoding inter alia luciferase, were used for screening the antiviral compounds.

The replicon cells were plated in 384-well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease the level of detected luciferase activity by 50%, or more specifically, the ability of the genetically linked HCV replicon RNA to replicate.

Antiviral Activity Against DENV-2/16681/eGFP in Vero AND Huh-7 Cells

Methods

The antiviral activity of the compounds against DENV-2/16681/eGFP was determined in a phenotypic antiviral assay with eGFP read-out, a measure for the amount of virus (TV-WI-03476 and TV-WI-05601). In parallel, cytotoxicity of the compounds was measured using ATPLite™ (PerkinElmer, Waltham, Mass.). The assay was performed in two different cell-lines (Vero and Huh-7) to exclude cell-specific activity of the compound.

DENV-2/16681/eGFP was produced by the transfection of the in vitro transcribed RNA of plasmid pFK-DVs-G2A (purchased from Prof. R. Bartenschlager, University of Heidelberg, Germany; FIG. 1) into Huh-7 cells (human hepatocarcinoma cells; kindly provided by Prof. R. Bartenschlager) (TV-WI-04247).

In brief, 2,500 Vero cells (African green monkey kidney cells; European Collection of Cell Cultures [ECACC], Porton Down, UK; catalogue number 84113001) or Huh-7 cells were seeded in 384-well plates containing 9-fold serially diluted test compound. After incubating 24 h at 37° C., Vero and Huh-7 cells were infected with DENV-2/16681/eGFP at a multiplicity of infection (MOI) of 1 and 5, respectively.

After 3 days of incubation at 37° C., the viral replication was quantified by measuring eGFP expression in the cells with a laser microscope. The 50% effective concentration ($EC_{50}$) was defined as the concentration inhibiting 50% of the eGFP expression of the compound-treated DENV-infected cells vs. the untreated DENV-infected cells (virus control), using the cell controls as baseline of eGFP signal (i.e., 0% signal). In the same way, the 90% effective concentration ($EC_{90}$) was calculated.

In parallel, cytotoxic effects of the compounds (50% cytotoxic concentration [$CC_{50}$] and 90% cytotoxic concentration [$CC_{90}$]) were evaluated using an ATPlite cell viability luminescence assay (PerkinElmer). To this end, ATPlite was added to the wells according to the supplier's instructions once the eGFP read-out was performed, and the luminescence was measured; a measure directly relating to the number of viable cells. The $CC_{50}$ was determined as the 50% inhibitory concentration for the luminescent signal in compound-treated DENV-infected cells compared to untreated DENV-infected cells (virus control), using a medium control as baseline of emitted light (i.e., 0% signal).

Dengue Virus Polymerase Inhibition Assay

The enzyme activity of dengue virus NS5 polymerase domain (DENVpol, serotype 2, New Guinea C strain) is measured as an incorporation of tritiated NMP into acid-insoluble RNA products. DENVpol assay reactions contain recombinant enzyme, heteropolymeric RNA, about 0.5 µCi tritiated NTP, 0.33 µM of competing cold NTP, 40 mM HEPES (pH 7.5), 3 mM dithiothreitol, and 2 mM $MgCl_2$. Standard reactions are incubated for 3 hours at 30° C., in the presence of increasing concentration of inhibitor. At the end of the reaction, RNA is precipitated with 10% TCA, and acid-insoluble RNA products are filtered on a size exclusion 96-well plate. After washing of the plate, scintillation liquid is added and radiolabeled RNA products are detected according to standard procedures with a Trilux Topcount scintillation counter. The compound concentration at which the enzyme-catalyzed rate is reduced by 50% ($IC_{50}$) is calculated by fitting the data to a non-linear regression (sigmoidal).

Assay Principle and Method Against CHIKV

The antiviral activities of the nucleoside analogs against chikungunya virus (CHIKV) were tested using a cell-based high-throughput CPE (cytopathic effect) inhibition assay. In this assay, CHIKV strain S27 and Huh7 cells (a human hepatoma cell line) were employed. The test compounds were prepared in a 9-point fourfold serial dilutions and plated in a 384-well plate. Then, a density of 8000 cells/well and an MOI (Multiplicity of Infection) of 0.25 CHIKV were added to each well. The plates were incubated at 37° C./5% $CO_2$ for 2 days. The antiviral activity of a test compound was measured by addition of an ATPLite™ 1-step kit (PerkinElmer), which measures the ATP levels in live cells protected from viral CPE by a test compound. The cytotoxicity of test compounds was measured in parallel in the absence of virus infection. The readout is luminescence.

Results

Table 1A shows the antiviral data obtained against HCV, DV and CHIKV and cellular toxicity.

TABLE 1A

| | | HCV Huh-7 (EC$_{50}$, μM) | DENV Huh-7 (EC$_{50}$, μM) | Tox Huh-7 (CC$_{50}$, μM) | DENV Vero (EC$_{50}$, μM) | Tox Vero (CC$_{50}$, μM) | CHIKV Huh-7 (EC$_{50}$, μM) |
|---|---|---|---|---|---|---|---|
| Co. No. | Structure | | | | | | |
| 7 | | >100 | — | >100 | >100 | >100 | — |
| 9 | | 1 | 9 | >100 | >100 | >100 | 18 |
| 10 | | >100 | >100 | >100 | >100 | >100 | >100 |
| 11 | | >100 | >100 | >100 | >100 | >100 | >100 |

TABLE 1A-continued

Antiviral activity of selected compounds (cell based assays)

| Co. No. | Structure | HCV Huh-7 (EC$_{50}$, μM) | DENV Huh-7 (EC$_{50}$, μM) | Tox Huh-7 (CC$_{50}$, μM) | DENV Vero (EC$_{50}$, μM) | Tox Vero (CC$_{50}$, μM) | CHIKV Huh-7 (EC$_{50}$, μM) |
|---|---|---|---|---|---|---|---|
| 12 | 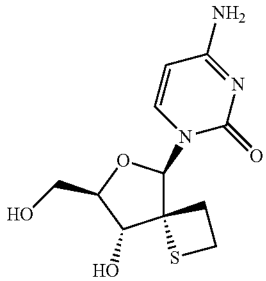 [SMILES: Nc1ccn([C@@H]2O[C@H](CO)[C@@H](O)[C@]23CCS3)c(=O)n1] | >100 | >100 | >100 | >100 | >100 | >100 |
| 17 | 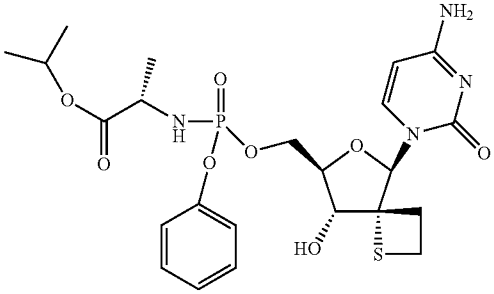 [SMILES: CC(C)OC(=O)[C@H](C)NP(=O)(OC[C@H]1O[C@@H](n2ccc(N)nc2=O)[C@@]2(CCS2)[C@@H]1O)Oc1ccccc1] | >50 | 19 | >50 | >50 | >50 | >50 |
| 22 | 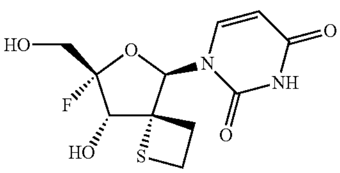 [SMILES: O=c1ccn([C@@H]2O[C@](F)(CO)[C@@H](O)[C@]23CCS3)c(=O)[nH]1] | 84 | 69 | >100 | 63 | >100 | >100 |
| 23 | 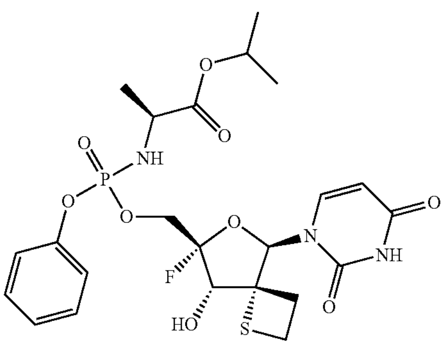 [SMILES: CC(C)OC(=O)[C@H](C)NP(=O)(OC[C@@]1(F)O[C@@H](n2ccc(=O)[nH]c2=O)[C@@]2(CCS2)[C@@H]1O)Oc1ccccc1] | 2 | 14 | >100 | 85 | >100 | 3 |
| 25 | 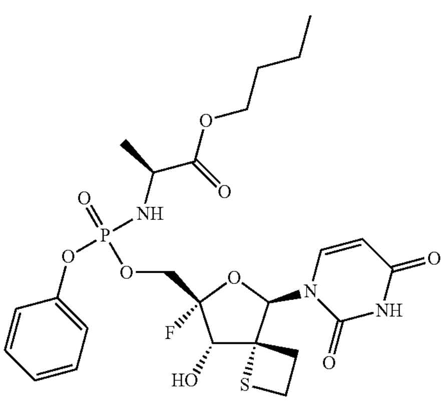 [SMILES: CCCCOC(=O)[C@H](C)NP(=O)(OC[C@@]1(F)O[C@@H](n2ccc(=O)[nH]c2=O)[C@@]2(CCS2)[C@@H]1O)Oc1ccccc1] | 2 | 4 | >100 | 35 | >100 | 3 |

TABLE 1A-continued

Antiviral activity of selected compounds (cell based assays)

| Co. No. | Structure | HCV Huh-7 (EC$_{50}$, μM) | DENV Huh-7 (EC$_{50}$, μM) | Tox Huh-7 (CC$_{50}$, μM) | DENV Vero (EC$_{50}$, μM) | Tox Vero (CC$_{50}$, μM) | CHIKV Huh-7 (EC$_{50}$, μM) |
|---|---|---|---|---|---|---|---|
| 27 | 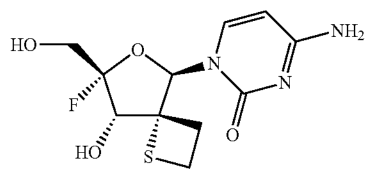 [SMILES: Nc1ccn([C@@H]2O[C@](F)(CO)[C@@H](O)[C@]23CCS3)c(=O)n1] | >100 | 77 | >100 | 50 | >100 | >100 |
| 31 | 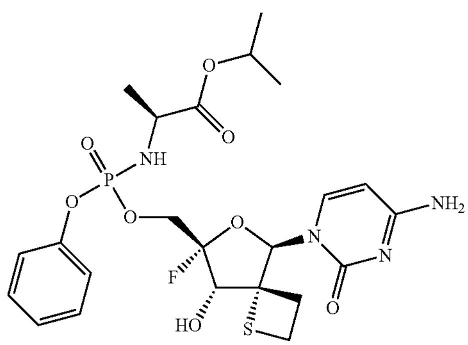 [SMILES: CC(C)OC(=O)[C@H](C)NP(=O)(OC[C@@]1(F)O[C@@H](n2ccc(N)nc2=O)[C@@]2(CCS2)[C@@H]1O)Oc1ccccc1] | 11 | 36 | >100 | >100 | >100 | >100 |
| 34 | 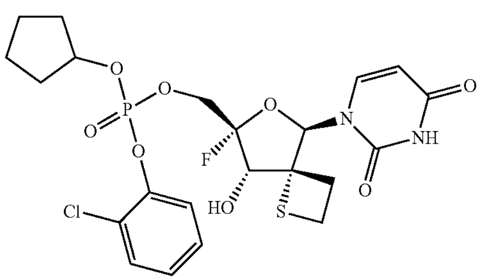 [SMILES: O=c1ccn([C@@H]2O[C@](F)(COP(=O)(Oc3ccccc3Cl)OC3CCCC3)[C@@H](O)[C@]23CCS3)c(=O)[nH]1] | >100 | 53 | >100 | 35 | >100 | >100 |
| 35 | 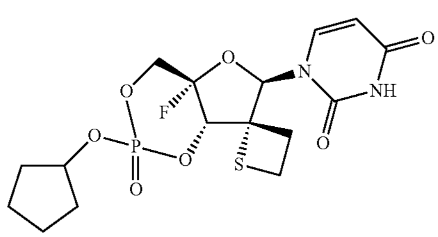 | 25 | >100 | >100 | >100 | >100 | 72 |
| 37 | 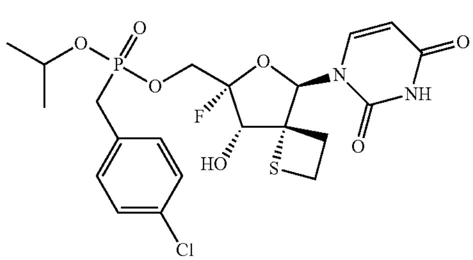 [SMILES: CC(C)OP(=O)(Cc1ccc(Cl)cc1)OC[C@@]1(F)O[C@@H](n2ccc(=O)[nH]c2=O)[C@@]2(CCS2)[C@@H]1O] | >100 | >100 | >100 | >100 | >100 | >100 |

TABLE 1A-continued

Antiviral activity of selected compounds (cell based assays)

| Co. No. | Structure | HCV Huh-7 (EC$_{50}$, μM) | DENV Huh-7 (EC$_{50}$, μM) | Tox Huh-7 (CC$_{50}$, μM) | DENV Vero (EC$_{50}$, μM) | Tox Vero (CC$_{50}$, μM) | CHIKV Huh-7 (EC$_{50}$, μM) |
|---|---|---|---|---|---|---|---|
| 39 | 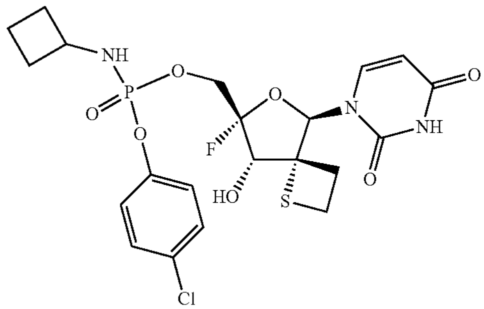 [SMILES: O=c1ccn([C@@H]2O[C@](F)(COP(=O)(NC3CCC3)Oc3ccc(Cl)cc3)[C@@H](O)[C@]23CCS3)c(=O)[nH]1] | >100 | 49 | >100 | 45 | >100 | >100 |
| 40a | 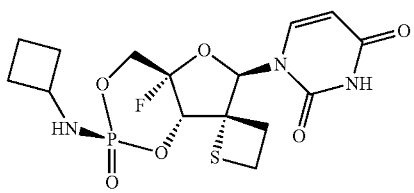 | >100 | >100 | >100 | >100 | >100 | >100 |
| 40b | 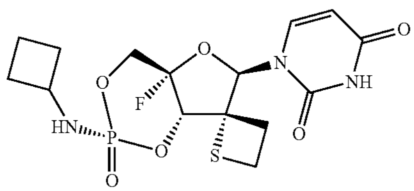 | >100 | >100 | >100 | >100 | >100 | >100 |
| 44 | 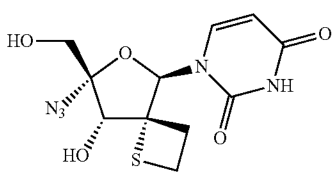 [SMILES: [N-]=[N+]=N[C@]1(CO)O[C@@H](n2ccc(=O)[nH]c2=O)[C@@]2(CCS2)[C@@H]1O] | >100 | >100 | >100 | >100 | >100 | >100 |
| 45 | 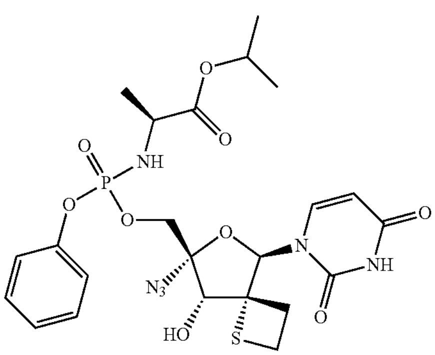 [SMILES: CC(C)OC(=O)[C@H](C)NP(=O)(OC[C@@]1(N=[N+]=[N-])O[C@@H](n2ccc(=O)[nH]c2=O)[C@@]2(CCS2)[C@@H]1O)Oc1ccccc1] | 5 | 62 | >100 | 62 | >100 | >100 |
| 57 | 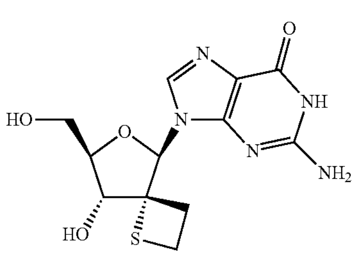 [SMILES: Nc1nc2c(ncn2[C@@H]2O[C@H](CO)[C@@H](O)[C@]23CCS3)c(=O)[nH]1] | — | — | — | — | — | — |

TABLE 1A-continued

Antiviral activity of selected compounds (cell based assays)

| Co. No. | Structure | HCV Huh-7 (EC$_{50}$, μM) | DENV Huh-7 (EC$_{50}$, μM) | Tox Huh-7 (CC$_{50}$, μM) | DENV Vero (EC$_{50}$, μM) | Tox Vero (CC$_{50}$, μM) | CHIKV Huh-7 (EC$_{50}$, μM) |
|---|---|---|---|---|---|---|---|
| 67 | (structure) | >50 | >50 | >50 | >50 | >50 | >50 |

TABLE 1B

Biochemical polymerase inhibition data

| Co. No. | Structure | HCV IC$_{50}$ (μM) | DENV2 IC$_{50}$ (μM) |
|---|---|---|---|
| 58 | (structure) | 0.74 | 49.75 |
| 59 | (structure) | 0.32 | 2.91 |
| 60 | (structure) | 0.69 | >10 |
| 61 | (structure) | 0.16 | 2.44 |

TABLE 1B-continued

Biochemical polymerase inhibition data

| Co. No. | Structure | HCV IC$_{50}$ (μM) | DENV2 IC$_{50}$ (μM) |
|---|---|---|---|
| 62 | [structure: triphosphate-sugar (3'-azido, spiro-thietane) uracil nucleoside] | 0.56 | — |
| 63 | [structure: triphosphate-sugar (spiro-thietane) guanine nucleoside] | 0.18 | >10 |
| 64 | [structure: triphosphate-sugar (spiro-thietane) adenine nucleoside] | | |

Table 1C shows the antiviral data of the compounds of the present invention obtained against HCV and CHIKV in comparison with the data obtained for spiro-oxetane derivatives. The data clearly show that the compounds of the present invention (first two lines of table 1C) are more active on HCV and CHIKV compared to the spiro-oxetane derivatives (last two lines of table 1C).

TABLE 1C

Antiviral activity of selected compounds of the present invention compared to spiro-oxetane derivatives.

| CO. NO. | Structure | HCV, Huh-7 (EC50, μM) | CHIKV, Huh7 (EC50, μM) |
|---|---|---|---|
| 9 | [structure: phosphoramidate prodrug of spiro-thietane uridine nucleoside] | 1 | 18 |

TABLE 1C-continued

Antiviral activity of selected compounds of the present invention compared to spiro-oxetane derivatives.

| CO. NO. | Structure | HCV, Huh-7 (EC50, μM) | CHIKV, Huh7 (EC50, μM) |
|---|---|---|---|
| 23 | 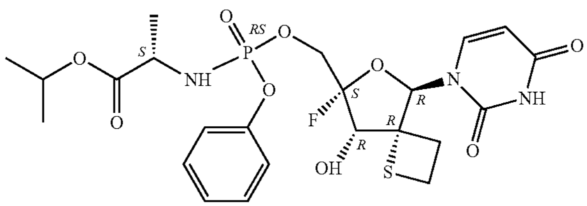 | 2 | 3 |
| | | 21 | >100 |
| | | >100 | >100 |

The invention claimed is:
1. A compound of Formula (I')

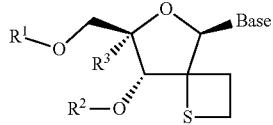 (I')

or a stereoisomeric form thereof, wherein
Base is selected from the group consisting of (B-1), (B-2), (B-3a), (B-3b), (B-4) and (B-5)

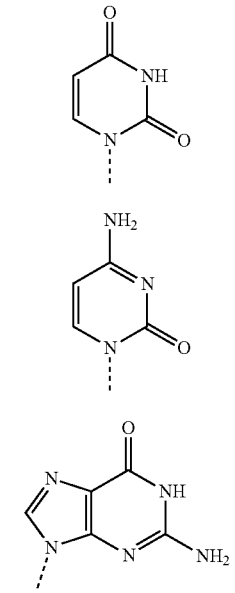
(B-1)
(B-2)
(B-3a)

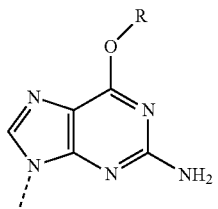
(B-3b)

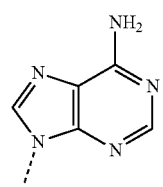
(B-4)

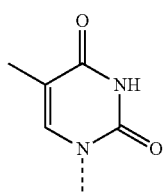
(B-5)

wherein R is hydrogen or $C_{1-6}$alkyl; and
wherein
$R^1$ is selected from the group consisting of hydrogen,

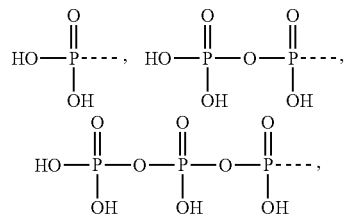

a group of formula (a-1), a group of formula (a-2), a group of formula (a-3), and a group of formula (a-4)

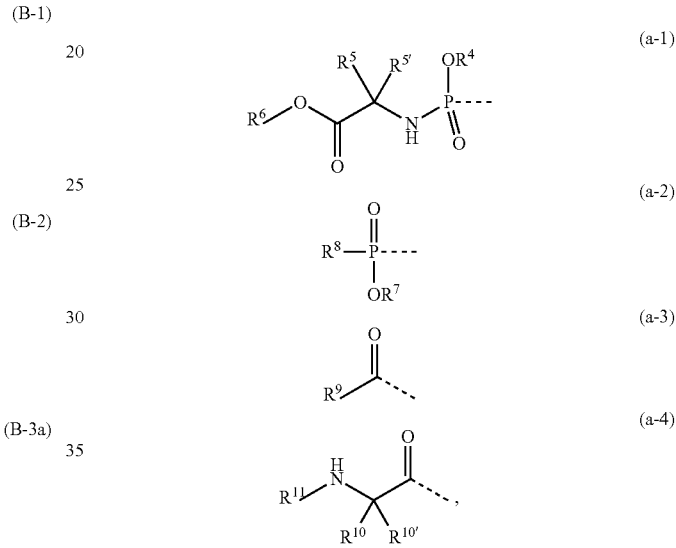
(a-1)
(a-2)
(a-3)
(a-4)

wherein
  $R^4$ and $R^7$ are each independently selected from the group consisting of hydrogen, phenyl, naphthyl, quinolinyl, isoquinolinyl, and pyridyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{16}R^{16'}$; or
  $R^4$ and $R^7$ are each independently indolyl, optionally substituted at its nitrogen atom with $C_1$-$C_6$alkyl or $C_1$-$C_6$alkyloxycarbonyl and/or at any available carbon atom with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{17}R^{17'}$;
  $R^5$, $R^{5'}$, $R^{10}$ and $R^{10'}$ are each independently selected from the group consisting of hydrogen, $C_1$-$C_6$alkyl, benzyl, and phenyl; or
  $R^5$ and $R^{5'}$, or $R^{10}$ and $R^{10'}$, together with the carbon atom to which they are attached form a $C_3$-$C_7$cycloalkanediyl or a 3- to 7-membered heterocyclic ring containing one oxygen atom;
  $R^6$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{18}R^{18'}$;

$R^8$ is —$OR^{19}$ or —$NR^{20}R^{20'}$;

$R^9$ is selected from the group consisting of $C_1$-$C_6$alkyl, phenyl, and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of halo and $C_1$-$C_6$alkyloxy;

$R^{11}$ is selected from the group consisting of hydrogen, $C_1$-$C_{10}$alkyl, $C_3$-$C_7$cycloalkyl, phenyl or phenyl-$C_1$-$C_6$alkyl-, wherein the phenyl moiety in phenyl or phenyl-$C_1$-$C_6$alkyl- is optionally substituted with 1, 2 or 3 substituents each independently selected from the group consisting of hydroxy, $C_1$-$C_6$alkoxy, and $NR^{23}R^{23'}$;

$R^{19}$ is selected from the group consisting of $C_1$-$C_6$alkyl, $C_3$-$C_7$cycloalkyl, oxetanyl, ($C_1$-$C_6$alkoxy)$C_1$-$C_6$alkyl-, —$CH_2$—O—(C=O)$C_1$-$C_6$alkyl, and —$CH_2$—O—(C=O)O$C_1$-$C_6$alkyl;

$R^{20}$ is selected from the group consisting of hydrogen, $C_1$-$C_6$alkyl, and $C_3$-$C_7$cycloalkyl; and $R^{20'}$ is selected from the group consisting of $C_1$-$C_6$alkyl, $C_3$-$C_7$cycloalkyl, and ($C_1$-$C_6$alkoxy)$C_1$-$C_6$alkyl-; or —$NR^{20}R^{20'}$ together form an azetidinyl, a pyrrolidinyl or a piperidinyl ring, each of which may be optionally substituted with a group consisting of hydroxy, $C_1$-$C_6$alkyl, $C_1$-$C_6$alkyloxy, and (C=O)—$OR^{21}$ wherein $R^{21}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{22}R^{22'}$;

$R^2$ is hydrogen or a group of formula (b)

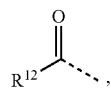

(b)

wherein $R^{12}$ is selected from the group consisting of $C_1$-$C_6$alkyl, phenyl, and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of halo and $C_1$-$C_6$alkyloxy; or $R^1$ and $R^2$ are bound to form a divalent radical of formula (c-1) or (c-2)

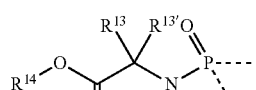

(c-1)

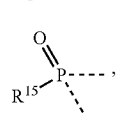

(c-2)

wherein $R^{13}$ and $R^{13'}$ are each independently selected from the group consisting of hydrogen, $C_1$-$C_6$alkyl, benzyl, and phenyl; or $R^{13}$ and $R^{13'}$, together with the carbon atom to which they are attached form a $C_3$-$C_7$cycloalkanediyl or a 3- to 7-membered heterocyclic ring containing one oxygen atom;

$R^{14}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{24}R^{24'}$;

$R^{15}$ is —$OR^{25}$ or —$NR^{26}R^{26'}$, wherein $R^{25}$ is selected from the group consisting of hydrogen; $C_1$-$C_6$alkyl; $C_1$-$C_3$alkyl substituted with 1, 2 or 3 substituents each independently selected from the group consisting of phenyl, naphthyl, $C_3$-$C_7$cycloalkyl, hydroxyl and $C_1$-$C_6$alkyloxy; $C_3$-$C_7$cycloalkyl; ($C_1$-$C_6$alkoxy)$C_1$-$C_6$alkyl-; —$CH_2$—O—(C=O)$C_1$-$C_6$alkyl; —$CH_2$—O—(C=O)O$C_1$-$C_6$alkyl; a 3- to 7-membered heterocyclic ring containing one oxygen atom; and Ar; wherein Ar is selected from the group consisting of phenyl, naphthyl, quinolinyl, isoquinolinyl, and pyridyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{27}R^{27'}$; or Ar is indolyl, optionally substituted at its nitrogen atom with $C_1$-$C_6$alkyl or $C_1$-$C_6$alkyloxycarbonyl and/or at any available carbon atom with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{28}R^{28'}$;

$R^{26}$ is selected from the group consisting of hydrogen, $C_1$-$C_6$alkyl, and $C_3$-$C_7$cycloalkyl; and $R^{26'}$ is selected from the group consisting of $C_1$-$C_6$alkyl, $C_3$-$C_7$cycloalkyl, and ($C_1$-$C_6$alkoxy)$C_1$-$C_6$alkyl-; or —$NR^{26}R^{26'}$ together form an azetidinyl, a pyrrolidinyl or a piperidinyl ring, each of which may be optionally substituted with a group consisting of hydroxy, $C_1$-$C_6$alkyl, $C_1$-$C_6$alkyloxy, and (C=O)—$OR^{27}$ wherein $R^{27}$ is selected from the group consisting of $C_1$-$C_{10}$alkyl, $C_3$-$C_7$cycloalkyl, phenyl and phenyl-$C_1$-$C_6$alkyl-, wherein the phenyl moiety in phenyl or phenyl-$C_1$-$C_6$alkyl- is optionally substituted with 1, 2 or 3 substituents, each independently selected from the group consisting of hydroxy, $C_1$-$C_6$alkoxy, and $NR^{29}R^{29'}$;

$R^{16}, R^{16'}, R^{17}, R^{17'}, R^{18}, R^{18'}, R^{22}, R^{22'}, R^{23}, R^{23'}, R^{24}, R^{24'}, R^{27}, R^{27'}, R^{28}, R^{28'}, R^{29}$ and $R^{29'}$ are each independently selected from hydrogen and $C_1$-$C_6$alkyl; and $R^3$ is selected from the group consisting of hydrogen, halo, methyl, $CH_2Cl$, $CH_2F$ and $N_3$, or a pharmaceutically acceptable salt or a solvate thereof.

2. The compound according to claim 1, wherein $R^1$ is selected from the group consisting of hydrogen,

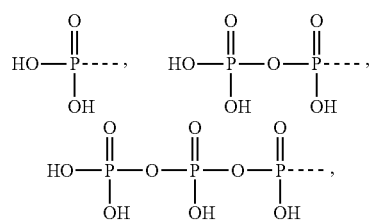

a group of formula (a-1), a group of formula (a-2) and a group of formula (a-3); wherein $R^4$ and $R^7$ are each independently phenyl or naphthyl, each of which being optionally substituted with 1, 2, or 3 substituents, each independently selected from the group consisting of halo, $C_1$-$C_6$alkyl, $C_2$-$C_6$alkenyl, $C_1$-$C_6$alkoxy, hydroxy, and $NR^{16}R^{16'}$; wherein $R^{16}$ and $R^{16'}$ are each independently selected from hydrogen and $C_1$-$C_6$alkyl; or $R^4$ and $R^7$ are each independently indolyl;

$R^5$ and $R^{5'}$ are each independently selected from the group consisting of hydrogen, $C_1$-$C_6$alkyl, benzyl, and phenyl; or $R^5$ and $R^{5'}$ together with the carbon atom to which they are attached form a $C_3$-$C_7$cycloalkanediyl;

$R^6$ is selected from the group consisting of $C_1$-$C_{10}$alkyl, $C_3$-$C_7$cycloalkyl and phenyl-$C_1$-$C_6$alkyl-;

$R^8$ is —$OR^{19}$ or —$NR^{20}R^{20'}$; wherein $R^{19}$ is $C_1$-$C_6$alkyl or $C_3$-$C_7$cycloalkyl;

$R^{20}$ is hydrogen and $R^{20'}$ is $C_1$-$C_6$alkyl or $C_3$-$C_7$cycloalkyl; and $R^9$ is $C_1$-$C_6$alkyl;

$R^2$ is hydrogen or a group of formula (b), wherein $R^{12}$ is $C_1$-$C_6$alkyl; or $R^1$ and $R^2$ are bound to form a divalent radical of formula (c-1) or (c-2), wherein $R^{13}$ and $R^{13'}$ are each independently selected from the group consisting of hydrogen, $C_1$-$C_6$alkyl, benzyl, and phenyl; or $R^{13}$ and $R^{13'}$, together with the carbon atom to which they are attached form a $C_3$-$C_7$cycloalkanediyl;

$R^{14}$ is selected from the group consisting of $C_1$-$C_{10}$alkyl, $C_3$-$C_7$cycloalkyl and phenyl-$C_1$-$C_6$alkyl-; and $R^{15}$ is —$OR^{25}$ or —$NR^{26}R^{26'}$, wherein $R^{25}$ is selected from the group consisting of $C_1$-$C_6$alkyl; phenyl; $C_3$-$C_7$cycloalkyl; and $C_1$-$C_3$alkyl substituted with 1, 2 or 3 substituents each independently selected from the group consisting of phenyl, naphthyl, $C_3$-$C_7$cycloalkyl, hydroxyl and $C_1$-$C_6$alkyloxy; $R^{26}$ is hydrogen; and $R^{26'}$ is $C_1$-$C_6$alkyl or $C_3$-$C_7$cycloalkyl.

3. The compound according to claim 1, wherein $R^1$ is selected from the group consisting of hydrogen,

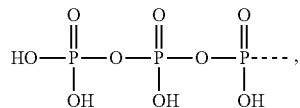

and a group of formula (a-1);
or $R^1$ and $R^2$ are bound to form a divalent radical of formula (c-2).

4. The compound according to claim 1, wherein
$R^4$ is phenyl, halophenyl, di$C_1$-$C_4$alkylphenyl, or naphthyl;
$R^5$ and $R^{5'}$ are each independently hydrogen, $C_1$-$C_6$alkyl, benzyl, or phenyl;
$R^6$ is $C_1$-$C_6$alkyl; and
$R^{15}$ is —$OR^{25}$ wherein $R^{25}$ is $C_1$-$C_6$alkyl or $C_1$-$C_2$alkyl substituted with phenyl, $C_1$-$C_2$alkyloxy or $C_3$-$C_7$cycloalkyl.

5. The compound according to claim 1, wherein Base is (B-1), (B-2) or (B-3a) and $R^3$ is selected from the group consisting of hydrogen, halo, and $N_3$.

6. A pharmaceutical composition comprising a therapeutically effective amount of a compound of claim 1 and a pharmaceutically acceptable carrier.

7. A process for preparing a pharmaceutical composition comprising intimately mixing a pharmaceutically acceptable carrier with a therapeutically effective amount of a compound of claim 1.

8. A method of treating a warm-blooded animal infected by Flaviviridae and/or alphavirus comprising administering an anti-Flaviviridae and/or anti-alphavirus effective amount of a compound of Formula (I) as defined in claim 1.

9. A product comprising a compound of claim 1 and an additional pharmaceutical agent as a combined preparation for simultaneous, separate or sequential use in the treatment of Flaviviridae virus infections, and/or in the treatment of alphavirus infections.

* * * * *